US007098025B1

(12) United States Patent
Auwerx et al.

(10) Patent No.: US 7,098,025 B1
(45) Date of Patent: Aug. 29, 2006

(54) HUMAN PEROXISOME PROLIFERATOR ACTIVATED RECEPTOR GAMMA (PPARγ) GENE REGULATORY SEQUENCES AND USES THEREFOR

(75) Inventors: Johan Auwerx, Millionfosse (FR); Lluis Fajas, Montpellier (FR); Michael R. Briggs, Chesterfield, MO (US); Regis Saladin, Denain (FR)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 0 days.

(21) Appl. No.: 09/463,542

(22) PCT Filed: Jul. 24, 1998

(86) PCT No.: PCT/US98/15411

§ 371 (c)(1), (2), (4) Date: Dec. 11, 2002

(87) PCT Pub. No.: WO99/05161

PCT Pub. Date: Feb. 4, 1999

Related U.S. Application Data

(60) Provisional application No. 60/053,692, filed on Jul. 25, 1997.

(51) Int. Cl.
*C12N 15/00* (2006.01)
*C12N 15/11* (2006.01)
*C12N 5/00* (2006.01)
*C12P 21/06* (2006.01)

(52) U.S. Cl. ...................... 435/320.1; 435/69.1; 435/6; 435/91.4; 435/325; 536/23.1; 536/24.1

(58) Field of Classification Search ............... 435/69.1, 435/320.1, 6, 91.4; 536/23.1, 24.1
See application file for complete search history.

(56) References Cited

U.S. PATENT DOCUMENTS 3,845,089 A 10/1974 Henrick ...................... 554/220
3,884,758 A 5/1975 Green ......................... 435/34
4,105,681 A 8/1978 Bollag et al. ............... 554/111
4,193,931 A 3/1980 Loeliger ..................... 514/510
4,215,215 A 7/1980 Bollag et al. ............... 544/176
4,534,979 A 8/1985 Love et al. ................. 514/529
4,648,996 A 3/1987 Aig et al. ................... 554/103
4,783,549 A 11/1988 Lang et al. ................ 560/104
4,833,254 A 5/1989 Berlin et al. ................ 548/454
4,879,284 A 11/1989 Land et al. ................... 514/62
4,892,940 A 1/1990 Maignan et al. ........... 536/55.2
4,945,050 A 7/1990 Sanford et al. ............. 435/459
4,977,276 A 12/1990 Berlin et al. .................. 549/58
5,130,333 A 7/1992 Pan et al. ................... 514/460
5,198,567 A 3/1993 Lang et al. ................... 560/56
5,219,888 A 6/1993 Katocs, Jr. et al. ......... 514/560
5,264,372 A 11/1993 Beaumont et al. .......... 436/504
5,304,575 A 4/1994 Beck .......................... 514/563
5,441,971 A 8/1995 Sohda et al. ................ 514/342
5,498,696 A 3/1996 Briggs et al. ............... 530/350
5,512,683 A 4/1996 Klaus et al. .................... 549/9
5,527,690 A 6/1996 Goldstein et al. .......... 435/69.1
5,654,338 A 8/1997 Metivier ..................... 514/570
5,683,880 A 11/1997 Kamb ........................... 435/6
5,686,596 A 11/1997 Mukherjee ................. 536/23.5
5,700,836 A 12/1997 Klaus et al. ................ 514/544
5,705,167 A 1/1998 Bernardon et al. ......... 424/401
5,707,803 A 1/1998 Lamb et al. .................... 435/6
5,726,041 A 3/1998 Chrespi et al. ............ 435/69.1
5,728,739 A 3/1998 Ailhaud et al. ............. 514/725
5,763,487 A 6/1998 Bernardon .................. 514/569
5,780,676 A 7/1998 Boehm et al. .............. 562/490
5,814,517 A 9/1998 Seidel et al. ................ 435/325
5,891,631 A 4/1999 Goldstein et al. .............. 435/6
5,962,731 A 10/1999 Boehm et al. .............. 562/460
5,968,908 A 10/1999 Epstein et al. ................ 514/42
5,972,881 A 10/1999 Heyman et al. ............... 514/3
5,977,125 A 11/1999 Hibi et al. .................. 514/277
6,017,924 A 1/2000 Edwards et al. ............ 514/292
6,028,052 A 2/2000 Heyman et al. ............... 514/3
6,043,279 A 3/2000 Boehm et al. .............. 514/568
6,068,976 A 5/2000 Briggs et al. ................... 435/6
6,200,802 B1 3/2001 Greene et al. .............. 435/325
6,228,862 B1 5/2001 Heyman et al. ............ 514/277
6,316,404 B1 11/2001 Heyman et al. ............... 514/3
6,320,074 B1 11/2001 Boehm et al. .............. 562/490
6,417,212 B1 7/2002 Brooks et al. .............. 514/374

(Continued)

FOREIGN PATENT DOCUMENTS

DE 2819213 9/1987

(Continued)

OTHER PUBLICATIONS

Barnett et al., "Effect of clofibrate on glucose tolerance in maturity onset diabetes," British Journal of Clinical Pharmacology 4:455-458 (1977).

(Continued)

*Primary Examiner*—Dave Trong Nguyen
*Assistant Examiner*—Maria Marvich
(74) *Attorney, Agent, or Firm*—Fish & Richardson P.C.; Stephanie Seidman; Frank J. Miskiel

(57) ABSTRACT

This invention relates to the isolation and cloning of the promoter and other control regions of human PPARγ gene. It provides a method for identifying and screening for agents useful for the treatment of diseases and pathological conditions affected by the level of expression of the PPARγ gene. These agents interact directly or indirectly with the promoter or other control regions of the PPARγ gene.

12 Claims, 6 Drawing Sheets

U.S. PATENT DOCUMENTS

Figure 2A:
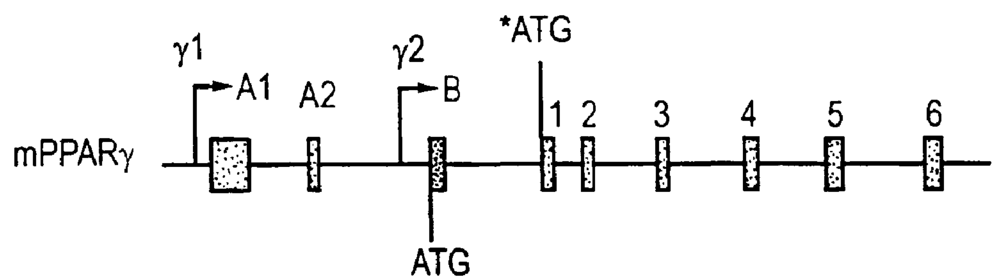

| | | | | |
|---|---|---|---|---|
| 6,521,633 | B1 | 2/2003 | Heyman et al. | 514/277 |
| 6,534,516 | B1 | 3/2003 | Edwards et al. | 514/285 |
| 6,545,049 | B1 | 4/2003 | Canan-Koch et al. | 514/569 |
| 6,593,493 | B1 | 7/2003 | Ardecky et al. | 562/465 |
| 6,610,696 | B1 | 8/2003 | Brooks et al. | 514/256 |
| 6,610,883 | B1 | 8/2003 | Boehm et al. | 562/490 |
| 6,815,168 | B1 | 11/2004 | Greene et al. | 435/7.1 |
| 6,825,222 | B1 | 11/2004 | Brooks et al. | 514/365 |
| 2002/0144302 | A1 | 10/2002 | Mahfoudl | 800/21 |
| 2002/0193291 | A1 | 12/2002 | Heyman et al. | 514/3 |
| 2003/0104975 | A1 | 6/2003 | Auwerx et al. | 514/1 |
| 2004/0019072 | A1 | 1/2004 | Canan-Koch et al. | 514/290 |
| 2004/0019090 | A1 | 1/2004 | Brooks et al. | 514/365 |
| 2004/0082623 | A1 | 4/2004 | Rochhi et al. | 514/357 |
| 2004/0106135 | A1 | 6/2004 | Mukherjee et al. | 435/6 |
| 2004/0171689 | A1 | 9/2004 | Desreumaux et al. | 514/559 |

FOREIGN PATENT DOCUMENTS

| | | |
|---|---|---|
| EP | 0169571 | 1/1986 |
| EP | 0253393 | 1/1988 |
| EP | 0266992 | 5/1988 |
| EP | 0 305 890 | 3/1989 |
| EP | 0 139 417 | 7/1989 |
| EP | 0 569 237 | 11/1993 |
| EP | 0679628 | 11/1995 |
| EP | 0698392 | 2/1996 |
| EP | 0718285 | 6/1996 |
| EP | 0552624 | 7/1997 |
| EP | 0568898 | 4/1998 |
| EP | 0641759 | 12/1998 |
| EP | 0873295 | 4/2003 |
| EP | 1336600 | 8/2003 |
| EP | 0859608 | 2/2004 |
| EP | 1426048 | 6/2004 |
| FR | 2390428 | 12/1978 |
| FR | 2719041 | 10/1995 |
| FR | 2719042 | 10/1995 |
| FR | 2729664 | 7/1996 |
| GB | 2188634 | 10/1987 |
| GB | 2197316 | 5/1988 |
| JP | 05 194 209 A | 8/1993 |
| WO | 83/00930 | 3/1983 |
| WO | 89/04489 | 5/1989 |
| WO | 91/01384 | 2/1991 |
| WO | 91/12258 | 8/1991 |
| WO | 92/20642 | 11/1992 |
| WO | 93/09236 | 5/1993 |
| WO | 93/15740 | 8/1993 |
| WO | 93/21146 | 10/1993 |
| WO | 94/12880 | 6/1994 |
| WO | 94/15901 | 7/1994 |
| WO | 94/15902 | 7/1994 |
| WO | 94/17796 | 8/1994 |
| WO | 94/18959 | 9/1994 |
| WO | 95/04036 | 2/1995 |
| WO | 95/07694 | 3/1995 |
| WO | 95/07697 | 3/1995 |
| WO | 95/11974 | 5/1995 |
| WO | 95/23225 | 8/1995 |
| WO | 96/01430 | 1/1996 |
| WO | 96/05165 | 2/1996 |
| WO | 96/13478 | 5/1996 |
| WO | 96/20913 | 7/1996 |
| WO | 96/23884 | 8/1996 |
| WO | 96/29405 | 9/1996 |
| WO | 97/10813 | 3/1997 |
| WO | 97/10819 | 3/1997 |
| WO | 97/12853 | 4/1997 |
| WO | 97/25042 | 7/1997 |
| WO | 97/33881 | 9/1997 |
| WO | 98/05331 | 2/1998 |
| WO | 98/21349 | 5/1998 |
| WO | 98/43081 | 10/1998 |
| WO | 99/05161 | 2/1999 |
| WO | 99/51740 | 10/1999 |
| WO | 02/00611 | 1/2002 |
| WO | 02/094877 | 11/2002 |

OTHER PUBLICATIONS

Berger et al., "Interaction of Glucocorticoid Analogues with the Human Glucocorticoid Receptor," J. Steroid. Biochem. Molec. Biol. 41: 733-738 (1992).

Boehm et al, "Synthesis and structure-activity relationships of novel retinoid X receptor-selective retinoids," J. of Medicinal Chemistry 37(18):2930-41 (1994).

Broach, J.R., "The Yeast of Plasmid 2μ Circle," In: The Molecular Biology of the Yeast Saccharomyces: Life Cycle and Inheritance, Cold Spring Harbor Laboratory, Cold Spring Harbor, N.Y., pp. 445-470 (1981).

Carter S.K. et al.(Eds.) Chemotherapy of Cancer, 2nd edition, New York: John Wiley & Sons, Appendix C, pp.364-365 (1981).

Chater et al., "Streptomyces ØC31-Like Phages: Cloning Vectors, Genome Changes and Host Range," In: Sixth International Symposium on Actinomycetes Biology, Debrecen, Hungary, Aug. 26-30, 1985, pp. 45-54 (1986).

Chemical Abstracts Accession No. 123:281583 for Motojima, K, "Toward the treatment of obesity. Role of PPAR Gamma in Adipogenesis," Tanpakushitsu Kakusan Koso 40(13):1936-1941 (1995).

Crombie et al., "Creatine kinase activity as an indicator of unopposed estrogen action in the mouse uterus associated with anti-progesterone treatment." J. Steroid Biochem Mol Biol. 49(2-3)123-9 (1994).

Derwent Abstract for JP 05 194 209A, published Aug. 3, 1993, entitled "Vascular endothelial cell function improvers—contains fenofibrate e.g. isopropyl 2-(p-(p-chloro:benzoyl)phenoxy)-2-methyl propionate".

Dreborg et al., "The chemistry and standardization of allergens," Chapter 10 in the *Handbook of Experimental Immunology*, 4th Ed., D.M. Weir et al. (Ed.), Oxford ; Boston : Blackwell Scientific Publications, pp. 10.1-10.27(1986).

Giguere et al., "Functional Domains of the Human Glucocrticoid Receptor," Cell 46:645-652 (1986).

Giguere et al., "Identification of a receptor for the morphogen retinoic acid," Nature 330(2):624-629 (1987).

Grundy et al., "Metabolic and Health Complications of Obesity," Disease-a-Month 36(12):645-696 (1990).

Gryczan, T.J., "Molecular Cloning in *Bacillus subtilis*," In: The Molecular Biology of the Bacilli, New York: Academic Press, Inc., pp.307-329 (1982).

Ibrahimi et al., "Evidence for a Common Mechanism of Action for Fatty Acids and Thiazolidinedione Antidiabetic Agents on Gene Expression in Preadipose Cells," Molecular Pharmacology 46:1070-1076 (1994).

Jow, L. and R. Mukherjee, "The human peroxisome proliferator-activated recepetor (PPAR) subtype NUC1 represses the activation of hPPARα and thyroid hormone receptors," .J Biol Chem. 270(8):3836-40 (1995).

Karam, J., "Type II Diabetes and Syndrome X," Endocrinology and Metabolism Clinics of North America 21(2): 329-350 (1992).

Kawamatsu et al., "Studies on Antihyperlipidemic Agents," Arzneim-Forsch 30: 454-459 (1980).

Lenhard et al., "Analysis of Thiazolidinedione, Biguanide and Retinoid Effects on Adipogenesis and the Nuclear Receptors PPARγ and RXR," Diabetologia, Supplement 39(5): A234 (1996).

Mangelsdorf et al., "A Direct Repeat in the Cellular Retinol-Binding Protein Type II Gene Confers Differential Regulation by RXR and RAR," Cell 66:555-561 (1991).

Mangelsdorf et al., "Nuclear receptor that identifies a novel retinoic acid reponse pathway," Nature 345:224-229 (1990).

Maniatis, T., "Recombinant DNA Procedures in the Study of Eukaryotic Genes," In: Cell Biology: A Comprehensive Treatise, vol. 3, Gene Sequence Expression, New York: Academic Press, pp.563-608 (1980).
Miller et al., "An Insect Baculovirus Host-Vector System for High-Level Expression of Foreign Genes," In: Genetic Engineering: Principles and Methods, Setlow, J. K. et al. (Eds.), New York: Plenum Press, vol. 8, pp. 277-297 (1986).
Motojima, K, "[Toward the treatment of obesity. Role of PPAR Gamma in Adipogenesis]," Tanpakushitsu Kakusan Koso 40(13):1936-1941 (1995) [In Japanese].
Mukherjee, R., "Selective binding of the estrogen receptor to one strand of the estrogen responsive element, " Nucleic Acids Res. 21(11):2655-2661 (1993).
Nestel, P.J., "Effects of N-3 fatty acids on lipid metabolism," Ann. Rev. Nutr. 10:149-167 (1990).
Ptashne, M., "How eukaryotic transcriptional activators work," Nature 335:683-689 (1988).
Rigas et al., "Lipoprotein alterations in patients treated with novel retinoids," Proceeding of the American Association for Cancer Research, 86th Annual Meeting, Toronto, Ontario, Canada, Mar. 18-22, 1995, vol. 36, p. 506 (Mar., 1995).
Römpp Chemie Lexikon, 9th Extended and Revised Edition, S., Falbe, J. et al. (Eds.) Georg Thieme Verlag Stuggart: New York, pp. 3855-3856 (1992) [Pages in German].
Safonova et al., "Fatty Acids and Retinoids Act Synergistically on Adipose Cell Differentiation," Biochem Biophys Res Commun. 204(2):498-504 (1994).
St. Groth et al., "Production of Monoclonal Antibodies: Strategy and Tactics," J. Immunol. Methods 35:1-21 (1980).
Ullmann's Encyclopedia of Industrial Chemistry, 5th Ed. vol. A8: Coronary Therapeutics to Display Technology, Gerhartz, W. et al. (Eds.) VCH: Weinheim, Federal Republic of Germany), pp. 308-314 (1987).
Umesono et al., "Retinoic acid and thyroid hormone induce gene expression through a common responsive element," Nature 336:262-265 (1988).
Wu, G.Y. and C.H. Wu, "Receptor-mediated *in Vitro* Gene Transformation by a Soluble DNA Carrier-System," J. Biol. Chem. 262: 4429-4432 (1987).
Zhang et al., "Characterization of Protein-DNA Interactions with the Peroxisome Proliferator-responsive Element of the Rat Hydratase-Dehydrogenase Gene," Journal of Biological Chemistry 268:12939-12945 (1993).
Zhang et al., "Positional cloning of the mouse *obese* gene and its human homologue," Nature 372(6505):425-432 (1994).
Amri et al., "Regulation of adipose cell differentiation. I. Fatty acids are inducers of the aP2 gene expression," J. Lipid Research 32:1449-1456 (1991).
Amri et al., "Regulation of adipose cell differentiation. II. Kinetics of induction of the aP2 gene by fatty acids and modulation by dexamethasone," J. Lipid Res. 32: 1457-1463 (1991).
Aperlo et al., "cDNA cloning and characterization of the transcriptional activities of the hamster peroxisome proliferators-activated receptor haPPARγ," Gene 162:297-302 (1995).
Aubert et al., "Evidence for a novel regulatory pathway activated by (carba)prostacyclin in preadipose and adipose cells," FEBS Letters 397: 117-121 (1996).
Auwerx et al., "Transcription, adipocyte differentiation, and obesity," J. Mol. Med. 74: 347-352 (1996).
Auwerx et al., "Transcriptional control of triglyceride metabolism: fibrates and fatty acids change the expression of the LP1 and C-III genes by activating the nuclear receptor PPAR," Atherosclerosis 124(Suppl.): S29-S37 (1996).
Belluzi et al., "Effect of an enteric-coated fish-oil preparationon on relapses in crohn's disease," N. Engl. J. Med. 334: 1557-1560 (1996).
Berger et al., "Thiazolidinediones produce a conformational change in peroxisomal proliferators-activated receptor-γ: binding and activation correlate with antidiabetic actions in db/db mice," Endocrinology 137: 4189-4195 (1996).
Brandes et al., "Adipocyte conversion of cultured 3T3-L1 preadipocytes by bezafibrate," Life Sciences 40: 935-941 (1987).
Brinster et al., "Factors affecting the efficiency of introducing foreign DNA into mice by microinjecting eggs," Proc. Nat. Acad. Sci. USA 82: 4438-4442 (1985).
Brun et al., "Differential activation of adipogenesis by multiple PPAR isoforms," Genes & Development 10: 974-984 (1996).
Bunin, B.A. and J.A. Ellman, "A general and expedient method for the solid-phase synthesis of 1,4 benzodiazepine derivatives," J. Am. Chem. Soc. 114:10997-10998 (1992).
Capecchi, M.R., "High efficiency transformation by direct microinjection of DNA into cultured mammalian cells," Cell 22:479-488 (1980).
Capecchi, M.R., "Altering the genome by homologous recombination," Science 244: 1288-1292 (1989).
Cech, T.R., "Ribozymes and their medical implications," J. Am. Med. Assoc. 260:3030-3034 (1988).
Chawla, A. and M.A. Lazar, "Peroxisome proliferators and retinoid signaling pathways co-regulate preadipocyte phenotype and survival," Proc. Natl. Acad. Sci. U.S.A. 91: 1786-1790 (1994).
Chen C. and H. Okayama, "High-Efficiency Transformation of Mammalian Cells by Plasmid DNA," Mol. Cell Biol. 7:2745-2752 (1987).
Chen et al., "Identification of two mPPAR related receptors and evidence for the existence of five subfamily members," Biochemical and Biophysical Research Communications 196:671-677 (1993).
Christy et al., "Differentiation-induced gene expression in 3T3-L1 preaddipocytes: CCAAT/enhancer binding protein interacts with and activates the promoters of two adipocyte-specific genes," Genes & Development 3: 1323-1335 (1989).
Chu et al., "Electroporation for the efficient transfection of mammalian cells with DNA, " Nucleic Acids Res. 15:1311-1326 (1987).
Cornelius et al., "Regulation of adipocyte development," Annu. Rev. Nutr. 14: 99-129 (1994).
Cristiano et al., "Hepatic gene therapy: adenovirus enhancement of receptor-mediated gene delivery and expression in primary hepatocytes," Proc. Natl. Acad. Sci. USA 90:2122-2126 (1993).
Curiel et al., "Gene transfer to respiratory epithelial cells via the receptor-mediated endocytosis pathway," Am. J. Respir. Cell. Mol. Biol. 6:247-252 (1992).
Davidson et al., "A model system for in vivo gene transfer into the central nervous system using an adenoviral vector," Nature Genetics 3:219-223 (1993).
De Vos et al., "Thiazolidinediones repress *ob* gene expression in rodents via activation of peroxisome proliferator-activated receptor γ," J. Clin. Invest. 98(4):1004-1009 (1996).
De Vos et al., "Induction of *ob* gene expression by corticosteroids is accompanied by body weight loss and reduced food intake," J Biol Chem. 270(27):15958-15961 (1995).
De Vos et al., "Glucocorticoids induce the expression of the leptin gene through a non-classical mechanism of transcriptional activation," Eur. J. Biochem. 253(3):619-26 (1998).
Desreumaux et al., "Attenuation of colon inflammation through activators of the retinoid X receptor (RXR)/peroxisome proliferator-activated receptor γ (PPARγ) heterodimer: A basis for new therapeutic strategies," J Exp Med. 193(7):827-38 (2001).
Desvergene, B. and W. Wahli, "PPAR: a key nuclear factor in nutrient/gene interactions," Chapter 5 in *Inducible Gene Expressio, vol. 1: Environmental Stresses and Nutrients*, P.A. Baeuerle (Ed.) Boston: Birkhäuser. 1: 142-176 (1995).
Devchand et al., "The PPARα-leukotriene $B_4$ , pathway to inflammation control," Nature 384: 39-43 (1996).
Dreyer et al., "Control of the perxisomal β-oxidation pathway by a novel family of nuclear hormone receptors," Cell 68: 879-887 (1992).
Elbrecht et al., "Molecular cloning, expression and characterization of human peroxisome proliferators activated receptors γ1 and γ2," Biochem. Biophys. Res. Commun. 224: 431-437 (1996).
Fajas et al., "The organization, promoter analysis, and expression of the human PPARγ gene," J. Biol. Chem. 272:18779-18789 (1997).
Fajas et al., "Regulation of peroxisome proliferator-activated receptor γ expression by adipocyte differentiation and determination factor 1/sterol regulatory element binding protein 1: Implications for adipocyte differentiation and metabolism," Mol Cell Biol. 19(8):5495-5503 (1999).
Felgner, P.L. and G.M. Ringold, "Cationic liposome-mediated transfection," Nature 337:387-388 (1989).
Felgner et al., "Lipofection: A highly efficient, lipid-mediated DNA-transfection procedure," Proc. Natl. Acad. Sci. USA 84:7413-7417 (1987).
Ferrari et al., "An in vivo model of somatic cell gene therapy for human severe combined immunodeficiency," Science 251:1363-1366 (1991).
Fingl, E. and D.M. Woodbury, "General Principles," Chapter 1 in The Pharmacological Basis of Therapeutics, Goodman et al. (Eds.) New York: Macmillan Publishing Co., pp. 1-46 (1975).
Flier, J. S., "The adipocyte: storage depot or node on the energy information superfamily," Cell 80: 15-18 (1995).
Forman et al., "15-Deoxy-$\Delta^{12,14}$-Prostaglandin $J_2$ is a ligand for the adipocyte determination factor PPARγ," Cell 83: 803-812 (1995).
Freytag, S. and T.J. Geddes, "Reciprocal regulation of adipogenesis by Myc and C/EBPα," Science 256: 379-382 (1992).
Freytag et al., "Ectopic expression of the CCAAT/enhancer-binding protein α promotes the adipogenic program in a variety of mouse fibroblastic cells," Genes & Development 8: 1654-1663 (1994).
Fried, M.G. and D.M. Crothers, "CAP and RNA polymerase interactions with the *lac* promoter: binding stoichiometry and long range effects," Nucl. Acids Res. 11:141-158 (1983).
Gaillard et al., "Requirement and role of arachidonic acid in the differentiation of pre-adipose cells," Biochem. J. 257: 389-397 (1989).
Gearing et al., "Structure of the mouse peroxisome proliferators activated receptor α gene," 199(1): 255-263 (1994).
Gharbi-Chibi et al., "Increase of adipose differentiation by hypolipidemic fibrate drugs in Ob 17 preadipocytes: requirements for thyroid hormones," Biochem. Biophys. Acta 1177: 8-14 (1993).
Giovanucci, E. and W.C. Willet, "Dietary factors and risk of colon cancer," Ann. Med. 26: 443-452 (1994).
Goring et al., "In Situ detection of β-galactosidase in lenses of transgenic mice with a γ-Crystallin/*lacZ* gene," Science 235:456-458 (1987).
Göttlicher et al., "Fatty acids activate a chimera of the clofibric acid-activated receptor and the glucocorticoid receptor," Proc. Natl. Acad. Sci. USA. 89:4653-4657 (1992).
Green, S., "PPAR: a mediator of peroxisome proliferator action," Mutation Research 333: 101-109 (1995).
Greene et al., "Isolation of the human peroxisome proliferators activated receptor gamma cDNA: expression in hematopoietic cells and chromosomal mapping," Gene Expression 4: 281-299 (1995).
Hallakou et al., Pioglitazone induces in vivo adipocyte differentiation in the obese Zucker *fa/fa* rat. Diabetes 46(9):1393-1399 (1997).
Hambor et al., "Functional consequences of anti-sense RNA-mediated inhibition of CD8 surface expression in a human T cell clone," J. Exp. Med. 168:1237-1245 (1988).
Hammer et al., "Spontaneous inflammatory disease in transgenic rats expressing HLA-B27 and human $\beta_2$m: An animal model of HLA-B27-associated human disorders," Cell 63:1099-1112 (1990).
Hertz et al., "Thyromimetic mode of action of peroxisome proliferators: activation of malic' enzyme gene transcription," Biochem. J. 319: 241-248 (1996).
Ho et al., "Site-directed mutagenesis by overlap extension using the polymerase chain reaction," Gene 77:51-59 (1989).
Houdebine, L.M. and D. Chourrout, "Transgenesis in fish," Experientia 47: 891-897 (1991).
Hu et al., "Transdifferentiation of myoblasts by the adipogenic transcription factors PPARγ and c/EBPα ," Proc. Natl. Acad. Sci. U.S.A. 92: 9856-9860 (1995).
Hulin et al., "The glitazone family antidiabetic agents," Current Pharmaceutical Design 2: 85-102 (1996).
Isseman, I. and S. Green, "Activation of a member of the steroid hormone receptor superfamily by peroxisome proliferators," Nature 347:645-650 (1990).
Joyner et al., "Production of a mutation in mouse *En-2* gene by homologous recombination in embryonic stem cells," Nature 338:153-156 (1989).
Kim, J. B., and B.M. Spiegelman, "ADD1/SREBP1 promotes adipocyte differentiation and gene expression linked to fatty acid metabolism," Genes & Development 10: 1096-1107 (1996).
Négrel et al., "Prostacyclin as a potent effector of adipose-cell differentiation," Biochem. J. 257: 399-405 (1989).
Osborne et al., "5' end of HMG CoA reductase gene contains sequences responsible for cholesterol-mediated inhibition of transcription," Cell 42:203- 212 (1985).
Osumi et al., "Two *cis* -acting regulatory sequences in the peroxisome proliferators-reponsive enhancer region of rat acyl-CoA oxidase gene," Biophys. Res. Commun. 175:866-871 (1991).
Oxender et al., "Attentuation in the *Escherichia coli* tryptophan operon: Role of RNA secondary structure involving the tryptophan codon region," Proc. Natl. Acad. Sci. USA 76:5524-5528 (1979).
Price et al., "Lineage analysis in the vertebrate nervous system by retrovirus-mediated gene transfer," Proc. Natl. Acad. Sci. USA 84:156-160 (1987).
Pursel et al., "Genetic engineering of livestock," Science 244:1281-1288 (1989).
Quantin et al., "Adenovirus as an expression vector in muscle cells *in vivo*," Proc. Natl. Acad. Sci. USA 89:2581-2584 (1992).
Quon et al., "Transfection of DNA into isolated rat adipose cells by electroporation," Biochem. Biophys. Res. Comm. 194: 338-346 (1993).
Ren et al., "Peroxisome proliferators-activated receptor α inhibits hepatic S14 gene transcription," J. Biol.Chem.271: 17167-17173 (1996).
Ricote et al., "Expression of the peroxisome proliferators-activated receptor γ (PPARγ) in human atherosclerosis and regulation in macrophages by colony stimulating factors and oxidized low density lipoprotien," Proc Natl Acad Sci USA 95(13): 7614-7619 (1988).
Sakai et al., "Sterol-regulated release of SREBP-2 from cell membranes requires two sequential cleavages, one within a transmembrane segment," Cell 85: 1037-1046 (1996).
Saladin et al., "Differential regulation of peroxisome proliferator activated receptor γ1 (PPARγ1) and PPARγ2 messenger RNA expression in the early stages of adipogenesis," Cell Growth Differ. 10(1):43-48 (1999).
Saladin et al., "Regulation of *ob* gene expression in rodents and human," Horm. Metab. Res. 28(12): 638-641 (1996).
Saladin et al., "Transient increase in *obese* gene expression after food intake or insulin administration," Nature 377: 527-529 (1995).
Saltiel, A. R. and J.M. Olefsky, "Thiazolidinediones in the treatment of insulin resistance and type II diabetes," Diabetes 45: 1661-1669 (1996).
Schmidt et al., "Identification of a new member of the steroid hormone receptor superfamily that is activated by a peroxisome proliferators and fatty acids," Mol. Endocrinol. 6:1634-1641 (1992).
Schoonjans et al., "Induction of LPL gene expression by sterols is mediated by a sterol regulatory element and is independent of the presence of multiple E boxes," J Mol Biol. 304(3):323-34 (2000).
Schoonjans et al., "Role of the peroxisome proliferators-activated receptor (PPAR) in mediating the effects of fibrates and fatty acids on gene expression," J. Lipid Res. 37: 907-925 (1996).
Schoonjans et al., "PPARα and PPARγ activators direct a distinct tissue-specific transcriptional response via a PPRE in the lipoprotein lipase gene," The EMBO Journal 15: 5336-5348 (1996).
Schoonjans et al., "Acyl-CoA synthetase mRNA expression is controlled byfibric-acid derivatives, feeding and liver proliferation," Eur. J. Biochem. 216: 615-622 (1993).
Schoonjans et al., "Induction of the acyl-coenzyme A synthetase gene by fibrates and fatty acids is mediated by a peroxisome proliferators response element in the C promoter," J. Biol. Chem. 270: 19269-19276 (1995).
Schoonjans et al., "The peroxisome proliferator activated receptors (PPARs) and their effects on lipid metabolism and adipocyte differentiation," Biochem. Biophys. Acta. 1302: 93-109 (1996).
Sher et al., "cDNA cloning, chromosomal mapping, and functional characterization of the human peroxisome proliferators activated receptor," Biochemistry 32:5598-5604 (1993).

Shimomura et al., "Cholesterol feeding reduces nuclear forms of sterol regulatory element binding proteins in hamster liver," Proc. Natl. Acad. Sci. USA 94:12345-12359 (1997).
Shuman, R.M., "Production of transgenic birds," Experientia 47: 897-905 (1991).
Simons et al., "Gene transfer into sheep," Bio/Technology 6:179-183 (1988).
Smith et al., "Multiple Sterol Regulatory Elements in Promoter for Hamster 3-Hydroxy-3-methyglutaryl-conenzyme A synthase," J. Biol. Chem. 263:18480-18487 (1988).
Spiegelman, B.M. and J.S. Flier, "Adipogenesis and obesity rounding out the big picture," Cell 87: 377-389 (1996).
Stenson et al., "Dietary Supplementation with fish oil in ulcerative colitis," Annals of Internal Medicine 116:609-614 (1992).
Stratford Perricaudet et al., "Widespread long-term gene transfer to mouse skeletal muscles and heart," J. Clin. Invest. 90:626-630 (1992).
Tontonoz et al., "PPARγ Promotes Monocyte/Macrophage Differentiation and Uptake of Oxidized LDL," Cell 93(2):241-252 (1988).
Tontonoz et al., "Stimulation of Adipogenesis in Fibroblasts by PPARγ2, a Lipid-Activated Transcription Factor," Cell 79: 1147-1156 (1994).
Tontonoz et al., "PPARγ2 reduces adipose expression of the phosphoenolpyruvate carboxykinase gene," Mol. Cell. Biol. 15: 351-357 (1995).
Tontonoz et al., "mPPArγ2: tissue-specific regulator of an adipocyte enhancer," Genes & Development. 8(10): 1224-1234 (1994).
Tontonoz et al., "ADD1: a Novel Helix-Loop-Helix Transcription Factor Associated with Adipocyte Determination and Differentiation," Mol. Cell. Biol. 13: 4753-4759 (1993).
Tugwood et al., "The mouse peroxisome proliferators activated receptor recognizes a response element in the 5' flanking sequence of the rat acyl CoA oxidase gene," EMBO J. 11: 433-439 (1992).
Vidal et al., "The expression of ob gene is not acutely regulated by insulin and fasting in human abdominal subcutaneous adipose tissue," J. Clin. Invest. 98: 251-255 (1996).
Vu-Dac et al., "Fibrates increases human apolipoprotein A-II expression through activation of the peroxisome proliferators-activated receptor," J. Clin. Invest. 96: 741-750 (1995).
Wang et al., "SREBP-1, a membrane-bound transcription factor released by sterol-regulated proteolysis," Cell 77:53-62 (1994).
Willson et al., "The Structure-Activity Relationship between peroxisome proliferators-activated receptor γ agonism and the antihyperglycemic activity of thiazolidinediones," J. Med. Chem. 39: 665-668 (1996).
Wu et al., "Receptor-mediated gene delivery *in vivo*, partial correction of genetic analbuminemia in nagase rats" Journal of Biological Chemistry 266:14338-14342 (1991).
Wu et al., "Induction of peroxisome proliferator-activated receptor γ during the conversion of 3T3 fibroblasts into adipocytes is mediated by C/EBPβ, C/EBPδ, and glucocorticoids," Mol.Cell. Biol. 16(8): 4128-4136 (1996).
Wu et al., "Conditional ectopic expression of C/EBPβ in N1H-3T3 cells induces PPARγ and stimulates adipogenesis," Genes & Development 9: 2350-2363 (1995).
Xue et al., "Distinct Stages in Adipogenesis Revealed by Retinoid Inhibition of Differentiation after Induction of PPARγ," Mol. Cell. Biol. 16: 1567-1575 (1996).
Yang et al., "*In vivo* and *in vitro* gene transfer to mammalian somatic cells by particle bombardment," Proc. Natl. Acad. Sci. U.S.A. 87:9568-9572 (1990).
Yanofsy, C., "Attenuation in the control of expression of bacterial operons," Nature 289:751-758 (1981).
Yeh et al., "Cascade regulation of terminal adipocyte differentiation by three members of the C/EBP family of leucine zipper proteins," Genes & Development 9: 168-181 (1995).
Yokoyama et al., "SREBP-1, a Basic-Helix-Loop-Helix-Leucine Zipper Protein that Controls Transcription of the Low Density Lipoprotein Receptor Gene," Cell 75:187-197 (1993).
Zhu et al., "Structural organization of mouse peroxisome proliferators-activated receptor γ (mPPARγ) gene: Alternative promoter use and different splicing yield two mPPARγ isoforms," Proc. Natl. Acad. Sci. U.S.A. 92: 7921-7925 (1995).
Kliewer et al., "Differential expression and activation of a family of murine peroxisome proliferators-activated receptors," Proc. Natl. Acad. Sci. USA 91 : 7355-7359 (1994).
Kliewer et al., "A prostaglandin J, metabolite binds peroxisome proliferators-activated receptor γ and promotes adipocyte differentiation," Cell 83: 813-819 (1995).
Lambe, K.G. and J.D. Tugwood, "A human peroxisome-proliferator-activated receptor-γ is activated by inducers of adipogenesis, including thiazolidinedione drugs," Eur. J. Biochem. 239: 1-7 (1996).
Lefebvre et al., "Regulation of lipoprotein metabolism by thiazolidinediones occurs through a distinct but complementary mechanism relative to fibrates," Arterioscler. Thromb. Vasc. Biol. 17(9):1756-1764 (1997).
Le Gal La Salle et al., "An adenovirus vector for gene transfer into neurons and glia in the brain," Science 259: 988-990 (1993).
Lehmann et al., "An antidiabetic thiazolidinedione is a high affinity ligand for Peroxisome Proliferator-Activated Receptor γ (PPARγ)," J. Biol. Chem. 270: 12953-12956 (1995).
Leid et al., "Purification, cloning, and RXR identity of the HeLa cell factor with which RAR or TR heterodimerizes to bind target sequences efficiently," Cell 68: 377-395 (1992).
Lemberger et al., "Expression of the peroxisome proliferators-activated receptor α gene is stimulated by stress and follows a diurnal rhythm," J. Biol. Chem. 271:1764-1769 (1995).
Lin F. and M.D. Lane, "Antisense CCAAT/enhancer-binding protein RNA suppresses coordinate gene expression and triglyceride accumulation during differentiation of 3T3-L1 preadipocytes," Genes & Development 6:533-544 (1992).
Mansén et al., "Expression of the peroxisome proliferators-activated receptor (PPAR) in the mouse colonic mucosa," Biochem. Biophys. Res. Commun. 222: 844-851 (1996).
Marcus-Sekura, C.J., "Techniques for using antisense oligodeoxyribonucleotides to study gene expression," Anal. Biochem. 172:289-295 (1988).
Miard et al., "Atypical transcriptional regulators and cofactors of PPARγ," Int. J. Obes. Relat. Metab. Disord. 29(Suppl 1):S10-S12 (2005).
Miller et al., "The adipocyte specific transcription factor C/EBPα modulates human *ob* gene expression," Proc. Natl. Acad. Sci. U S A. 93(11):5507-5511 (1996).
Miller et al., "Human gene therapy comes of age," Nature 357:455-460 (1992).
Moller, D. E., and J.S. Flier, "Insulin resistance-mechanisms, syndromes, and implications," New England Journal of Medicine 325: 938-948 (1991).
Mukherjee et al., "Identification, characterization, and tissue distribution of human Peroxisome Proliferator-Activated Receptor (PPAR) isoforms PPARγ2 versus PPARγ1 and activation with Retinoid X Receptor Agonists and Antagonists," J. Biol. Chem. 272: 8071-8076 (1997).
Mukherjee et al., "Human and rat peroxisome proliferators activated receptors (PPARs) demonstrate similiar tissue distribution to PPAR activators," J. Steroid Biochem. 51(3/4): 157-166 (1994).
Mulligan, R.C., "The basic science of gene therapy," Science 260:926-931 (1993).
Naggy et al., "Oxidized LDL regulates macrophage gene expression through ligand activation of PPARγ," Cell 93(2):229-240 (1988).

γ1 acccccacccccacccccagccggcgcccgcgcc cgcccccgcgccgggcccggctcggcccgacccg gatccgccgcgggcaggcggggcccagcgcactc ggagcccgagcccgagccgcagccgccgcctggg

LF-2 gcgcttgggtcggcctcgaggacaccggagaggg gcgccacgccgccgtggccgcagaaATG

*Fig. 1A*

γ2 gtcctttctgtgtttattcccatctctcccaaat atttggaaactgatgtcttgactcatgggtgtat tcacgattctgttacttcaagtctttttcttta acggattgatcttttgctagatagagacaaaata

LF-35 tcagtgtgaattacagcaaacccatattccatgc tgttATG

*Fig. 1B*

FIGURE 4

```
gagaatacag gcacatgcca ccatgcccag ctaatttttc tgttttttgt agagacagga 60
tttcgctgtg gtgctcaggc tggtctccaa ctcctgggct caagcaatcc gcctgcctca 120
gccttccaaa gtgaaaaggt tttctctcat ttttcaaata gaagtactaa acaatgccag 180
agaaataaat aaacaggcaa aatacgttgg ctatagttta tattatttcc tgctacagtt 240
aacaaaatgg gaagacattt tatcttcatg gtctactaca tttatgccat gtgttaagta 300
ataaaatagc ttttgtaaat tataaattaa aaggtacaga tttaaaagag aaaatactgt 360
agagttttca tgtaggtaag actgtgtaga atgtcgggtc tcgatgttgg cgctattcaa 420
gccctgatga taaggctttt ggcattagat gctgttttgt cttcatggaa aatacagcta 480
ttctaggatc cttgagcctt tcataagaga taaggttgtg aatcctaaga ccctaggacc 540
atttacttag atgatctgct ctctggttcg tcctctgaaa agtctgcttc gtgaggggtg 600
tgctgcattt gccttgccta agtggtgtgg cacacaactg tactgtcacc ttaggcttaa 660
taaccatgtg tcatctagaa tgaagttata ttttaaaaag gatcgttttt gccatgtata 720
aattttcaaa cattaacttt cagggttatt aatcctttta aggtctagtt tttcttaagt 780
ctgtgcagta atagaggtat cgtcattcat gtgacataaa agatggaaag gggcttcatt 840
                         ADD1/SREBP1 Site
catgttagtg atggaaatag gaaagtaggt gaagtgattt taatagatgt ttcttttatg 900
aaataatttt taaaagattg tccagccctg catgatttat gatgaatcat tttgtggtct 960
gttagttact tttagagaat agaaagcatt gtaggctcag ggaaagcaaa cattcagaat 1020
gaaatccaat agagaaggta aatttatttg ggcatgtaca ttttggcagc ctaggctgtg 1080
   C/EBP Site
tacatgtgta cacattctga acatgtgtgt atattgaaaa tcttgtctct tttttattgt 1140
                              TATA Box
taagA*TTTGA AAGAAGCCGA CACTAAACCA CCAATATACA ACAAGGCCAT TTTCTCAAAC 1200
                                                          <---
GAGAGTCAGC CTTTAACGgt aagtaaaatc agaatttata ctgcatttgt attgaaaagt 1260
------------------
LF-60 Oligo
atccctttta aagaatatgt aaattataca ttgttatttt attgtaaaat ttcctagaga 1320
gtgatttttg actattataa tactttctgc tatataattt tccagtcagt tggactatgc 1380
agtgtaacat atttgtctaa cacaaaacaa aggtaagata ggaaaatgac ctagaagttg 1440
agaaataact caaatcctta aaa                                         1433
```

FIGURE 5

```
cccctgcccc tgcccctgcc cccaccccca cccccacccc cacccccagc cggcgcccgc 60
                   CACC Box
gcccgccccc gcgccgggcc cggctcggcc cgacccggtt ccgccgcggg caggcggggc 120
    Sp1 site
ccagcG*CACT CGGAGCCCGA GCCCGAGCCG CAGCCGCCGC CTGGGGCGCT TGGGTCGGCC 180
TCGAGGACAC CGGAGAGGGG CGCCACGCCG CCGTGGCCGC Aggtcagagt acgggtgccc 240
gcggcgctcg ggaaccggct gctgcctggg cggggagtgc tcagggaggg ggcgcggagg 300
gctggggccg agggtctggg gggtagggcc gaggaaacgg caactgacgg ggtcccagac 360
ggatgagagc tggggagaag ggggtctcgg ctgaggggtc cggggctgag gcacggtcat 420
ggtccggcag gacccggact gacgggtctc gggcgggcgg ctcacgggtg accgggtgaa 480
tgggtctcgg gctgacggca ccc                                        503
```

FIGURE 6

```
ggagctccac gcggtggcgg ccgctctaga actagtggat cccccgggct gcaggaattc 60
gaggctgcag tgaactatga ttgcaccact gcactccagc ctgggtgaga gagcaatacc 120
ttgtctcaaa acaaacaaac aaacaaaacc ccatgagata tcacttcata ccctttaggt 180
tggctaaaat aaaaaagact ataacaagtg ttgacaagga tgtggaaaaa ctggaaccct 240
gacacattgc tggtgggatt gtaaaatggt gtgcccactt tggaaaacag actggcagtt 300
cctcaaaaac accgagttac gttatgatcc tgcagttctg tccctaggta tatactcaag 360
agaaataaaa atatatgtcc acaagtaacc ttgtacatga atgctcacag cagcattatt 420
cataatagcc cataaaagta gaaacaacct aaatattcat caattcatgg gatgaataaa 480
caaaatgtgg tatatgtgta taatggaata ttgaccataa aaaggaatga aatattaata 540
taagctataa catggatgag cctccacaaa tactatgcta agtgaaagaa gaaagtcaca 600
aaggacttca tattctatga ttctatttat atgaattgtc cagaataggt aaatctatag 660
agaaagaata tctctatcta gagttggtgg aatgactgtt aatggagagg gggttccttt 720
ttggagtgat gaaaatgttc taagggtaga tttggtgatg atggcacaac tctgtcaata 780
aactaaaact cattgaactg tacattttat ttatttattt ttgagatgga gtcttgctct 840
ggggctgaag tgcagtggcg caatctcggc ttgtaacctc tgcctcccag ggtcaagcga 900
ttctactgcc tcagcccccc gagtagctga gattacaggc acgtgccacc acgcccagct 960
aatttttgta tttcttagta gagatggagt ttcaccatgt tggccaggct ggtcttgaac 1020
tcccggcctc aagtgatcca cctgcctcgg cctcccaaag tgctgggatt acaggcgtga 1080
gctgccatac ccggcctgaa ttgtacattt tacttctatg gtatttacat tttagattat 1140
attaattatt cctcaataaa gctgtgattt taaaaagcag gctaggcgca gtggctggtg 1200
cctataatcc cagcactttg gaaagctgag gcaggaggat cacttgagcc caggagtttc 1260
agactagtct aggcaacatg tcaagacaca gtctctacta aacaattaaa attaaaaaaa 1320
aaaattagcc aggcatggtg gtgtgcacct gtagtcccag ctacttggga gcctggggtg 1380
ggaggattcc ttgagcccgg gaagtcgagg ctgaagtgag ccgtgattgc gccacagcac 1440
tccagcctgg gcgacacagc aacaccctgt ctcatggaag aaagaaagaa aagaaaggaa 1500
gaaagaaaaa aaaaaagcag attggaactc tggaattaac aagaagtagg acgcacggag 1560
cacttccgcc tgagtggaga ctgtggatcc gggtcaacct gactacctaa atcacaggcc 1620
aataaatggt ctttcagtgg tcagtccctg taagatccgt ggctctcagc ttcttatctt 1680
aggggctgtg gaggaaggac atgattatgt tgatttaagc gctgaatatt ttcccttgtg 1740
atacccatcc tcgcaaaact ttgcttcaac cacaaacgag gaccttctgt accagagggg 1800
caataacaca atgaagctag gaagaaatgc agagcacccc agcatacagt ccataagctt 1860
cctgaagtgg ggggcctcag gcatcgctgc ctccccaaag aggatcaggc ccagaacagt 1920
atgctccaga aataagactg gaaaaaggga aagaggggcc tcaagtccag gagaccagcg 1980
gctttctgaa cgcgcacctg ccaacccact ttggacaggt cacgatggac agcgtggcag 2040
gaaaagaaaa ggtcactgtc tacccaacac atgagaaact gtttctcgtg cctcacgtcc 2100
ccactccgtc cccacccatg ttgtctgagt ccctcggtgt cagaaacact gctaagaaat 2160
ttaagaaatt ctgttaatga gtttaagaaa tgtttttaat gattaaaagt cagtgacttg 2220
tgaataacca tgtaacttac aaacgcaagg aactctgaaa gtgtgcagca ccaccgatca 2280
gaagagaaaa ccaagggacc cgaaatatgc tttaattaaa ttttctttta aaatgtcact 2340
ggaaagaaca tcttgggaag acggcctggc cgatcgccgt gtgaagggca agccactctg 2400
gccgagaggg agccccacac ctcggtctcc ccagaccggc cctggccggg ggcatccccc 2460
taaacttcgg atccctcctc ggaaatggga ccctctctgg gccgcctccc agcggtggtg 2520
gcgaggagca aacgacacca ggtagctgcc gcgggggcaga gagtggacgc gggaaagccg 2580
gtggctcccg ccgtgggccc tactgtgcgc gggcggcggc cgagcccggg ccgctccctc 2640
ccagtcgcgc gccgccgccc gcgccctgtt tgggttcatg gggggtg 2688
```

FIGURE 7

```
gaattcaact gaatatagag aaaactaatt ttacacaact gtaatcactg tagtcatttg 60
gacaaattag caaacccaag ttttgcttta acttggattg ccttaataaa gatgttttgg 120
ggcttaatgg cacagttgct caactccccc actttattcc gtgatgttca gacccagcca 180
gcatttcccc atcaggctct tgcaccatga ttgacaggga cacttttact agtccccttg 240
aagaatgaat agttactcaa tggagattaa ccagatatat atttatttta ctcagaatat 300
cacgataagt ataattcaga gaattattgc cttctaatat actgccctgt gtgggggcgt 360
ctttgaaagt ccgcaaagtc actgcaattc taataggcca ctcatgtgac aagacctgct 420
cccacatcgg taatttggca cagctagtat ttctccttgc caaaaagggc aaaggccttg 480
agcaagaagc cagctttttc ctgattacaa aactgaccac aattcctcgc caacctaaca 540
gcgtaagtct atttttttct ggtggtgtgt tattcttctc atagagaact ccattttttc 600
attatgacat agcacttatc gtttaaacat caattgatgt tcaaacatca gctggtgtaa 660
cattgctgca gttgctattg atggataagc tgaagttttt aagaaagcaa acccgatgta 720
taaaattgaa accagatcaa acccttcttc attctcagct atttaatttt acagaattta 780
gatagcagtc agtatcattt tgggcttcac aaatcagtag agtaagtacc ttaggaatat 840
aacatttcag tagcatgctg ataccaacgt ttaaactatg gatacatatt tgaattccaa 900
atttttcttc agataatgtg attagagatt agagattcaa ccagggatag acaccgaaag 960
aaaactttgc ccaaataagc tttctggtat ttcataagca agagatttaa gttttccatt 1020
taagaagcca ttgtgaatta tacaacaata aaaaatgcaa gtggatattg aacagtctct 1080
tctctgataa ttctaaatac agtacagttc acgcccctca cgagacactg aacatgtggt 1140
caccggcgag acagtgtggc aatattatcc ctgtaatgta ccaagtcttg ccagagcagt 1200
gaacattatg acacaacttt ttgtcacagc tggctcctaa taggacagtg ccagccaatt 1260
                                                      TATA like Box
caagcccagt cctttctgtg tttattccca tctctcccaa atatttggaa actgatgtct 1320
                                       C/EBP Site
T*GACTCATGG GTGTATTCAC GATTCTGTTA CTTCAAGTCT TTTTCTTTTA ACGGATTGAT 1380
AP-1 Site
CTTTTGCTAG ATAGAGACAA AATATCAGTG TGAATTACAG CAAACCCATA TTCCATGCTG 1440
TTATGGGTGA AACTCTGGGA GATTCTCCTA TTGACCCAGA AAGCGATTCC TTCACTGATA 1500
  Met
CACTGTCTGC AAACATATCA CAAGgtaaag ttccttccag atacggctat tggggacgtg 1560
ggggcattta tgtaagggta aaattgctct tgtagtttgt cttccaggtt gtgtttgttt 1620
taatactatc atgtgtacac tccagtattt taatgcttag ctcgttgcta tcgcgttcat 1680
ttaaaaacat gttcagaacc ttaaaaaagg aaacctaacc taatctatct tatctctgtg 1740
catggctccc atttcctgaa ttttaagcat taaaggtata gttatatcca aaaacaatcc 1800
tgttcatctt tatttcctga gtttgcatag atttcccaag aatacataat ggctttttag 1860
acttgaaggg tcacttttcc tctttcatct catatgttag agatctctca taactgtgtt 1920
atccctcttg cagcactttt attcctcttg aatacctcag ctcttttctg ttctattttg 1980
aaatctaagt atgtgtgtgc acttcagctc tcccaaagaa tgtatatccc acaatgtagg 2040
acaag                                                             2045
```

HUMAN PEROXISOME PROLIFERATOR ACTIVATED RECEPTOR GAMMA (PPARγ) GENE REGULATORY SEQUENCES AND USES THEREFOR

PRIORITY CLAIM

This application claims priority to Provisional Application Ser. No. 60/053,692, filed Jul. 25, 1997 and is incorporated by reference in its entirety.

I. FIELD OF THE INVENTION

This invention relates to DNA sequences that regulate expression of human peroxisome proliferator activated receptor (PPAR) genes, particularly PPARγ genes. This invention further relates to methods for identifying agents useful for treatment of diseases and pathological conditions affected by PPAR, and agents and compositions identified using such screening method.

II. BACKGROUND OF THE INVENTION

Peroxisome proliferator activated receptors (PPARs) constitute a subfamily of the nuclear hormone receptors. Three distinct PPARs, termed α, δ (also called β, NUC-1 or FAAR) and γ, each encoded by a separate gene and showing a distinct tissue distribution pattern, have been described [Reviews: Desvergne, B. and Wahli, W., *Birkhauser.* 1: 142–176 (1994); Green, S., *Mutation Res.* 333: 101–109 (1995); Schoonjans, K. et al., *Biochem. Biophys. Acta.* 1302: 93–109 (1996); Schoonjans, K. et al., *J. Lipid Res.* 37: 907–925 (1996)]. Although it was known that PPARs are activated by a wide variety of chemicals including fibrates, phthalates and fatty acids, PPARs were initially considered orphan receptors, since no direct binding of these compounds to the receptors could be demonstrated.

Activated PPARs heterodimerize with retinoid X receptors (RXRs), another subfamily of nuclear hormone receptors, and alter the transcription of target genes after binding to PPAR response elements (PPREs). A PPRE typically contains a direct repeat of the nuclear receptor hexameric DNA core recognition motif, an arrangement termed DR-1 when recognition motifs are spaced by 1 nucleotide [Schoonjans, K. et al., *J. Lipid Res.* 37: 907–925 (1996)].

Recently, ligands that induce the transcriptional activity of PPARα (fibrates and leukotriene B4) and γ (prostaglandin J derivatives and thiazolidinediones) have been identified [Devchand, P. R. et al., *Nature* 384: 39–43 (1996); Kliewer, S. A. et al., *Cell* 83: 813–819 (1995); Forman, B. M. et al., *Cell* 83: 803–812 (1995); Lehmann, J. M. et al., *J. Biol. Chem.* 270: 12953–12956 (1995)].

Numerous PPAR target genes have been identified so far [Review: Schoonjans, K. et al., *Biochem. Biophys. Acta.* 1302: 93–109 (1996)], and additional target genes continue to be identified [Hertz, R. et al., *Biochem. J.* 319: 241–248 (1996); Ren, B. et al., *J. Biol. Chem.* 271: 17167–17173 (1996)]. Because they are activated by various fatty acid metabolites as well as several drugs used in the treatment of metabolic disorders, PPARs are key messengers responsible for the translation of nutritional, pharmacological and metabolic stimuli into changes in gene expression.

PPARγ was the first PPAR for which ligands were identified. In rodents, PPARγ was thought to be confined to adipose tissue. However, low levels of PPARγ expression were detected in other tissues. This led to the suggestion that PPARγ is a key factor triggering adipocyte differentiation, a hypothesis later confirmed [Spiegelman, B. M. and Flier, J. S., *Cell* 87: 377–389 (1996)]. It is now known that several transcription factors including the nuclear receptor PPARγ (6, 7), the family of CCAATT enhancer binding proteins (C/EBP)1 (8–13) and the basic helix-loop-helix leucine zipper transcription factor ADD1/SREBP1 (14, 15) orchestrate the adipocyte differentiation process (for reviews, see Refs. 1, 3, 16–18).

Two isoforms of PPARγ (PPARγ1 and PPARγ2 that differ by an extra 30 amino acids at the N-terminus) have been identified in mice (Tontonoz, et al. *Genes & Development* 8:1224–1234 (1994)). Two forms of human PPARγ, γ1 and γ2, have been identified; PPARγ1 has been shown to be the most common form in humans [Mukherjee, R. et al., *J. Biol. Chem.* 272: 8071–8076 (1997)]. PPARγ2 is expressed at high levels specifically in adipose tissue and is induced early in the course of differentiation of 3T3-L1 preadipocytes to adipocytes. Overexpression and activation of PPARγ protein stimulates adipose conversion in cultured fibroblasts (Tontonoz, et al. *Cell* 79:1147–1156 (1994)). In addition, PPARγ together with C/EBPα can induce transdifferentiation of myoblasts into adipocytes (19). Activation of PPARγ is sufficient to turn on the entire program of adipocyte differentiation (Lehmann, et al. *J. Biol. Chemistry* 270:12953–12956 (1995)).

PPREs have been identified in several genes that play crucial roles in adipocyte differentiation, most of them affecting lipid storage and control of metabolism. Examples are fatty acid binding protein (aP2) [Tontonoz, P. et al., *Genes Dev.* 8: 1224–1234 (1994)], phosphoenolpyruvate carboxykinase (PEPCK) [Tontonoz, P. et al., *Mol. Cell. Biol;* 15: 351–357 (1995)], Acyl CoA Synthase (ACS) [Schoonjans, K. et al., *Eur. J. Biochem.* 216: 615–622 (1993); Schoonjans, K. et al., *J. Biol. Chem.* 270: 19269–19276 (1995)], and lipoprotein lipase (LPL) [Schoonjans, K. et al., *EMBO J.* 15: 5336–5348 (1996)], all of which are regulated by PPARγ.

Recently, prostaglandin J2 (PGJ2) was shown to be a naturally occurring ligand [Forman, B. M. et al., *Cell* 83: 803–812 (1995); Kliewer, S. A. et al., *Cell* 83: 813–819 (1995)] and the anti-diabetic thiazolidinediones (TZDs) [Forman, B. M. et al., *Cell* 83: 803–812 (1995); Lehmann, J. M. et al., *J. Biol. Chem.* 270: 12953–12956 (1995)] were shown to be synthetic ligands for PPARγ. The identification of PGJ2 and TZDs as PPARγ ligands corroborates the earlier observation that both prostanoids and TZDs are potent inducers of adipose differentiation programs [Gaillard, D. et al., *Biochem. J.* 257: 389–397 (1989); Negrel, R. et al., *Biochem. J.* 257: 399–405 (1989); Forman, B. M. et al., *Cell* 83: 803–812 (1995); Kliewer, S. A. et al., *Cell* 83: 813–819 (1995); Aubert, J. et al., *FEBS Lett.* 397: 117–121 (1996)]. TZDs are currently being developed as insulin sensitizers for the treatment of non-insulin dependent diabetes mellitus (NIDDM) [Reviews: Hulin, B. et al., *Current Pharm. Design* 2: 85–102 (1996); Saltiel, A. R. and Olefsky, J. M., *Diabetes* 45: 1661–1669 (1996)]. Interestingly, their relative potency to activate PPARγ in vitro correlates well with their anti-diabetic potency in vivo, suggesting that PPARγ mediates their anti-diabetic effect [Berger, J. et al., *Endocrinology* 137: 4189–4195 (1996); Willson, T. M. et al., *J. Med. Chem.* 39: 665–668 (1996)]. These observations define the role of PPARγ in adipose differentiation and a role in glucose and lipid metabolism.

Although many PPARs have been isolated and their cDNAs have been cloned from various species (International Patent publication nos. WO 96/23884, WO96/01430, WO95/11974, Elbrecht, A. et al., *Biochem. Biophys. Res.*

*Comm.* 224: 431–437 (1996), Greene, M. E. et al., *Gene Expression* 4: 281–299 (1995), Aperlo, C. et al., *Gene* 162: 297–302 (1995), Sher, T. et al., *Biochemistry* 32: 5598–5604 (1993), Isseman, et al. *Nature* 347:645–650 (1990); Dreyer, et al., *Cell* 68:879–887 (1992); Gottlicher, et al *Proc. Natl. Acad. Sci. USA*. 89:4653–4657 (1992); Sher, et al. *Biochemistry* 32:5598–5604 (1993); and Schmidt, et al. *Mol. Endo-crinoL* 6:1634–16414–8 (1992); Tontonoz, et al. *Genes & Development* 8:1224–1234 (1994); Kliewer, et al. *Proc. Nail. Acad. Sci.* 91:7355–7359 (1994); Chen, et al. *Biochem. and Biophy. Res. Com.* 196:671–677 (1993)), information regarding the regulation of PPAR expression is very limited (see, e.g. Wu, Z. et al., *Mol. Cell. Biol.* 16(8): 4128–4136 (1996), Zhu, Y. et al., *Proc. Natl. Acad. Sci. USA* 92: 7921–7925 (1995), Mukherjee, R. et al., *J. Steroid Biochem.* 51(3/4): 157–166 (1994)). In particular, the regulatory regions controlling the expression of the human PPARγ genes have not yet been disclosed.

III. SUMMARY OF THE INVENTION

The present invention is related to the isolation, cloning and identification of the promoters and other regulatory elements of the PPARγ gene and the use of PPARγ gene control regions to screen for agents that modulate PPARγ gene expression and thence use these modulators as lead compounds to design or search for other drugs to treat disease related to the level of PPARγ gene expression. The isolated PPARγ gene control regions have utility in constructing in vitro and in vivo experimental models for studying the modulation of PPARγ gene expression and assaying for modulators of PPARγ gene expression. Such experimental models make it possible to screen large collections of natural, semisynthetic, or synthetic compounds for therapeutic agents that affect PPARγ gene expression.

Thus, in one aspect, the present invention is directed to an isolated, purified, enriched or recombinant nucleic acid containing a control region of a human PPARγ gene.

By "control region" is meant a nucleic acid sequence capable of, required for, assisting or impeding initiating, terminating, or otherwise regulating the transcription of a gene, including, but not limited to, promoter, enhancer, silencer and other regulatory elements (e.g. those regulating pausing or anti-termination). A positive transcription element increases the transcription of the PPARγ gene. A negative transcription element decreases the transcription of the PPARγ gene. A control region also includes nucleic acid sequences that, although insufficient to initiate, terminate, or otherwise regulate the transcription of human PPARγ gene by themselves, are capable of doing so in combination or coordination with other nucleic acid sequences. A control region can be in nontranscribed regions of a gene, introns or exons. A control region can be in the 5' upstream region or the 3' downstream region to the amino acid coding sequence. A control sequence can be a single regulatory element from a gene. A control region can also have several regulatory elements from a gene linked together. These several regulatory elements can be linked in a way that is substantially the same as in nature or in an artificial way.

A control region in introns and exons may also be involved with regulating the translation of a PPARγ protein, e.g. splicing, processing heteronuclear ribonucleoprotein particles, translation initiation and others described in Oxender, et al. *Proc. Natl. Acad. Sci. USA* 76:5524 (1979) and Yanofsy, *Nature* 289:751–758, (1981).

A control region of this invention is isolated or cloned from the human PPARγ gene. It is distinguished from control regions disclosed in the prior art in that it contains a regulatory element of novel or unique nucleic acid sequence for the human PPARγ gene, a known regulatory element set in a novel or unique nucleic acid sequence context for the human PPARγ gene, or a few known regulatory elements linked in a novel or unique way for the human PPARγ gene. The human PPARγ gene control regions include what is in plasmids PPAC8856 and PPARγ1 promoter-luc, both of which are deposited at ATCC with accession numbers 97906 and 97862, respectively. The human PPARγ gene control regions also include what are in plasmids pGL3γ1p3000, pGL3γ2p1000 and pGL3γ3p800. The control region in pGL3γ1p3000 starts at the 5' end at nt 2 of SEQ ID NO: 2 and ends at the 3' end, immediately before the reporter gene, at nt 185 of SEQ ID NO: 1. The control region in pGL3γ2p1000 starts at the 5' end at nt 399 of SEQ ID NO: 3 and ends at the 3' end, immediately before the reporter gene, at nt 1438 of SEQ ID NO: 3. The control region in pGL3γ3p800 starts at the 5' end at nt 368 of SEQ ID NO: 34 and ends at the 3' end, immediately before the reporter gene, at nt 1218 of SEQ ID NO: 34.

Preferably, the control region is selected from one of the following regions:

the 1 kb fragment 5' upstream of the transcription initiation site of the human PPARγ1 gene, exon A1, intron A1, the 800 nt 5' upstream of the transcription initiation site of the human PPARγ3 gene, exon A2, intron A2, the 500 nt 5' upstream of the transcription initiation site of the human PPARγ2 gene, exon B, and intron B.

A nucleic acid of this invention can be single stranded or double stranded, DNA or RNA, including those containing modified nucleotides known to one skilled in the art. The complementary strand of an identified sequence is contemplated herein.

In a preferred embodiment, the nucleic acid contains a control region and an amino acid coding region of the human PPARγ gene, e.g., one or more of exons 1, 2, 3, 4, 5 and 6 of the human PPARγ gene. In a more preferred embodiment, the nucleic acid contains the entire coding region of human PPARγ gene.

In another preferred embodiment, the nucleic acid does not contain one or more of exons 1, 2, 3, 4, 5 and 6 of the human PPARγ gene. In a more preferred embodiment, the nucleic acid does not contain any one of exons 1, 2, 3, 4, 5 and 6 of the human PPARγ gene.

In another preferred embodiment, the nucleic acid contains a fragment listed in the following Table III:

| Nucleic acid fragment | SEQ ID NO: | Human PPARγ gene |
|---|---|---|
| 1–125 | 1 | γ1 |
| 1–221 | 1 | γ1 |
| 1–503 | 1 | γ1 |
| 818–1320 | 3 | γ2 |
| 818–1442 | 3 | γ2 |
| 1–2045 | 3 | γ2 |
| 368–1144 | 34 | γ3 |
| 368–1218 | 34 | γ3 |
| 1–1433 | 34 | γ3 |

In another preferred embodiment, the nucleic acid contains a control region cloned in plasmid PPAC8856, which is deposited at ATCC with accession number 97906. In yet another preferred embodiment, the nucleic acid contains a control region cloned in plasmid PPARγ1 promoter-luc, which is deposited at ATCC with accession number 97862. In particular, the control region is one of nt −125 to +196 of the human PPARγ1 gene, nt −502 to +182 of the human PPARγ2 gene, or nt −777 to +74 of the human PPARγ3 gene. The "−" and "+" refer to 5' upstream or 3' downstream to the transcription initiation sites of human PPARγ gene.

In another preferred embodiment, the control region is a positive transcription element capable of up regulating the transcription of the human PPARγ1, γ2 or γ3 gene, e.g. containing a positive transcription element from nt −125 to +196 of the human PPARγ1 gene, nt −502 to +182 of the human PPARγ2 gene, or nt −777 to +74 of the human PPARγ3 gene.

In another preferred embodiment, the control region is a negative transcription element capable of down regulating the transcription of the human PPARγ 1, γ2 or γ3 gene, e.g. containing a negative transcription element from nt γ125 to +196 of the human PPARγ1 gene, nt −502 to +182 of the human PPARγ2 gene, or nt −777 to +74 of the human PPARγ3 gene.

In yet another preferred embodiment, the control region contains one or more CACC box, C/EBP binding site, TATA box, SP1 binding site, AP-1 binding site, and ADD-1/SREBP-1 binding site existing in Seq. ID NO: 1, 2, 3 or 34.

The control region may contain at least 100, 60, 30, 12, 8 or 6 contiguous nucleotides from the 5' non-coding sequence (5' UTR) or an intron of the human PPARγ1, γ2 or γ3 gene.

In other preferred embodiments, the control region is a promoter capable of initiating the transcription of the PPARγ gene.

By "promoter" is meant a DNA regulatory region capable of binding directly or indirectly to RNA polymerase in a cell and initiating transcription of a downstream (3' direction) coding sequence.

A preferred promoter of this invention contains a sequence in the above Table III. In another preferred embodiment, the promoter contains a sequence selected from the group consisting of the 1 kb fragment 5' upstream of the transcription initiation site of the human PPARγ1 gene, exon A1, intron A1, the 800 nt 5' upstream of the transcription initiation site of the human PPARγ3 gene, exon A2, intron A2, the 500 nt 5' upstream of the transcription initiation site of the human PPARγ2 gene, exon B, and intron B. In yet another preferred embodiment, the promoter contains nt −125 to +196 of the human PPARγ1 gene, nt −502 to +182 of the human PPARγ2 gene, or nt −777 to +74 of the human PPARγ3 gene.

A promoter of a DNA construct, including an oligonucleotide sequence according to the present invention, can be linked to a heterologous gene to regulate transcription from the heterologous gene, which includes genes for reporter sequences such as growth hormone, luciferase, green fluorescent proteins, chloramphenicol acetyl transferase, β-galactosidase secreted placental alkaline phosphatase and other secreted enzyme reporters.

By "isolated" in reference to nucleic acid is meant a polymer of 2 (preferably 21, more preferably 39, most preferably 75) or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular context. Thus, the sequence may be in a cell-free solution or placed in a different cellular environment or nucleic acid context. The term does not imply that the sequence is the only nucleotide chain present, but does indicate that it is the predominate sequence present (at least 10–20% more than any other nucleotide sequence) and is essentially free (about 90–95% pure at least) of non-nucleotide material naturally associated with it. The term does not encompass an isolated chromosome containing a PPARγ gene control region.

By "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased in a useful manner and preferably separate from a library of undefined clones. The term "significantly" here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The DNA from other sources may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

By "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/ml). Individual clones isolated from a genomic or cDNA library can be purified to electrophoretic homogeneity. The claimed DNA molecules obtained from these clones could be obtained directly from total DNA or from total RNA. The genomic or cDNA clones are not naturally occurring, but rather are preferably obtained via manipulation of a partially purified naturally occurring substance.

By "recombinant" in reference to nucleic acid is meant the nucleic acid is produced by recombinant DNA techniques such that it is distinct from a naturally occurring nucleic acid.

By "enhancer" is meant a DNA regulatory region that enhances transcription. An enhancer is usually, but not always, located outside the proximal promoter region and may be located several kilobases or more from the transcription start site, even 3' to the coding sequence or within the introns of the gene. Promoters and enhancers may alone or in combination confer tissue specific expression.

By "silencer" is meant a control region of DNA, which, when present in the natural context of the PPARγ gene, causes a suppression of the transcription from that promoter either from its own actions as a discreet DNA segment or through the actions of transacting factors binding to said elements and effecting a negative control on the expression of the gene. This element may play a role in the restricted cell type expression pattern seen for the PPARγ gene, for example expression may be permissive in adipocytes where the silencer may be inactive, but restricted in other cell types in which the silencer is active. This element may or may not work in isolation or in a heterologous promoter construct.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of"is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The specific control regions identified above can be modified by terminal deletions without abolishing their regulatory functions using methods known to those skilled in the art, including, but not limited to, those disclosed in U.S. Pat. No. 5,698,389, incorporated by reference herein. Therefore, this invention also encompasses terminal deletion mutants of the above-identified human PPARγ control regions.

In a second aspect, the invention features a recombinant nucleic acid comprising a control region of the human PPARγ gene as described above and a reporter gene sequence such as luciferase. The recombinant nucleic acid is preferably inserted in a vector (virus vector or plasmid vector). In addition, the recombinant nucleic acid is preferably transfected into a cell or an organism. The control region and the reporter sequence are operably linked so that the control region, such as a promoter, is effective to initiate, terminate or regulate the expression of the reporter sequence. The control region may contain one of human PPARγ1 promoter, human PPARγ2 promoter and human PPARγ3 promoter. Alternatively, the control region may contain two or three of the promoters in combination. The recombinant nucleic acid may further comprise a transcriptional termination region functional in a cell.

In a preferred embodiment, the promoter contains the region from about −3 kb to about +110 bp relative to the transcription initiation site of human PPARγ1 gene, from about −1 kb to about +122 bp relative to the transcription initiation site of human PPARγ2 gene, or from about −800 bp to about +1 bp relative to the transcription initiation site of human PPARγ3 gene. Exemplary recombinant nucleic acids are pGL3-γ1p3000, pGL3-γ2p1000, and pGL3-γ3p800.

The PPARγ gene control regions and the 5' untranslated region (5' UTR) described herein are useful for designing and preparing antisense molecules that interfere or inhibit RNA processing or translation of the PPARγ gene. The PPARγ gene control regions and the 5' untranslated region (5' UTR) described herein are also useful for designing and preparing ribozymes that cleave transcripts from the genomic PPARγ sequence, interfere or inhibit RNA processing or translation of the PPARγ gene. Such antisense molecules and ribozymes down regulate the expression of the PPARγ gene.

Therefore, in a third aspect, this invention features antisense molecules and ribozymes capable of down regulating the expression of the human PPARγ gene. The antisense nucleic acids of this invention are DNA or RNA molecules that are complementary to a PPARγ gene control region or a 5' untranslated region of PPARγ and hybridize to PPARγ transcripts in the cell to block RNA processing or translation. Antisense methods have been used to inhibit the expression of many genes in vitro (Marcus-Sekura, *Anal. Biochem.* 172:289–295, 1988; Hambor et al., *J. Exp. Med.,* 168:1237–1245, 1988). Ribozymes of this invention are RNA molecules possessing the ability to specifically cleave PPARγ transcripts containing a PPARγ gene control region or a 5' untranslated region of PPARγ in the cell (Cech, *J. Am. Med. Assoc.,* 260:3030–3034 (1988). Ribozymes capable of modulating the expression of a PPARγ gene can be designed and synthesized with methods known to one skilled in the art such as those disclosed in Stinchcomb, et al. "Method and Reagent for Inhibiting the Expression of Disease Related Genes," WO 95/23225.

In a fourth aspect, the present invention features a method for identifying agents which modulate or regulate the transcription of a PPARγ gene. Such agents are identified based on their ability to modulate the expression of a chimeric gene as described above wherein a heterologous coding sequence is regulated by a PPARγ gene control region taught by the present invention. Agents identified in this manner are useful as lead compounds to design or search for other drugs to treat disease related to the level of PPARγ gene expression. This method includes the following steps: (a) providing a recombinant nucleic acid as described above wherein a heterologous coding sequence is regulated by a human PPARγ gene control, wherein the control region is operably or transcriptionally linked to the reporter sequence to initiate, terminate or regulate the transcription of reporter, (b) contacting a candidate agent with a system containing the recombinant nucleic acid, and (c) assaying for a measurable difference in the level of transcription of the reporter sequence as an indicant of the candidate agent's activity. An agent that increases the level of transcription of the nucleic acid sequence is an up regulator. An agent that decreases the level of transcription of the nucleic acid sequence is a down regulator. The system can be a cell, an animal such as a mammal, or an in vitro transcription system. The preferred cells are eukaryotic cells, including yeast cells and mammalian cells.

In a preferred embodiment, the nucleic acid is introduced into a host cell or an organism by transfection, adenovirus infection or other methods of gene transfer and the system includes the cell or the organism. In an even further preferred embodiment, a transgenic animal system is used in the assay.

In another preferred embodiment, the system further includes a transcriptional protein. By "transcriptional protein" is meant a cytoplasmic or nuclear protein that, when activated, binds a promoter, enhancer or silencer either directly, or indirectly through a complex of proteins to modulate the transcription activity of the promoter. The transcriptional protein may either be endogenous to the cell or expressed from a recombinant nucleic acid transfected into the cell. Examples of transcriptional proteins include, but are not limited to, C/EBPβ protein and other proteins that bind to a C/EBP site or Sp1 site, and intracellular receptors. In a preferred embodiment, the transcriptional protein is ADD1/SREBP 1. By "intracellular receptor" is meant an intracellular transcription factor whose activity is regulated by binding of small molecules, including, but not limited to, estrogen receptor (ER), retinoid acid receptors (RAR), retinoid X receptors (RXR), glucocorticoid receptors (GR), progesterone receptors (PR), androgen receptors (AR), thyroid hormone receptors (TR), and vitamin D receptors. The intracellular receptor may either be endogenous to the cell or expressed from a recombinant nucleic acid transfected into the cell. A preferred intracellular receptor is an RXR such as RXRα.

In another preferred embodiment, the basal level of the mammalian PPARγ gene expression may be raised up before adding a candidate down regulator to the screening assay.

In a preferred embodiment, the assay is conducted in a mammalian adipocyte cell such as a primary adipocyte cell or an immortalized adipocyte cell. A rat, mouse or a human primary adipocyte cell is used. Mammalian preadipocytes may be used for the assay as well. Exemplary cells include 3T3-F422A, Ob1771, Ob17, 3T3-L1 and rat primary adipocyte. Any other cells in which the control region is capable of initiating, terminating or regulating the transcription of the reporter sequence may be used.

In another preferred embodiment, the sequence of the control region is used to guide the selection of potential modulators for screening. For example, if a glucocorticoid response element (GRE) is present in the control region, compounds known to act through these elements will be selected for screening. Other control elements useful in this way include, but are not limited to, peroxisome proliferator response elements (PPRE), thyroid hormone response elements (TRE), retinoic acid response elements (RARE), retinoid X response elements (RXRE), estrogen response elements (ERE), progesterone response elements (PRE), androgen response elements (ARE), insulin receptor response elements, other transcription regulatory binding sites such as the helix-loop-helix family members including sterol regulatory element binding protein family (SREBP) or its adipocyte expressed homologue ADD-1, CAAT/enhancer binding protein (C/EBP), AP-1, AP-2, SP-1, NFκB Oct-1, serum response elements, cAMP response elements, and growth hormone (GH) response elements.

In a preferred embodiment, the candidate agent is selected from the group consisting of estrogen receptor, retinoid acid receptors, retinoid X receptors, glucocorticoid receptors, progesterone receptors, androgen receptors, thyroid hormone receptors, and vitamin D receptors.

Peptide or small molecule combinatorial libraries can be used to screen for modulators of PPARγ gene expression (Bunin, B. A. N. Ellman, *J. A., J. Am. Chem. Soc.* 114: 10997–10998 (1992) and references contained therein).

The above described assays can be modified to allow assaying for agents that modulates the interaction of a transcriptional protein (e.g., ADD1/SREBP1) with a control region of the human PPARγ gene by including the regulatory protein in the assay. The activity of the agents is measured by the expression level of the reporter gene. In a preferred embodiment, the regulatory protein is expressed from a recombinant vector transfected into the assay system (e.g., a cell). Alternatively, the interaction or binding of the transcriptional protein control region of the human PPARγ gene can be measured by other techniques known to those skilled in the art, including, but not limited to, mobility shift assay, and co-transfection assay.

The activities of a candidate compound on the control regions of human PPARγ1, γ2, and γ3 can be compared to determine whether it has different effects on different human PPARγ promoters. Thus, this invention allows one to identify a modulator that is specific for one or more of human PPARγ1, γ2, and γ3 genes. In addition, the activities of a candidate compound on a control region of human PPARγ gene in different cells and tissues can be compared to determine the tissue specific function of the compound. In that regard, this invention allows one to identify a modulator that has tissue specific activity on one or more of human PPARγ1, γ2, and γ3 genes.

In a fifth aspect, the present invention features a method of identifying agents which modulate or regulate the transcription of a PPARγ gene by testing their ability to bind to a control region of the human PPARγ gene. An example is provided in the detailed description of the invention where a modulator of PPARγ gene, ADD-1/SREBP-1, was found to bind to the PPARγ3-E-box.

While steroids and steroid analogues may exemplify agents identified by the present invention, Applicant is particularly interested in the identification of agents of low molecular weight (less than 10,000 Daltons, preferably less than 5,000, and most preferably less than 1,000) which can be readily formulated as useful therapeutic agents.

Such agents can then be screened to ensure that they are specific to tissues with pathological conditions related to PPARγ gene expression with little or no effect on healthy tissues such that the agents can be used in a therapeutic or prophylactic manner. If such agents have some effect on healthy tissues they may still be useful in therapeutic treatment, particularly in those diseases which are life threatening.

Once isolated, a candidate agent can be put in pharmaceutically acceptable formulations, such as those described in Remington's Pharmaceutical Sciences, 18th ed., Mack Publishing Co., Easton, Pa. (1990), incorporated by reference herein, and used for specific treatment of diseases and pathological conditions with little or no effect on healthy tissues.

In a sixth aspect, this invention features a pharmaceutical composition capable of modulating the transcription activity of a human PPARγ gene control region, i.e. containing a pharmaceutically effective amount of a modulator (e.g. up regulator or down regulator) of the mammalian PPARγ gene control region. In a preferred embodiment, the composition is held within a container which includes a label stating to the effect that the composition is approved by the FDA in the United States (or other equivalent labels in other countries) for treating a disease or condition selected from the group consisting of obesity, anorexia, cachexia, lipodystrophy, lipomas, liposarcomas, abnormalities of adipose tissue associated with anti-HIV treatment, insulin resistance, diabetes mellitus (NIDDM), polycystic ovary syndrome, lipodystrophy, diseases of the GI tract, inflammatory bowel disease, Crohn's disease, ulcerative colitis, bowel cancer, irritable bowel syndrome, ulcerations of the GI tract, hyper- and dyslipidemia, hypertriglyceridemia, hypo-alpha lipoproteinemia, atherosclerosis, cardiovascular diseases, acute inflammation, septic shock, infection, chronic inflammation, inflammatory bowel disease, rheumatoid arthritis, allergic conditions, urticaria, eczema, asthma, immulogic disorders, graft versus-host disease, parasitic infections, bacterial infections, viral infections, breast cancer, prostate cancer, colon cancer, osteoporosis, bone loss, ARDS, and RDS. Such a container will provide therapeutically effective amount of the active ingredient to be administered to a host.

In a seventh aspect, this invention features a method for modulating the expression level of human PPARγ gene by administering to a host a composition including an effective amount of a modulator (e.g. up regulator or down regulator) of the control region In a preferred-embodiment, the method further includes step of measuring the transcriptional activity of the control region.

In further preferred embodiments, the composition includes an up regulator.

In another further preferred embodiments, the composition includes a down regulator.

In an eighth aspect, this invention relates to a method of diagnosing abnormal PPARγ expression in a host by detecting the expression level of human PPARγ1, γ2, or γ3 in one or more tissue samples from the host. In a preferred embodiment, the expression levels of human PPARγ1, γ2, and γ3 are detected and compared to that of healthy subjects.

Applicant has obtained intron sequences surrounding exons 1, 2, 3, 4, 5 and 6 (see SEQ ID NOs: 35, 36, 37, 38, 39 and 40). In that regard, this invention features oligonucleotide probes, methods and compositions for diagnosing genomic mutations in exon 1, 2, 3, 4, 5 or 6 of human PPARγ gene. Genomic mutations in one or more exons can be detected by oligonucleotide primer directed amplification and sequencing. For example, oligonucleotides of about 10 to about 100 bps can be designed to bind to the intron sequences immediately surrounding an exon for amplifying and/or sequencing the exon of genomic DNA in a cell sample collected from a host. Techniques known to those skilled in the art for amplifying and detecting nucleic acid targets can be applied for this aspect of the invention, including, but not limited to, WO 91/01384, EPC publication 0 569 237 A2, U.S. Pat. No. 5,683,880, incorporated by reference herein in their entirety.

Other features and advantages of the invention will be apparent from the detailed description of the invention below and from the list of enumerated embodiments that follows.

IV. BRIEF DESCRIPTION OF THE DRAWINGS

FIG. 1 shows the transcription initiation sites of the human PPARγ1 (SEQ ID NO: 31) and γ2 (SEQ ID NO: 32) in panels A and B, respectively. Transcription initiation sites as determined by primer extension are indicated by arrows. Transcription initiation sites as determined by 5'-RACE are indicated by asterisks. The sequence corresponding to the 5'-UTR is shown in panel A.

Figure 2B:
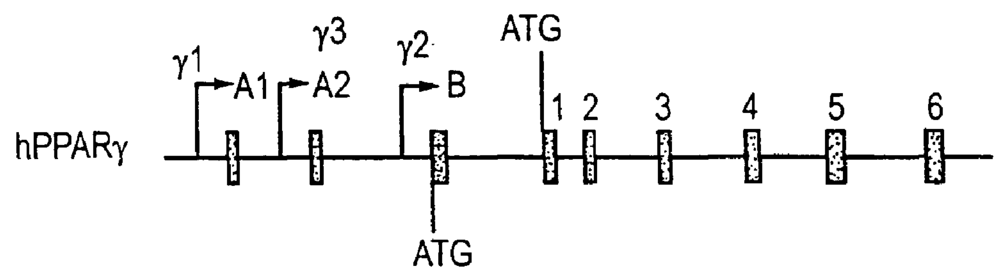

FIG. 2 is a schematic comparison of the gene organization of the mouse and human PPARγ genes. The genes are shown in 5' to 3' orientation and are drawn to scale. Restriction sites for BamHI are indicated by a "B." The location of the ATG start-codon is indicated. The asterisk indicates the different ATG used in mPPARγ1. Exons are denoted by gray or black rectangles and introns by solid lines.

Figure 3:
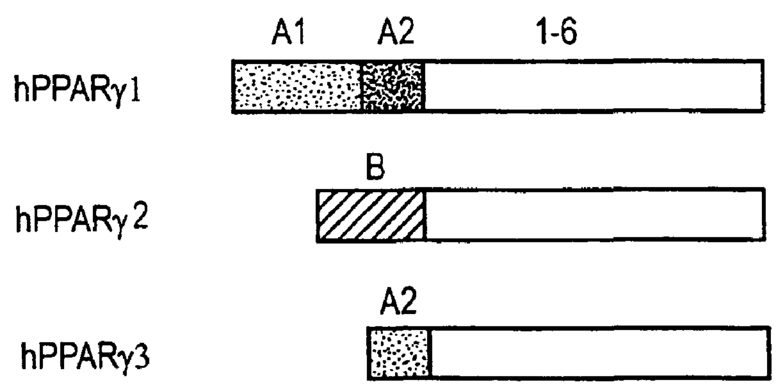

FIG. 3 is a schematic diagram showing the organization of post-transcription processed human PPARγ1, 2 and 3 mRNAs including the 5' untranslated terminal region. A1, A2, B and 1–6 denote exons.

FIG. 4 shows sequences of the human PPARγ3 promoter, exon A2 and intron A2 (SEQ ID NO: 34). Exon sequence is shown in capitalized letters. A* denotes the transcription initiation site. The ADD1/SREBP1 site, C/EBP site and TATA box are indicated in bold. The oligonucleotide LF-60 used for primer extension is indicated by an arrow.

FIG. 5 shows sequences of the human PPARγ1 proximal promoter, exon A1 and intron A1 (SEQ ID NO: 1). Exon sequence is shown in capitalized letters. G* denotes the transcription initiation site. The CACC box and Sp1 site are indicated in bold.

FIG. 6 shows the upstream sequence of the human PPARγ1 promoter 5' to the sequence shown in FIG. 5 (SEQ ID NO: 2).

FIG. 7 shows sequences of the human PPARγ2 promoter, exon B and intron B (SEQ ID NO: 3). Exon sequence is shown in capitalized letters. T* denotes the transcription initiation site. The TATA like box, C/EBP site, AP-1 site and translation initiation site are indicated in bold.

V. DETAILED DESCRIPTION OF THE INVENTION

Two important findings recently underlined the importance of the PPARγ transcription factor. First, PPARγ has been identified as one of the key factors controlling adipocyte differentiation and function in rodent systems (6, 7). Second, the recent identification of prostaglandin J2 derivatives and antidiabetic thiazolidinediones as natural and synthetic PPARγ ligands, respectively (28, 29, 46–48). Thiazolidinediones are a new group of anti-diabetic drugs which improve insulin-resistance (for review, see Refs. 49 and 50). The identification of thiazolidinediones as PPARγ ligands together with the central role that adipose tissue plays in the pathogenesis of important metabolic disorders, such as obesity and non-insulin-dependent diabetes mellitus (NIDDM), have generated a major interest to determine the role of this PPAR subtype in normal and abnormal adipocyte function in humans.

To identify the molecular circuitry underlying tissue-specific expression of PPAR, we cloned and performed a characterization of the human PPARγ promoters. As shown, 3000 bp of the PPARγ1 and 1000 bp of the PPARγ2 promoter account for substantial levels of basal promoter activity.

In addition to PPARγ, the basic helix-loop-helix leucine zipper factor ADD-1/SREBP1 and transcription factors of the C/EBP family also play a role in determining adipocyte differentiation. As in the mouse PPARγ2 promoter (45), a potential consensus C/EBP response element is identified in the human PPARγ2 promoter by homology searches. This observation fits well with the previous observation that forced expression of C/EBPα could induce PPARγ expression (11, 12).

A. Cloning of the Human PPARγ cDNA

A cDNA probe containing a 200-bp (KpnI-BglII) fragment encoding the DNA binding domain of the mouse PPARγ (44) was used to screen a human adipose tissue cDNA library. Several independent human PPARγ cDNA clones, representing both the PPARγ1 and PPARγ2 subtypes, were isolated and sequenced. The human PPARγ protein shows a 99% similarity and a 95% identity at the amino acid level with mouse PPARγ (45). Relative to the mouse, hamster, and *Xenopus* PPARγ (6, 39, and 51), the human protein contains two additional amino acids. This is in agreement with the previous reports on the human PPARγ cDNA (34, 35, and 52).

B. Locating Promoters of the Human PPARγ Genes

Two approaches were undertaken to identify the 5'-end of the cDNA. First, primer extension experiments were performed, utilizing different human adipose tissue RNA samples. The result from primer extension was independently confirmed by 5'-RACE.

Several primer extension products were seen for the PPARγ1 mRNA. The relative positions of the transcription initiation sites as determined by the 5'-RACE were in agreement with the results for primer extension.

One major extension product of 62 bp was observed consistently with the primer LF-35 for PPARγ2. A second extension product of 96 bp was found using the same. The result of 5'-RACE was consistent with the primer extension.

The transcription initiation sites identified correlated well with the transcription initiation sites observed for the mouse PPARγ2 mRNA (45). A striking feature of the human PPARγ2 5'-UTR is its high degree of sequence conservation with the mouse 5'-UTR.

We cloned the regions 5' to the transcription initiation sites of PPARγ1 and γ2 and sequenced the proximal promoters.

No canonical TATA box was found in the PPARγ1 promoter region close to the transcription initiation site (FIG. 1). The sequence immediately upstream of the transcription initiation site is extremely GC-rich, including several consensus Sp1 binding sites. A CCAAC box was found in the proximal promoter.

The PPARγ2 promoter contains a TATA-like element at position −68, relative to the transcription initiation site. Furthermore, sequence analysis identified a potential CAAT-like consensus C/EBP protein binding site at −56 (CCAATT) and a perfect AP-1 site at +10 (TGACTCA) (FIGS. 1 and 3).

A more detailed analysis of the 5' upstream sequence of exon A2 (FIG. 2) indicated the presence of a TATA and CCAAT box. This suggests the presence of a third promoter in the PPARγ gene and an alternative PPARγ mRNA containing only the exon A2 in its 5' UTR.

In order to assess this possibility, an RNase protection assay was performed using a radiolabelled probe containing both the A1 and A2 untranslated exons plus a sequence common for all PPARγ mRNAs, i.e., exon 1. In the presence of a PPARγ mRNA species containing exclusively exon A2, this probe yielded a protected fragment that is 42 bp shorter than the fragment present in PPARγ1, which contains both exons A1 and A2.

In addition, RNase protection assays of RNA from colon and adipose tissues—two tissues known to express high levels of PPARγ—showed an additional RNA species, which is different from PPARγ1 and 2. The size of this new mRNA species corresponds to an RNA containing only exon A2.

We performed primer extension experiments on human adipose tissue RNA to identify the 5' end of this novel PPARγ cDNA. One major primer extension product of 37 bp was observed with the primer LF-60. The length of the extended product indicates that this new mRNA begins at the initiation of the exon A2. In the same primer extension assay, we could not observe any band corresponding to the PPARγ1 transcription initiation site because the length of the extended product corresponding to the PPARγ1 mRNA is longer than 180 bp, which makes it very difficult to detect using this technique. These data unequivocally demonstrate the presence of an additional PPARγ transcription initiation site giving rise to a new PPARγ mRNA which we designated as PPARγ3. The PPARγ3 mRNA will, however, be translated into a protein that is indistinguishable from PPARγ1 because there is no translation initiation site in exon A2.

Accordingly, the locations of the three promoters for the human PPARγ gene are shown in FIG. 2.

We sequenced the region 5' to the transcription initiation site of the PPARγ3 mRNA, which corresponds to the proximal PPARγ3 promoter (FIG. 4). Several consensus sequence elements were identified. A TATA-like element was found at −34 relative to the transcription initiation site. Sequence analysis furthermore identified a potential CAAT-like consensus C/EBP binding site at −118 as well as a potential E-box binding site for the transcription factor ADD-1/SREBP-1 at the position −342 (FIG. 4).

To clone the human PPARγ gene and to determine its promoter-sequence, we screened a PAC human genomic library derived from human foreskin fibroblasts. Three positive clones (P-8854, P-8855, and P-8856), each spanning >100 kb of genomic sequence, were isolated. All-three clones were next shown to hybridize with the oligos LF-14 (corresponding to exon B) and LF-36 (exon 6), which indicates that they span most of the PPARγ coding region. More importantly, clone P-8856 also hybridized to oligo LF-2 and, hence, contains the transcription initiation site for PPARγ1 and 2. This clone was further characterized by Southern blotting and partial sequence analysis, which allowed the construction of a physical map of the human PPARγ locus (FIG. 2).

The human PPARγ gene has nine exons and extends over more than 100 kilobases of genomic DNA. Alternate transcription start sites and alternate splicing generate the PPARγ1 and PPARγ2 mRNAs, which differ at their 5'-ends. PPARγ1 is encoded by eight exons, and PPARγ2 is encoded by seven exons. The 5'-untranslated sequence of PPARγ1 is comprised of exons A1 and A2. The 5'-untranslated sequence of PPARγ2 plus the additional 28 PPARγ 2-specific N-terminal amino acids are encoded by exon B, which is located between exons A2 and A1. The remaining six exons, termed 1 to 6, are common to the PPARγ1 and γ2. A third PPARγ mRNA, PPARγ3, is transcribed from an independent promoter localized 5' of exon A2.

The length of the introns was determined by long-range PCR (CLONTECH Tth polymerase mix) using the oligonucleotide pairs LF-3/LF-18, LF-20/LF-21, LF-22/LF-23, LF-24/LF-25, LF-26/LF-27, and LF-28/LF-29 and the PAC clone P-8856 as a template. The intron-exon boundaries were sequenced using genomic DNA as template. The 5' donor and 3' acceptor splice sites were found to be conforming to the consensus splice donor and acceptor sequences (Table II). The DNA binding domain of the receptors is encoded by exons 2 and 3, each encoding a separate zinc finger. The entire ligand-binding domain is encoded by exons 5 and 6, which are separated by 16.3 kb of intron sequence.

C. Tissue-Specific Expression of human PPARγ1, 2 and 3

We employed two RNase protection assays to study the relative expression of the three PPARγ subtypes in different tissues (see the methods section and Table I for the description of the probes). The first RNase protection assay was designed to determine the amount of PPARγ2 mRNA relative to PPARγ1 and PPARγ3 mRNAs, whereas the second RNase protection assay was designed to determine the amount of PPARγ3 relative to PPARγ1 and PPARγ2 mRNA.

Human PPARγ3 mRNA is expressed in adipose tissue, CaCo2 cells from the intestine and macrophages. With the exception of human white adipose tissue, none of the tissues or cell-lines analyzed contained substantial amounts of PPARγ2 mRNA. In contrast to the tissue restricted expression of the PPARγ2 and 3 mRNAs, PPARγ1 mRNA is more widely expressed and is detected in adipose tissue, human hepatocytes, and the cell-lines Hep G2 (liver), CaCo2, HeLa (uterus), and THP1 (monocyte/macrophage). The expression of PPARγ3 mRNA is induced upon differentiation of the CaCo2 cell line.

To evaluate the tissue specificity of these promoters, DNA fragment extending from about −3 kb to +110 bp relative to the transcription initiation site of PPARγ1 was inserted into the pGL3-basic luciferase vector (Promega) to generate the construct pGL3-γ1p3000. DNA fragment extending from about −1 kb to +122 bp relative to the transcription initiation site of PPARγ2 was inserted into the pGL3-basic luciferase vector (Promega) to generate the construct pGL3-γ2p1000. These vectors were then transfected into mouse 3T3-L1 and Hep G2 cells. Transfection efficiency of the various cell lines was monitored by evaluation of the activity of control vectors.

Relative to the promoterless parent vector, the human PPARγ1 promoter fragment stimulated luciferase expression up to 3.5-fold in 3T3-L1 cells, maintained under non-differentiating conditions. In Hep G2 cells, luciferase expression was nine-fold higher with the pGL3-γ1-p3000 vector relative to the pGL3-basic vector. Similar results were obtained with COS cells. The expression of the pGL3-γ2p1000 construct containing the PPARγ2 promoter was not different from the pGL3-basic promoterless vector in Hep G2 cells. In undifferentiated 3T3-L1 cells, the PPARγ2 promoter induced luciferase expression 2-fold relative to the promoterless control.

To evaluate the activity and tissue specificity of the PPARγ3 promoter, we cloned an 800 bp fragment located immediately upstream of the transcription initiation site of PPARγ3 into the luciferase reporter vector pGL3 basic. The resulting plasmid pGL3-γ3p800 was transfected into the mouse 3T3-L1 and human Hep G2 cell lines. Transfection efficiency was monitored by evaluation of the activity of a β-galactosidase control vector. Relative to the promoterless parent vector, the PPARγ3 promoter stimulated the luciferase expression more than two-fold in Hep G2 cells and in undifferentiated 3T3-L1 cells. The activity of the PPARγ3 promoter was in the same range as the activity observed for the PPARγ1 and γ2 promoter in these cells. The relative weak stimulation of luciferase gene expression in undifferentiated 3T3-L1 and Hep G2 cells is in agreement with the low level of expression of PPARγ in these cells.

To analyze the expression pattern of the PPARγ isoforms, we developed a sensitive RT-competitive PCR assay in which relative amounts of PPARγ1 and γ2 mRNA could be measured in minute quantities of RNA (0.1 μg total RNA). This method relies on the co-amplification in the same tube of known amounts of competitor DNA with PPARγ cDNA, obtained after reverse transcription from total tissue RNA. The competitor and the target use the same fluorescently labeled PCR primers but yield amplicons of different sizes, allowing their separation and quantification on an automated sequencing gel at the end of the reaction.

All tissue preparations were carefully dissected, and the RNA was shown to be free of contamination by adipose tissue as evidenced by the absence of human leptin mRNA by RT-competitive PCR assay (38).

PPARγ1 mRNA was the predominant PPARγ isoform in all human tissues analyzed. PPARγ2 was detected in both liver and adipose tissue where it accounted for 15% of all PPARγ mRNA. In addition to the high level of expression of PPARγ mRNA expected in adipose tissue, we found a very high level of PPARγ1 in large intestine. In contrast to adipose tissue, large intestine contained no PPARγ2 mRNA. Kidney, liver, and small intestine contained intermediate levels of PPARγ mRNA, whereas PPARγ mRNA was barely detectable in skeletal muscle. PPARγ3 mRNA, which gives rise to a protein identical to PPARγ1, is exclusively expressed in adipose tissue and the large intestine.

Next, the expression of the human PPARγ protein was analyzed in human adipose tissue. A PPARγ specific antibody, raised against a peptide corresponding to amino acids 20–104 of mPPARγ, was used. This antibody is highly specific for PPARγ and does not cross-react with PPARαand β in Western blot experiments. Using this antibody in a Western blot of protein extracts from human adipose tissue, we detected a band (potentially representing a doublet) with an approximate molecular mass of 60 kDa, consistent with the predicted mass of PPARγ1 and 2 and with the protein product generated by in vitro transcription/translation in the presence of [35S]methionine.

Our results in humans as well as the data by Xue et al. (53) in rodent adipocytes show consistently lower levels of PPARγ2 mRNA and protein relative to the PPARγ1 subtype. These observations are in line with the previous observations that the N-terminal domain of PPARγ was dispensable, both regarding transcriptional activation and capacity to induce adipocyte differentiation in vitro (7). However, the N-terminal domain is highly conserved between different species, suggesting it might have an important function in vivo.

That PPARγ expression is much more widespread than previously realized implies that PPARγ controls gene expression in several tissues in addition to adipose tissue. For example, PPARγ is expressed in the macrophage and foam cells (Ricote M, et al., *Proc Natl Acad Sci USA* 95(13): 7614–7619 (1988)). Especially striking is the high level of PPARγ expression in the human large intestine. These results are consistent with the reported high level expression of PPARγ in colonic mucosa in mouse (54).

PPARγ is expressed in a subset of macrophages and negatively regulates the expression of several pro-inflammatory genes in response to its ligands. We recently discovered the presence of PPARγ in human macrophages foam cells of human atherosclerotic lesions. In these cells, PPARγ is present in a pattern correlated with that of oxidation-specific epitopes. Oxidized low-density lipoprotein (LDL) and macrophage colony stimulating factor (MCSF) are known to be present in atherosclerotic lesions. In addition, oxidized LDL and MCSF stimulate PPARγ expression in primary macrophages and monocytic cell lines. Furthermore, phorbol esters induced PPARγ expression. Inhibition of PKC blocked induction of PPARγ by phorbol esters but not by oxidized LDL, suggesting that more than one pathway regulate PPARγ expression in macrophages.

Fatty acids, which are potential PPAR activators, have been shown to play an important role in modulating the function of the large intestine. For instance, diets enriched in saturated lipids have been shown to predispose the development of colon cancer (55). Furthermore, it has been shown that diets enriched in omega-3 fatty acids, which are powerful PPAR activators, have a beneficial response on inflammatory diseases of the gastrointestinal tract such as colitis ulcerosa and Crohn's disease (56, 57). The high level expression of PPARγ suggest that it plays an important role in normal and abnormal colonic function.

The low levels of PPARγ expression in skeletal muscle cells suggest that PPARγ agonists such as TZD's reduce insulin resistance primarily through adipose tissues. Muscle is responsible for clearance of the majority of glucose in the body and abnormal muscle glucose uptake is one of the prime features of insulin resistance and NIDDM. The low levels of PPARγ in muscle argue, therefore, that the beneficial effects of thiazolidinedione antidiabetic agents are not likely to be due to a direct effect of these agents on PPARγ present in the muscle. In fact, even though the liver has considerably higher levels of PPARγ relative to muscle, thiazolidinediones do not seem to affect PPAR responsive genes in liver tissue at the concentrations commonly used to lower glucose levels (23). This observation together with the observed tissue distribution of PPARγ suggests that the glucose lowering effects of the thiazolidinedione PPARγ ligands are primarily a result of their activity on adipose tissue, which then, via a secreted signal, influencesmuscle glucose uptake.

D. PPARγ2 Binds and Transactivates through a PPRE (Assay for PPARγ Agonists and Antagonists)

To analyze whether PPARγ could bind to a PPRE, classically composed of direct repeats spaced by one intervening nucleotide (DR-1), EMSA was performed using in vitro transcribed/translated PPARγ2 protein. An oligonucleotide containing a high affinity PPRE, previously identified in the apoA-II promoter J site, was used in EMSA (29). This oligonucleotide was capable of binding both human and hamster PPARγ/mRXRα heterodimers in EMSA. Homodimers of either hPPARγ or mRXRα, however, were incapable of binding to this oligonucleotide. When increasing concentrations of unlabeled apoA-II J site were added as competitor, binding of the hPPARγ/mRXRα heterodimer to the labeled PPRE was almost completely inhibited. In addition, oligonucleotides corresponding to the PPRE elements of the ACO or LPL genes competed, albeit less efficiently.

We next verified that the human PPARγ2 cDNA was capable of activating gene transcription through a PPRE. Therefore, 3T3-L1 preadipocytes were cotransfected with the PPARγ2 expression vector pSG5hPPARγ2 and a PPRE-driven luciferase reporter gene. The luciferase gene was under the control of a multimerized ACO-PPRE site and the TK promoter. hPPARγ2 was capable of activating this PPRE-based reporter 2-fold, an effect which was substantially enhanced when hPPARγ2 was cotransfected together with RXRα. Upon the addition of the PPARγ ligand BRL-14653, luciferase expression was increased 6-fold when the transfection was done with hPPARγ2 alone or at least 10-fold when the cells were co-transfected with both hPPARγ2 and mRXRα. Similar results were obtained when prostaglandin J2 was used as a PPARγ ligand. The above-described cell assay can be used to screen for other PPARγ2 protein agonists and antagonists. It can also be used to screen for agonists and antagonists of PPARγ1 protein by substituting hPPARγ2 with hPPARγ1.

E. Utility of the Cloned PPARγ Gene Control Regions

The cloned control regions of the human PPARγ gene provide a powerful tool for dissecting the role of the PPARγ gene product in a variety of diseases and disorders. These cloned control regions also provide novel tools for discovering pharmacological modulators of PPARγ gene expression. In addition, the availability of the structure of the human PPARγ gene allows for genetic studies of PPARγ mutations in humans, evaluating its role in disorders such as insulin resistance, NIDDM, and diseases characterized by altered adipose tissue function such as obesity or lipodystrophic syndromes.

1. Assay Systems Using Cells

The host cells used in the screening assay herein preferably are mammalian cells, and more preferably are human cell lines.

The host cells may be used to observe the regulation of endogenous PPARγ gene expression. These cells, whether derived from rodent, human or other mammalian species, can be used to monitor the expression of a reporter gene driven by human PPARγ gene control elements or regions.

Chimeric reporter genes containing the control regions of the PPARγ gene operatively linked to a coding sequence for a reporter may be introduced into a host cell according to standard techniques, such as via electroporation technology (Quon, M. J. et al. *Biochem. Biophys. Res. Comm.* 194: 338–346, (1993)).

Cell systems other than mammalian may also be used in the screening assays, such as *Drosophila* (SL-2, Kc or others) and yeast strains (permeabilized or not) such as *S. cerevisiae* or *S. pombe*, provided that such cells are modified to contain a chimeric reporter gene whose expression is regulated by control regions of the PPARγ gene.

a. Reporter Sequences

Generally, reporter genes encode a polypeptide not otherwise produced by the host cell which is detectable by in situ analysis of the cell culture, e.g., by the direct fluorometric, radioisotopic or spectrophotometric analysis of the cell culture without the need to remove the cells for signal analysis from the culture chamber in which they are contained. Preferably the gene encodes an enzyme which produces colorimetric or fluorometric changes in the host cell which is detectable by in situ analysis and which is a quantitative or semi-quantitative function of transcriptional activation. Exemplary enzymes include luciferase, green fluorescent proteins, chloramphenicol acetyl transferase, β-galactosidase, β-lactamase, secreted placental alkaline phosphatase, human growth hormone, esterases, phosphatases, proteases (tissue plasminogen activator or urokinase) and other secreted enzyme reporters and other enzymes whose function can be detected by appropriate chromogenic or fluorogenic substrates known to those skilled in the art.

A preferred example is *E. coli* β-galactosidase. This enzyme produces a color change upon cleavage of the indigogenic substrate indolyl-B-D-galactoside by cells bearing β-galactosidase (see, e.g., Goring et al., *Science* 235: 456–458 (1987) and Price et al., *Proc. Natl. Acad. Sci. USA* 84:156–160 (1987)). This enzyme facilitates automatic plate reader analysis of PPARγ control region mediated expression directly in microtiter wells containing transformants treated with candidate activators. Also, because the endogenous β-galactosidase activity in mammalian cells ordinarily is quite low, the analytic screening system using β-galactosidase is not hampered by host cell background.

Another class of reporter genes which confer detectable characteristics on a host cell are those which encode polypeptides, generally enzymes, which render their transformants resistant against toxins, e.g., the neo gene which protects host cells against toxic levels of the antibiotic G418 a gene encoding dihydrifolate reductase, which confers resistance to methotrexate or the chloramphenicol acetyltransferase (CAT) gene (Osborne et al., *Cell,* 42:203–212 (1985)). Resistance to antibiotic or toxin requires days of culture to confirm, or complex assay procedures if other than a biological determination is to be made.

Other genes for use in the screening assay herein are those capable of transforming hosts to express unique cell surface antigens, e.g., viral env proteins such as HIV gp120 or herpes gD, which are readily detectable by immunoassays. The polypeptide products of the reporter gene are secreted, intracellular or, as noted above, membrane bound polypeptides. If the polypeptide is not ordinarily secreted it is fused to a heterologous signal sequence for processing and secretion. In other circumstances, the signal is modified in order to remove sequences that interdict secretion. For example, the herpes gD coat protein has been modified by site directed deletion of its transmembrane binding domain, thereby facilitating its secretion (See, EP 139,417A). This truncated from of the herpes gD protein is detectable in the culture medium by conventional immunoassays. Preferably, however, the products of the reporter gene are lodged in the intra-cellular or membrane compartments. Then they can be fixed to the culture container, e.g. microtiter wells, in which they are grown, followed by addition of a detectable signal generating substance such as a chromogenic substrate for reporter enzymes.

b. Linkage of PPARγ Gene Control Regions to Reporters

In general, a PPARγ gene promoter is employed to control transcription and hence influence expression of the reporter gene. The PPARγ gene promoter is optionally combined with more potent promoters, e.g. the TK or SV40 early promoter, in order to increase the sensitivity of the screening assay.

A preferred condition would be to use the sequences upstream or 5' to the transcription initiation site or the coding sequence as the control elements, with or without additional promoter elements such as a TATA sequence or other sequences as may be required and obvious to one practiced in the art of heterologous gene expression and with or without intron sequences fused to a reporter gene to measure the effects of candidate compounds added to the cell culture.

The PPARγ gene promoter, whether a hybrid or the native PPARγ gene promoter, is ligated to DNA encoding the reporter gene by conventional methods. The PPARγ gene promoter is obtained by in vitro synthesis or recovered from genomic DNA. It is ligated into proper orientation (5' to 3') adjacent 5' to the start codon of the reporter gene with or without additional control elements. The region 3' to the coding sequence for the reporter gene will contain a transcription termination and polyadenylation site, for example, the hepatitis B or SV40 polyA site. The promoter and reporter gene are inserted into a replicable vector and transfected into a cloning host such as *E. coli*, the host cultured and the replicated vector recovered in order to prepare sufficient quantities of the construction for later transfection into suitable eukaryotic host.

The screening assay typically is conducted by growing the PPARγ gene promoter transformants (e.g. stably transformed) to a suitable state of confluency in microtiter wells, adding the candidate compounds to a series of wells, and determining the signal level after an incubation period that is sufficient to demonstrate a measurable signal in the assay system chosen. The wells containing varying proportions of candidates are then evaluated for signal activation. Candidates that demonstrate dose related enhancement of reporter gene transcriptions or expression are then selected for further evaluation as clinical therapeutic agents. Candidate compounds may be useful therapeutic agents that would modulate PPARγ gene expression.

2. Transgenic Animals and Gene therapy

Transgenic animals can be used in lieu of cultured cells for screening assays of this invention. The human PPARγ control regions may be introduced into animals by transgenic techniques, such as those disclosed in PCT publication WO 94/18959, incorporated by reference herein.

Transgenic mice carrying a cloned human PPARγ gene can be used both as a primary screening vehicle in which compounds can be administered and parameters sensitive to changes in expression of the PPARγ gene such as PPARγ mRNA production can be measured along with other appropriate controls to effectively assess the changes in expression of the PPARγ gene as well as a means of corroborating primary compound positives.

Alternatively, the cloned human PPARγ gene can be introduced into animals utilizing adenovirus drag technology in which the target DNA is admixed with poly-L-lysine and/or transferrin or asialoglycoprotein modified adenovirus and injected into the animal, resulting in expression of the foreign DNA (Wu et al., *JBC* 266:14338–14342, (1991); Yanow et al., *PNAS* 90:2122–2126 (1993)). In a preferred embodiment, recombinant adenovirus carrying the exogenous DNA can be injected directly into fat deposits of mice, rats or other species as has been done previously in brain (Davidson, *Nature Genetics* 3:219, Science 259:988), muscle (Quantin, PNAS 89:2581, Statford-Perricaudet *J. Clin. Invest.* 90:626), and tumors. These animal model assay systems are also useful in secondary characterization and study of compounds found to regulate human PPARγ gene expression identified in other assays. Additionally, the coding region of the PPARγ gene can be replaced with a reporter coding sequence as described above which could be then introduced into animals either via the standard transgenic practice or through the use of adenoviral drag or other methods of introducing foreign DNA into animals.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al. *Proc. Nat. Acad. Sci. USA* 82: 4438–4442 (1985)). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia* 47: 897–905 (1991). Other procedures for introduction of DNA into tissues of animals are described in U.S. Pat. No. 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., *Cell* 63:1099–1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells, A Practical Approach*, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, *Science* 244: 1288–1292 (1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., *Nature* 338: 153–156 (1989), the teachings of which are incorporated herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. See Houdebine and Chourrout, supra; Pursel et al., *Science* 244:1281–1288 (1989); and Simms et al., *Bio/Technology* 6:179–183 (1988).

Where a modulator of a PPARγ control region is a protein (e.g., ADD-1/SREBP-1), the modulator can be introduced into relevant cells in a host by gene therapy (reviewed in Miller, *Nature* 357:455–460, (1992). In addition, the human PPARγ control regions can be operably linked to a wild type or mutant PPARγ coding sequence and inserted into a host for expressing the wild type or mutant PPARγ gene. The human PPARγ control regions can also be operably linked to a different gene and inserted into a host for tissue specific expression under the regulation of the human PPARγ control regions. An in vivo model of gene therapy for human severe combined immunodeficiency is described in Ferrari, et al., *Science* 251:1363–1366, (1991). The basic science of gene therapy is described in Mulligan, *Science* 260:926–931, (1993).

In one preferred embodiment, an expression vector containing the hPPARγ control region is inserted into cells, the cells are grown in vitro and then infused in large numbers into patients.

The gene therapy may involve the use of an adenovirus containing the target DNA, implantation of engineered cells, or injection of naked DNA into appropriate tissues.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) into the targeted cell population (e.g., tumor cells). Methods well known to those skilled in the art can be used to construct recombinant viral vectors containing coding sequences. See, for example, the techniques described in Maniatis et al., *Molecular Cloning: A Laboratory Manual*, Cold Spring Harbor Laboratory, N.Y. (1989), and in Ausubel et al., *Current Protocols in Molecular Biology*, Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., *Nature* 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. Capecchi M R, *Cell* 22:479–88 (1980). Once recombinant genes are introduced into a cell, they can be recognized by the cell's normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, *Mol. Cell Biol.* 7:2745–52 (1987)); electroporation, wherein cells are exposed to large voltage pulses to introduce holes into the membrane (Chu G. et al., *Nucleic Acids Res.,* 15:1311–26 (1987)); lipofection/liposome fusion, wherein DNA is packaged into lipophilic vesicles which fuse with a target cell (Felgner P L., et al., *Proc. Natl. Acad. Sci. USA.* 84:7413–7 (1987)); and particle bombardment using DNA bound to small projectiles (Yang N S. et al., *Proc. Natl. Acad. Sci.* 87:9568–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel D T et al., *Am. J. Respir. Cell. Mol. Biol.,* 6:247–52 (1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

3. Example 1: Identifying a Modulator of Human PPARγ

The following example identifies a transcription modulator of human PPARγ.

a. ADD-1/SREBP-1 Regulates hPPARγ Transcription Through an E-box Motif in the hPPARγ3 Promoter Sequence analysis of the hPPARγ3 promoter region revealed the presence of a putative E-box binding site for ADD-1/SREBP-1 protein at position −342, which we defined as the PPARγ3-E-box. In order to demonstrate direct binding of ADD-1/SREBP-1 to the PPARγ3-E-box, we used double-stranded oligonucleotides corresponding to the PPARγ3-E-box (LF-102) as a probe in EMSA. Baculovirus-produced and partially purified ADD-1/SREBP-1 is capable of binding to this site. Competition assays using increasing amounts of either a cold double-stranded oligonucleotide containing the PPARγ3-E-box, a consensus 3-hydroxy-3-methylglutaryl coenzyme A synthase SRE (Smith et al., *J. Biol. Chem.* 263:18480–18487 (1988)), or the mutated PPARγ3-E-boxmut were performed in order to demonstrate the specificity of the binding. Binding of ADD-1/SREBP-1 to the PPARγ3-E-box is competed by both the cold PPARγ3-E-box, and by the consensus SRE oligonucleotides (Smith et al., *J. Biol. Chem.* 263:18480–18487 (1988)), whereas the mutated PPARγ3-E-boxmut oligonucleotide was unable to compete with the PPARγ3-E-box for binding of SREBP-1. Similar data were obtained when in vitro translated ADD-1/SREBP-1 protein was used instead of baculovirus-produced protein.

To assess whether ADD-1 regulates the expression of the hPPARγ3 mRNA, we cotransfected either an expression plasmid coding for ADD-1 together with the pGL3γ3p800 luciferase reporter vector. When Hep G2 cells were cotransfected with the ADD-1 expression vector, the luciferase activity was increased at least 4-fold relative to the basal activity of the hPPARγ3 promoter. As a control we transfected the pGL31p3000 and pGL3γ2p1000 expression plasmids, which contain respectively 3 kb and 1 kb of the human PPARγ1 and 72 promoter (Fajas et al., *J. Biol. Chem.* 272:18779–18789 (1997)). Activity of these two reporter constructs was unaffected when the ADD-1 expression vector was cotransfected, suggesting that the effect on the PPARγ3 promoter was specific. To unequivocally demonstrate that it is through binding to the PPARγ3-E-box that ADD-1 stimulates the activity of the hPPARγ3 promoter, we substituted three bases in the PPARγ3-E-box (from ATTCATGTGACAT (SEQ ID NO: 41) to ATTCATGCATCAT (SEQ ID NO: 42)) to generate the pGL3γ3p800-E-boxmut reporter plasmid. Cotransfected ADD-1 is unable to stimulate the mutated pGL3γ3p800-E-boxmut reporter vector in Hep G2 cells, whereas in the same experiment, the wild-type promoter is induced by 4-fold. Qualitatively similar results were obtained when an expression vector for mouse SREBP-1a was used.

Next, we evaluated the activity of the various PPARγ promoters in cholesterol depleted cells, a condition which is known to stimulate the proteolytic activition of ADD-1/SREBP-1 (Sakai et al., *Cell* 85:1037–1046 (1996); Shimomura et al., *Proc. Natl. Acad. Sci. USA* 94:12345–12359 (1997); Wang et al., *Cell* 77:53–62 (1994)). Cells were therefore transfected with the pGL3γ3p800, pGL3γ2p1000, and pGL3γ1p3000 reporter vectors and then incubated in the presence or absence of cholesterol in the media. The PPARγ3 promoter construct was significantly induced (2-fold) when the cells were maintained in cholesterol-depleted medium. No effect of cholesterol was observed when the pGL3γ3p800-E-boxmut reporter vector, in which the E box was mutated, was used, suggesting that the induction of the PPARγ3 promoter observed upon depletion of cholesterol is mediated by ADD-1/SREBP-1. The pGL3γ2p1000 and pGL3γ1p3000 promoter reporter constructs, which were not induced by ADD-1/SREBP-1 cotransfection, were also unresponsive to cholesterol depletion. This assay can be used to screen for other transcription modulators of PPARγ1, 2, and 3.

b. Ectopically Expressed ADD-1/SREBP-1 Induces PPARγ mRNA Expression.

To investigate whether ADD-1/SREBP-1 expression was sufficient to regulate the expression of the endogeneous PPARγ3 mRNA, Hep G2 cells were electroporated with vectors expressing either SREBP-1a (Yokoyama et al., *Cell* 75:187–197 (1993)) or ADD-1 (Tontonoz et al., *Mol. Cell. Biol.* 13:4753–4759 (1993)). RNA was extracted 48 hr after transfection and analysed by RNase protection assay for the presence of PPARγ mRNA. PPARγ3 mRNA levels were significantly elevated (at least 2-fold) in the cells transfected either with SREBP-1a or with ADD-1, whereas no induction of PPARγ3 mRNA was detected in cells transfected with an empty expression vector. Interestingly, PPARγ1 mRNA, which was expressed to a much higher level under basal conditions relative to PPARγ3, was also increased (approximately 3-fold) with either the SREBP-1a or ADD-1 expression vectors. This demonstrates that ADD-1/SREBP-1 controlled not only the transcription of the PPARγ3 promoter but also that of the other more distant PPAR γ promoters. These results suggest that the increased PPARγ expression in response to cholesterol depletion is the result of an increased transcriptional activity of the PPARγ3 promoter.

To study the effects of ADD-1 on PPARγ expression in more detail, either an empty retroviral vector pBabe or the same vector encoding for full length ADD-1 or the super-active ADD-1-403 form were introduced into 3T3-L1 cells via retroviral infection. Northern blot analysis showed that retroviral infection, by the virus encoding for ADD-1, resulted in a two-fold higher level of ADD-1 expression. Infected cells were then cultured to confluence and consecutively treated with differentiation medium. Total RNA was isolated at confluence (preadipocytes) and at day 6 after confluence (adipocytes) from the cells expressing either the empty pBabe vector or the same vector encoding for ADD-1 or ADD-1-403, a truncated form of ADD-1, equivalent to the proteolytically activated protein, which lacks the membrane anchoring domain. RNase protection assay indicated that the expression of PPARγ mRNA was induced in both 3T3-L1 preadipocytes and adipocytes which ectopically express ADD-1. The effect of retroviral infection was more pronounced in 3T3-L1 adipocytes relative to preadipocytes. Interestingly, ADD-1-403, which lacks the membrane anchoring domain, was significantly more active in inducing PPARγ expression. These results suggest that the adipogenic effects of ADD-1/SREBP-1 previously demonstrated (Kim and Spiegelman, *Genes & Dev.* 10: 1096–1107 (1996)) are at least in part due to an up-regulation of the PPARγ gene expression.

c. PPARγ Expression is Induced in Cells Grown Under Conditions which Stimulate ADD-1/SREBP-1 Activity.

Next, the possibility that PPARγ was also induced under more physiological conditions, associated with activation of ADD-1/SREBP-1, was evaluated. To do this we quantified the relative expression of PPARγ protein by western blot analysis in undifferentiated 3T3-L1 and Hep G2 cells grown in medium containing different cholesterol concentrations (Wang et al., *Cell* 77:53–62 (1994)). In both cell lines, PPARγ protein was significantly induced upon cholesterol depletion for 24 hours, a condition known to enhance the production of mature and active ADD-1/SREBP-1 (Sakai et al., *Cell* 85:1037–1046 (1996); Wang et al., *Cell* 77:741–750 (1994)). Interestingly, PPARγ protein levels were decreased acutely by readdition of cholesterol (10 μM) and 25-hydroxycholesterol (1 μM) to the culture medium for 6 hours. These results suggest that PPARγ expression is subject to a tight and fast control by alterations in intracellular cholesterol levels.

Treatment with HMG-CoA reductase inhibitors, which inhibit the enzyme responsible for the rate-limiting step of cholesterol synthesis, provide another way to modify cellular cholesterol levels. Upon treatment, with compounds such as compactin or simvastatin, cells will become cholesterol depleted and the production of the active forms of ADD-1/SREBP-1 will increase (Sakai et al., *Cell* 85:1037–1046 (1996); Shimomura et al., *Proc. Natl. Acad. Sci. USA* 94:12345–12359 (1997)). Therefore, the expression of PPARγ protein was evaluated in Hep G2 cells before and after treatment with the potent HMG-CoA reductase inhibitor, simvastatin. Treatment of the cells with simvastatin ($5\times10^{-7}$ M) during 6 hours resulted in a robust and fast induction of PPARγ protein levels (4-fold), which was sustained 12 hours after addition.

d. PPARγ Activity is Stimulated by Activation of ADD-1/SREBP-1.

Next we wanted to assess whether the above-mentioned changes in PPARγ expression were associated with changes in the capabilities of PPARγ to transactivate. A PPRE-driven luciferase reporter gene, containing three copies of the apo A-II J site (Vu-Dac et al., 1995), ie. J3-TK-LUC, was transfected into rabbit kidney-derived RK-13 cells and half of the cells were maintained in cholesterol-depleted medium whereas the other half was grown in the same medium supplemented with a mixture of cholesterol and 25-hydroxycholesterol. In both conditions increasing amounts of the synthetic PPARγ ligand, BRL 49,653, were added to the medium, resulting in a dose-dependent activation of promoter activity by BRL 49,653. Under conditions of cholesterol depletion, the reporter gene was, however, activated to a significantly higher level. In fact, the BRL 49,653 dose-response curve was shifted proportionally, keeping the slope constant and suggesting that the observed effect of cholesterol depletion was the result of an increased expression of the PPARγ protein. Similar results were obtained when 3T3-L1 and ob-1771 preadipocyte cells were used. In order to exclude the possibility that the observed effect was specific for the apo A-II PPRE, we performed a cotransfection experiment using a different luciferase reporter driven by a single copy of the PPRE from the acyl CoA oxidase (ACO) gene (ACO-TK-LUC; (Osumi et al., *Biochem. Biophys. Res. Commun.* 175:866–871 (1991)). Also the activity of the ACO-TK-LUC reporter was significantly induced by cholesterol depletion.

Finally, to demonstrate that ADD-1/SREBP-1 was mediating the observed increase in PPARγ activity, the J3-TK-LUC reporter vector was cotansfected in 3T3-L1 cells together with an empty expression vector or an expression vector coding for either a constitutively active form of ADD-1, or a dominant negative form of ADD-1. When cells were cotransfected with the empty parental expression vector, a significant 1.5-fold induction of the luciferase activity was observed when the medium was depleted in cholesterol. In contrast, no effect of cholesterol depletion could be observed when cells were cotransfected with the dominant negative form of ADD-1, suggesting that the increased activity of PPARγ in response of cholesterol depletion is mediated by ADD-1/SREBP-1. A significant, but somehow less important inductive effect of cholesterol depletion was observed when the cells were cotransfected with the constitutively active form of ADD-1, indicating that under this condition PPARγ activity was at the limit of saturation.

TABLE I

Oligonucleotides used in this study listed from 5' to 3'.

| Name | Sequence ID No. | Sequence |
|---|---|---|
| LF-2 | 4 | TCTCCGGTGTCCTCGAGGCCGACCCAA |
| LF-14 | 5 | AGTGAAGGAATCGCTTTCTGGGTCAAT |
| LF-18 | 6 | AGCTGATCCCAAAGTTGGTGGGCCAGA |
| LF-20 | 7 | CATTCCATTCACAAGAACAGATCCAGTGGT |
| LF-21 | 8 | GGCTCTTCATGAGGCTTATTGTAGAGCTGA |
| LF-22 | 9 | GCAATTGAATGTCGTGTCTGTGGAGATAA |
| LF-23 | 10 | GTGGATCCGACAGTTAAGATCACATCTGT |
| LF-24 | 11 | GTAGAAATAAATGTCAGTACTGTCGGTTTC |
| LF-25 | 12 | TCGATATCACTGGAGATCTCCGCCAACAG |
| LF-26 | 13 | ACATAAAGTCCTTCCCGCTGACCAAAGCAA |
| LF-27 | 14 | CTCTGCTCCTGCAGGGGGGTGATGTGTTT |
| LF-28 | 15 | GAAGTTCAATGCACTGGAATTAGATGACA |
| LF-29 | 16 | GAGCTCCAGGGGTTGTAGCAGGTTGTCTT |
| LF-33 | 17 | GACGGGCTGAGGAGAAGTCACACTCTGA |
| LF-35 | 18 | AGCATGGAATAGGGGTTTGCTGTAATTC |
| LF-36 | 19 | TAGTACAAGTCCTTGTAGATCTCC |
| LF-44 | 20 | GTCGGCCTCGAGGACACCGGAGAG |
| LF-58 | 21 | CACTCATGTGACAAGACCTGCTCC |
| LF-59 | 22 | GCCGACACTAAACCACCAATATAC |
| LF-60 | 23 | CGTTAAAGGCTGACTCTCGTTTGA |
| AII J PPRE | 24 | GATCCTTCAACCTTTACCCTGGTAGA |
| ACO PPRE | 25 | GATCCCGAACGTGACCTTTGTCCTGGTCCC |
| LPL PPRE | 26 | GATCCGTCTGCCCTTTCCCCCTCTTCA |
| γ AS | 27 | GCATTATGAGCATCCCCAC |
| γS | 28 | TCTCTCCGTAATGGAAGACC |
| γ2S | 29 | GCGATTCCTTCACTGATAC |
| CDS | 30 | TTCTAGAATTCAGCGGCCGC(T)30(G/A/C)(G/A/C/T) |

Table II

Intron-exon boundaries of the PPARγ exons
The nucleotides in the exon are indicated in uppercase letters, whereas the flanking nucleotides in the intron are in lowercase. The approximate size of the introns is indicated in kilobases, and the exact length in base pairs of the exons is indicated between brackets. Amino acids encoded by the nucleotides flanking the intron/exon border are indicated by their letter symbol. The stop codon is indicated by an asterisk.

| Exon (bp) | Donor/ (SEQ ID NO.) | Intron in kb | Acceptor/ (SEQ ID NO.) | Exon |
|---|---|---|---|---|
| A1 (97) | CGCAG gtcagagt... (43) | >20 | ...ttgttaag ATTTG (44) | A2 |
| A2 (74) | TAACG gtaagtaa... (45) | >20 | ...cctttcag AA ATG (46)<br>M | 1 |
| B (211) | CAA G gtaaagtt... (47)<br>Q | 21 | ...cctttcag AA ATG (48)<br>E M | 1 |
| 1 (231) | CAA A gtatgatg... (49)<br>Q | 1.6 | ...atacacag GT GCA (50)<br>S A | 2 |
| 2 (170) | C AAG gtaattaa... (51)<br>K | 9.5 | ...ctttgcag GGT T (52)<br>G | 3 |
| 3 (139) | AAT G gtaagtaa... (53)<br>N | 10.7 | ...ctctatag CC ATC (54)<br>A I | 4 |
| 4 (203) | A TCA gttagttc... (55)<br>S | 10 | ...atttgcag CCA T (56)<br>P | 5 |
| 5 (451) | GGA G gtaagatt... (57)<br>G | 16.3 | ...ttccccag AC CGC (58)<br>D R | 6 |
| 6 (248) | TAG TAG cagaga... (59)<br>Y * | | | |

F. Materials and Methods

1. Isolation of the Human PPARγ cDNA and Gene, Restriction Mapping, Determination of Intron/Exon Boundaries, and DNA Sequencing A human adipose tissue lambda gt11 library was screened with a random primed 32P-labeled 200 bp fragment, covering the DNA-binding domain of the mouse PPARγ cDNA. After hybridization, filters were washed in 2×SSC, 0.1% SDS for 10 min at 20° C. and twice for 30 min in 1×SSC, 0.1% SDS at 50° C. and subsequently exposed to x-ray film (X-OMAT-AR, Kodak). Of several positive clones, one clone 407 was characterized in detail. The insert of this clone, starting ±90 bp upstream of the ATG start codon and extending downstream into the 3'-untranslated region (UTR) sequence, was subcloned in the EcoRI site of pBluescript SK—to generate clone 407.2. Sequence analysis of 407.2 confirmed it as being the human homologue of the mouse PPARγ2 cDNA. While this work was in progress, other groups also reported the isolation of human PPARγ2 cDNA clones (34, 35).

To isolate genomic P1-derived artificial chromosome (PAC) clones containing the entire human PPARγ gene, the primer pair LF-3 and LF-14 was used to amplify an 86-bp probe with human genomic DNA as template. This fragment was then used to screen a PAC human genomic library from human foreskin fibroblasts. Three positive clones, P-8854, P-8855, and P-8856, were isolated. Restriction digestion and Southern blotting were performed according to classical protocols as described by Sambrook et al. (36). Sequencing reactions were performed, according to the manufacturer instructions, using the T7 sequencing kit (Pharmacia Biotech Inc.).

2. Determination of the Transcription Initiation Sites: Primer Extension and 5'-Rapid Amplification of cDNA Ends (5'-RACE)

a. Primer Extension

The oligonucleotide LF-35 was 32P-labeled with T4-polynucleotide kinase (Amersham Life Science, Inc) to a specific activity of 107 dpm/50 ng and purified by gel electrophoresis. For primer extension, 105 dpm of oligonucleotide was added in a final volume of 100 μl to 50 μg of adipose tissue total RNA isolated from different patients. Primer extension analysis was performed following standard protocols utilizing a mixture of 1.25 units of avian mycloblastosis virus reverse transcriptase (Life Technologies, Inc.) and 100 units of Moloney murine leukemia virus reverse transcriptase (Life Technologies, Inc.). A sequencing reaction and molecular mass standards were used to map the 5'-end of the extension products.

b. 5'-RACE

The Marathon cDNA amplification kit (CLONTECH) was used to obtain a library of adaptor-ligated double-stranded cDNA from human adipose tissue. 1 μg of poly (A)+ RNA was used as a template for the first strand synthesis, with the 52-mer CDS primer and 100 units of the MMLV reverse transcriptase in a total volume of 10 μl. Synthesis was carried out at 42° C. for 1 h. Next, the second strand was synthesized at 16° C. for 90 min in a total volume of 80 μl containing the enzyme mixture (RNase H, *Escherichia coli* DNA polymerase I, and *E. coli* DNA ligase), the second strand buffer, the dNTP mix, and the first strand reaction. cDNA ends were then made blunt by adding to the reaction 10 units of T4 DNA polymerase and incubating at 16° C. for 45 min. The double-stranded cDNA was phenol/chloroform extracted, ethanol precipitated, and resuspended in 10 μl of water. Half of this volume was used to ligate the adaptor to the cDNA ends (adaptor sequence (SEQ ID NO: 60) CTAATACGACTCACTATAGGGCTC-GAGCGGCCGCCCGGGCAGGT) in a total volume of 10 μl using 1 unit of T4 DNA ligase. The ligation reaction was incubated 16 h at 16° C. The resulting cDNA library was diluted to a final concentration of 0.1 mg/ml.

The 5'-end of PPARγ1 PCR-amplified using 5 μl of the library as a template with the oligonucleotides AP-1 (binding to the adaptor) and LF-45 (binding antisense to the 5'-end of the PPARγ1). After an initial denaturing step at 95° C. for 3 min, 25 cycles were done at the following conditions: 10 s at 95° C., 20 s at 60° C., and 30 s at 72° C. The resulting PCR product was reamplified for 30 additional cycles at the same conditions using the nested oligonucleotides AP2 (nested to AP1) and LF-2 (nested to LF-45). The PCR product was analyzed on a 2% agarose gel, treated with Pfu polymerase (Stratagene) and cloned into the EcoRV site of pBluescript SK+. A total of 20 white colonies were grown and sequenced from both ends using the oligonucleotides T3 and T7 (Dye Terminator Cycle sequencing kit, Applied Biosystems).

For the determination of the 5'-end of PPARγ 2, the same procedure was followed except that the oligonucleotide LF-14 (specific for the PPARγ2 5'-UTR) was used in the first round PCR, and the oligonucleotide LF-35 (nested to LF-14) was used in the second round PCR with the same cycling conditions.

3. Tissue Biopsies and Cell Culture

Omental adipose tissue, small and large intestine, kidney, muscle, and liver biopsies were obtained from non-obese adult subjects undergoing elective surgery or endoscopy. All subjects had fasted overnight before surgery (between 8.00 p.m. and 10 a.m.) and received intravenous saline infusion. They had given informed consent, and the project was approved by the ethics committee of the University of Lille. All tissue was immediately frozen in liquid nitrogen until RNA preparation.

Standard cell culture conditions were used to maintain 3T3-L1 (obtained from ATCC), CV-1 (a kind gift from Dr. R. Evans, Salk Institute, La Jolla, Calif.), and Hep G2 cells (ATCC). BRL-49,653, supplied by Ligand Pharmaceuticals, San Diego, Calif. (in DMSO) and fatty acids (in ethanol) were added to the medium at the concentrations and times indicated. Control cells received vehicle only. Fatty acids were complexed to serum albumin contained in delipidated and charcoal-treated fetal calf serum by preincubation for 45 min at 37° C.

In Example 1, standard cell culture conditions were used to maintain 3T3-L1 (obtained from ATCC), HeLa (ATCC), CaCo2 (ATCC), RK-13 (ATCC), THP-1 (ATCC), and Hep G2 cells (ATCC). BRL 49,653 and simvastatin were dissolved in DMSO and cholesterol and 25-hydroxycholesterol in ethanol. Control cells received vehicle only. Retroviral infection of 3T3-L1 cells was performed as described previously (Kim and Spiegelman, *Genes & Dev.* 10:1096–1107 (1996)). Briefly, the BOSC23 cell line was transiently transfected with the recombinant retroviral vectors pBabe, ADD-1-403, and ADD-1 (Kim and Spiegelman, *Genes & Dev.* 101096–1107 (1996)) using the calcium phosphate method. Viral supernatants were collected 48 hours after transfection and titrated. 3T3-L1 cells were incubated with retrovirus for 5 hours in the presence of 4 μg/ml of polybrene. Cells were then subcultured (1:3) for 2 days after infection in medium containing puromycin (2 μg/ml) for selection. Differentiation of 3T3-L 1 cells was as described previously (Lin and Lane, *Genes & Dev.* 6:533–544 (1992)).

4. mRNA Analysis by RT-Competitive PCR Assay

RNA preparation of total cellular RNA was performed as described previously (37). The absolute mRNA concentration of the differentially spliced PPARγ variants was measured by reverse transcription reaction followed by competitive polymerase chain reaction (RT-competitive PCR) in the presence of known amounts of competitor DNA yielding amplicons of different size allowing the separation and the quantification of the PCR products. The competitor was constructed by deletion of a 74-bp fragment (nucleotides +433 to +507 by HindIII digestion) of PPARγ1 cloned into pBluescript KS+, yielding pBSCompPPARγ. Working solution of the competitor was prepared by in vitro transcription followed by serial dilution in 10 mM Tris-HCl (pH 8.3), 1 mM EDTA buffer. For RT-competitive PCR, the antisense primer hybridized to the 3'-end of exon 3 (gammaAS: 5'-GCATTATGAGCATCCCCAC-3', nt +600 to +620 SEQ ID NO: 27) and the sense primer to exon 1 (gammaS: 5'-TCTCTCCGTAATGGAAGACC-3', nt +146 to +165 SEQ ID NO: 28) or to the B exon (gamma2S: 5'-GCGAT-TCCTTCACTGATAC-3', nt +41 to +59 SEQ ID NO: 29). Therefore, the same competitor served to measure either total PPARγ mRNAs (γ1+γ2; with primers gamma AS and gamma S) or, specifically, PPARγ2 mRNA (with primers gamma AS and gamma 2S). The gamma AS/gamma S primer pair gave PCR products of 474 and 400 bp for the PPARγ mRNAs and competitor, respectively. The primer pair gammaAS/gamma2S gave 580 bp for PPARγ2 mRNA and 506 bp for the competitor. For analysis of the PCR products, the sense primers gamma S and gamma2S were 5'-end labeled with the fluorescent dye Cy-5 (Eurogentec, Belgium).

First-strand cDNA synthesis was performed from total RNA (0.1 μg) in the presence of the antisense primer gamma AS (15 pmol) and of thermostable reverse transcriptase (2.5 units; Tth DNA polymerase, Promega) as described (38). After the reaction, half of the RT volume was added to the PCR mix (90 μl) containing the primer pair gamma AS/gamma S for the assay of PPARγ total mRNA, whereas the other half was added to a PCR mix (10 mM Tris-HCl, pH 8.3, 100 mM KCl, 0.75 M EGTA, 5% glycerol, 0.2 mM dNTP, 5 units of Taq polymerase) containing the primer pair gammaAS/gamma2S for the assay of PPARγ2 mRNA. Four aliquots (20 μl) of the mixture were then transferred to microtubes containing a different, but known, amount of competitor. After 120 s at 95° C., the samples were subjected to 40 PCR cycles (40 s at 95° C., 50 s at 55° C., and 50 s at 72° C.). The fluorescent-labeled PCR products were analyzed by 4% denaturing polyacrylamide gel electrophoresis using an automated laser fluorescence DNA sequencer (ALFexpress, Pharmacia, Uppsala, Sweden), and integration of the area under the curve using the Fragment manager software (Pharmacia) was performed as described (38).

To validate this technique, human PPARγ2 mRNA was synthesized by in vitro transcription from the expression vector pSG5hPPARγ (Riboprobe system, Promega) and quantified by competitive PCR over a wide range of concentrations (0.25–25 attomole (amol) added in the RT reaction). Standard curves were obtained in assaying PPARγ total mRNA or PPARγ2 mRNA. The linearity (r=0.99) and the slopes of the standard curves (0.98 and 1.11) indicated that the RT-competitive PCR is quantitative and that all the mRNA molecules are copied into cDNA during the RT step. The lower limit of the assay was about 0.05 amol of mRNA in the RT reaction, and the interassay variation of the RT-competitive PCR was 7% with six separated determinations of the same amount of PPARγ mRNA.

5. Western Blot Analysis of PPARγ

Cells and tissues were homogenized in a lysis buffer of PBS containing 1% Triton X-100 (Sigma). Tissues were homogenized in extraction buffer containing PBS and 1% Nonidet P-40 (Sigma), 0.5% sodium deoxycholate (Sigma), 0.1% SDS (Sigma). Fresh mixture protease inhibitor (ICN) was added (100 mg/ml AEBSF, 5 mg/ml EDTA, 1 mg/ml leupeptin, 1 mg/ml pepstatin). Protein extracts were obtained by centrifugation of the lysate at 4° C., and concentration was measured with the Bio-Rad DC Protein colorimetric assay system.

Protein (100 μg) was separated by SDS-PAGE, transferred to nitrocellulose membrane (Amersham Life Science, Inc.), and blocked overnight in blocking buffer (20 mM Tris, 100 mM NaCl, 1% Tween-20, 10% skim milk). Filters were first incubated for 4 h at room temperature with rabbit IgG anti-mPPARγ (10 mg/ml), raised against an N-terminal PPARγ peptide (amino acids 20–104), and next developed for 1 h at room temperature with a goat anti-rabbit IgG (whole molecule) peroxidase conjugate (Sigma) diluted at 1/500. The complex was visualized with 4-chloro-1-naphtol as reagent.

In Example 1, the membranes were blocked overnight in blocking buffer (20 mM Tris, 100 mM NaCl, 1% Tween-20, 10% skim milk). Filters were first incubated 4 hours at 21° C. with either a rabbit IgG anti-mPPARγ (10 mg/ml) (Fajas et al., *J. Biol. Chem.* 272:18779–18789 (1997)) or a rabbit IgG anti-mSREBP-1 antibody (Santa Cruz, Calif.), and then for 1 hour at 21° C. with a goat anti-rabbit IgG (whole molecule) peroxidase conjugate diluted at 1/5000. The complex was visualized with 4-chloro-1-naphtol as reagent.

6. Analysis of Promoter Activity

To test the activity of the human PPARγ promoters several reporter constructs were made.

A 1-kb fragment of PAC clone 8856 was isolated by PCR using the oligonucleotides LF-35 (binding antisense in the PPARγ2 5'-UTR) and the oligonucleotide LF-58 (binding sense at position −1000 of the PPARγ2), was sequenced, and was inserted into EcoRV site of pBluescript (Stratagene, La Jolla, Calif.). After digestion of plasmid pBS γ2p1000 with SmaI and KpnI, the insert was cloned into the reporter vector pGL3 (Promega), creating the expression vector pGL3γ2p1000.

To isolate the PPARγ1 promoter, an 8-kb EcoRI fragment, which hybridized with the oligonucleotide LF-2 (corresponding to the 5'-UTR of γ1), was cloned into pBluescript. Partial mapping and sequencing of this clone revealed the presence of a 3-kb fragment upstream of the transcription initiation site. To test for promoter activity, a SacI/XhoI digestion of this clone containing the 3-kb promoter was inserted in the same sites of pGL3, resulting in the final vector pGL3 γ1p3000. The pSG5-haPPARγ (39) and pMSV-C/EBPβ (10) expression vectors were described elsewhere.

Transfections were carried out in 60-mm plates using standard calcium phosphate precipitation techniques (for 3T3-L1, CV-1, and COS cells) (22). Luciferase and α-galactosidase assays were carried out exactly as described previously (22).

The PAC clone P-8856 (Fajas et al., *J. Biol. Chem.* 272:18779–18789 (1997)), containing the full lenght PPARγ gene, was also sequenced with the oligonucleotides LF-60 and LF-63 pointing upstream of exon A2. A 800 bp fragment of the PAC clone 8856 was isolated by PCR using the amplimers LF-60 (binding to the antisense strand in exon A2) and LF-68 (binding sense at position −800 of the PPARγ3 promoter). This PCR fragment was sequenced, inserted into the EcoRV site of pBluescript SK+ (Stratagene, La Jolla, USA), and after SpeI and KpnI restriction subcloned into pGL3 (Promega, Madison, USA), creating the reporter vector pGL3γ3p800.

Site-directed mutagenesis of the E-box in the PPARγ3 promoter was performed by splicing overlapping ends polymerase chain reaction (Ho, et al., *Gene* 77:51–59 (1989)), using the oligo pairs LF-106/LF-60 and LF-107/LF-68, to generate the plasmid pGL3γ3p800-E-boxmut. This changed the three bases underlined in the sequence 5'-ATTCATGTGACAT-3' to 5'-ATTCATGCATCAT-3' (SEQ ID NOS: 41 and 42, respectively. The J3-TK-LUC (Vu-Dac et al., 1995) and ACO-TK-LUC (Osumi et al., *Biophys. Res. Commun.* 175:866–871 (1991)) luciferase reporter vectors and the expression vectors encoding for ADD-1, a dominant negative form of ADD-1, and SREBP-1a (Tontonoz et al., *Mol. Cell. Biol.* 13:4753–4759 (1993)); Yokoyama et al., *Cell* 75:187–197 (1993)) were described before. Transfections, luciferase and β-galactosidase assays were generally performed as described previously (Schoonjans et al., *J. Biol. Chem.* 270:19269–19276 (1995)). To analyze the effect of cholesterol depletion in transfection experiments, the cells were divided in two pools after transfection. Half of the transfected cells were incubated with delipidated medium, whereas the other half of the cells were incubated with the same medium supplemented with a mixture of 10 μM cholesterol and 1 μM of 25-hydroxycholesterol.

7. Electrophoretic Mobility Shift Assays (EMSA) and Oligonucleotide Sequences haPPARγ (39), hPPARγ2, and mRXRα (40) proteins were synthesized in vitro in rabbit reticulocyte lysate (Promega). Molecular weights and quality of the in vitro translated proteins were verified by SDS-PAGE. PPAR (2 μl) and/or RXR (2 μl) were incubated for 15 min on ice in a total volume of 20 μl with 1-ng probe, 2.5 μg of poly(dI-dC) and 1 μg of herring sperm DNA in binding buffer (10 mM Tris-HCl pH 7.9, 40 mMKCl, 10% glycerol, 0.05% Nonidet P-40, and 1 mM dithiothreitol). For competition experiments, increasing amounts (from 10- to 200-fold molar excess) of cold oligonucleotide (AII-J-PPRE, 5'-GATCCTTCAACCTTTACCCTGGTAGA-3' (41) SEQ ID NO: 24; acyl-CoA oxidase (ACO)-PPRE, 5'-GATCCCGAACGTGACCTTTGTCCTGGTCCC-3' (42) SEQ ID NO: 25; or LPL-PPRE, 5'-GATCCGTCTGCCCTTTCCCCCTCTTCA-3 (23) SEQ ID NO: 26; were included just before adding T4-PNK end-labeled AII-J-PPRE oligonucleotide. DNA-protein complexes were separated by electrophoresis on a 4% polyacrylamide gel in 0.25×TBE buffer at 4° C. (43).

In Example 1, the SREBP-1a protein was produced in a baculovirus system and ADD-1 was produced by in vitro transcription. Quality of the produced proteins were verified by SDS-PAGE. Proteins were incubated for 15 min on ice in a total volume of 20 μl μl with 1 ng of T4-PNK end-labelled double-stranded oligonucleotide containing the PPARγ3 E-box (LF-102), 2.5 μg poly (dI:dC) and 1 μg herring sperm DNA in binding buffer (10 mM Tris-HCl (pH 7.9), 40 mM KCl, 10% glycerol, 0,05% Nonidet P-40 and 1 mM DTT). For competition experiments, increasing amounts of cold double-stranded oligonucleotides (10, 50-, and 100-fold molar exces) corresponding to the PPARγ3 E-box, the consensus 3-hydroxy-3-methylglutaryl coenzyme A synthase SRE site (Smith et al., *J. Biol. Chem.* 263:18480–18487 (1988)), or the mutated PPARγ3 E-box (LF-106) were included just before adding labelled oligonucleotide. DNA-protein complexes were separated by electrophoresis on a 4% polyacrylamide gel in 0.25×TBE buffer at 4° C. (Fried and Crothers, *Nucl. Acids Res.* 11:141–158 (1983)).

8. RNA Isolation, Primer Extension, and RNase Protection Assays

In locating the promoter of PPARγ3, total cellular RNA was prepared as described previously (Saladin et al., *Nature* 377:527–529 (1995)). For primer extension, the oligonucleotide LF-60 was 32P-labelled with T4-polynucleotide kinase (Amersham, Courtaboeuf, France) to a specific activity of 107 dpm/50 ng and purified by gel electrophoresis. Primer extension analysis was performed using 50 μg of total RNA and 105 dpm of radiolabelled oligonucleotide according to a standard protocol utilizing a mixture of 1.25 U AMV reverse transcriptase (Life technologies, Paisley, UK) and 100 U MMLV reverse transcriptase (Life technologies, Paisley, UK). A sequencing reaction was used as molecular mass standard to map the 5' end of the extension products.

The absolute mRNA concentration of the differentially spliced PPARγ variants was measured by RNase protection assay exactly as described (Lemberger et al., *J. Biol. Chem.* 271:1764–1769 (1995)). The full lenght PPARγ2 coding region plus 33 bp of the 5' UTR was amplified from human adipose tissue RNA by RT-PCR with the primer pair LF-3/LF-36 and was inserted in the inverted orientation (3' to 5' in front of the T7 promoter) into the EcoRI site of the expression vector pSG5 (Stratagene, La Jolla, Calif.). The resulting plasmid pSG5-hPPARγ2-inv was digested with EcoRV and religated, yielding the vector pSG5-hPPARγ2-RPA, which was used as a template for the synthesis of the anti-sense RNA probe, to measure the relative amounts of PPARγ2 relative to PPARγ1 and 3 mRNA. For the specific analysis of the PPARγ3 mRNA relative to PPARγ1, another probe template was constructed by RT-PCR from human adipose tissue RNA with the primer pair LF-44 (which binds to the sense strand in exon A1) and LF-21 (which binds to the antisense strand in the exon 2). The amplified fragment, which contains part of exon A1, the full lenght exon A2, exon 1, and part of exon 2, was inserted into the EcoRV site of pBluescript SK+ to generate the plasmid pBSγ3-RPA. For the analysis of mouse PPARγ RNA, mPPARγ cDNA was amplified, using the same strategy and oligonucleotides described above to create the vector pSG5-mPPARγ2-inv. This plasmid was digested by EcoRI and religated resulting in the plasmid pSG5-mPPARγ-RPA. The in vitro synthetized probe contains part of the exons 4 and 5 of the mPPARγ gene.

G. Candidate PPARγ Modulators

The following molecules and their derivatives and homologs are candidate PPARγ modulators:

(1) HMG-CoReductase inhibitors, including, but not limited to, simvastatin, atorvastatin, pravastatin, and fluvastatin, (2) Cholesterol and its metabolites such as the various oxysterols, (3) Insulin and insulin mimetics, (4) Glucocorticoid hormones, including, but not limited to, cortisol, and dexamethasone, (5) Oxidized low density lipoproteins and their lipid components, (6) Agonists of receptors in the JAK-STAT pathway. Such agonists include, but are not limited to, growth hormone, prolactin, leptin, and macrophage-cology stimulating factor (M-CSF), and (7) Phorbolesters such as PMA, and agonists of the cAMP pathway such as forskolin and dibutyryl cAMP.

Other candidate agents glucocorticoids; thyroid hormones; thyromimetics; fibrates, free fatty acids and other agonists of PPAR including Di-(2-ethylhexyl)-phthalate, plasticizers and herbicides including 2, 4, 5-trichlorophenoxyacetic acid and leukotriene antagonists; antagonists of PPAR and PPAR subtype selective compounds; RAR selective agonists and antagonists including subtype selective compounds; RXR selective agonists and antagonists including subtype selective compounds; estrogens and other agonists and antagonists of ER; androgens and other agonists and antagonists of AR; progestins and other agonists and antagonists of PR; non-steroid progestins; mineralocorticoids and other agonists and antagonists of MR; insulin; glucose; glucagon; free fatty acids; amino acids; sugars and other secretagogues including biguanides; antidiabetics including metformin and phenformin; pyroglyrides; linoglyrides and benzothenediones; non-steroidal anti-inflammatory drugs; prostacyclins; prostaglandins; dihydroepiandosterone and stimulators, precursors and derivatives thereof including Dioscorea and aloe vera, and extracts and compounds derived therefrom; tumor necrosis factors; cytokines and related signaling molecules; growth factors; fetuin; Amylin agonists and antagonists; prolactin; niacin; Acepimox and other nicotinic acid derivatives; triacsins; amphetamines and derivatives including fenfluramine and dexfenfluramine; endorphin antagonists; somatostatin; cholecystokinin; bombesin; gastrin; oral anti-diabetic agents; corticotropin releasing hormone; thiazolidinedione compounds; adrenocorticotropic hormones; melanocyte stimulating hormone; gastric inhibitory peptide; growth hormone agonists and antagonists; α and β adrenergic agonists and antagonists including phenoxybenzamide; fluloxetine; neuropeptide Y and modulators of its activity or expression; and the gene products of agouti and GLP-1.

H. Utility of PPARγ Modulators

A transcription modulator of PPARγ can be used to treat or prevent disorders involving tissues in which PPARγ is expressed. The PPARγ gene modulators identified by the methods of this invention can be used to control a variety of physiological or biochemical conditions in animals (esp. mammals) such as the level of metabolism, body weight, food intake, oxygen consumption, body temperature, serum insulin level, serum glucose level, and body fat content (versus muscle content). Such modulators are useful in treating a host with an abnormal level of PPARγ gene expression, as well as those having normal levels of PPARγ gene expression. The PPARγ gene modulators can also be used to treat diseases and conditions affected by the level of PPARγ gene expression. The modulators are useful in mimicking human diseases or conditions in animals relating to the level of PPARγ gene expression. The modulators can be used in experimental testing of PPARγ gene modulators for veterinary uses, including, but not limited to, controlling the body weight of animals and the fat content of meat.

As we discussed above, PPARγ regulates adipose tissue differentiation. In that regard, a transcription modulator of PPARγ can be used to treat or prevent diseases associated with abnormalities of adipose tissue or adipocytes, including, but not limited to, obesity, anorexia, cachexia, lipodystrophy, lipomas, liposarcomas, and abnormalities of adipose tissue associated with anti-HIV treatment.

It has been known that PPARγ agonists improve insulin sensitivity and ameliorate glucose homeostasis and certain aspects of metabolism (see WO 97/10819, incorporated by reference herein in its entirety). PPARγ transcription modulators can be used to achieve similar pharmaceutical effects. In that regard, this invention relates to methods of identifying transcription modulators and using such modulators to treat or prevent insulin resistance, diabetes mellitus (NIDDM), and conditions associated with insulin resistance such as polycystic ovary syndrome and lipodystrophy.

In a related application (PCT/US98/05852, incorporated by reference herein in its entirety), we showed that PPARγ is strongly expressed in certain regions of the bowel and it plays a role in modulating gastrointestinal (GI) function and the development of GI tract cancer. In that regard, a transcription modulator of PPARγ can be used to treat or prevent diseases of the GI tract, including, but not limited to, inflammatory bowel disease (e.g. Crohn's disease and ulcerative colitis), bowel cancer, irritable bowel syndrome, and ulcerations of the GI tract.

PPARγ is expressed in macrophages and its expression is induced in foam cells, which are the initial cells of the atherosclerotic lesion (see Tontonoz P, et al., *Cell* 93(2): 241–252 (1988); Nagy L, et al., *Cell* 93(2): 229–240 (1988); and Ricote M, et al., *Proc Natl Acad Sci USA* 95(13): 7614–7619 (1988)). In addition, activation of PPARγ affects lipid levels in the blood and can reverse atherogenic lipid profiles. In that regard, a transcription modulator of PPARγ can be used to treat or prevent hyper- and dyslipidemia, including but not limited to hypertriglyceridemia and hypoalpha lipoproteinemia, atherosclerosis, and other vascular diseases.

We have observed that PPARγ is highly expressed in eosinophils, which are involved in inflammatory and allergic responses. In addition, PPARγ is highly expressed in other cells involved in host defense such as macrophages and neutrophils. Modulation of PPARγ could affect these crucial cells and their role in immune and inflammatory reaction. Furthermore, the PPARγ promoter contains several elements that are responsive to transcription factors activated under inflammatory conditions (such as STATs, NF-kB, C/EBP-beta, and AP-1). In that regard, a transcription modulator of PPARγ can be used to treat or prevent acute inflammation (e.g., septic shock, and infection), chronic inflammation (e.g., inflammatory bowel disease, and rheumatoid arthritis), allergic conditions including conditions involving skin (e.g., urticaria and eczema) and lungs (asthma), immulogic disorders (e.g., graft versus-host disease), parasitic infections, bacterial infections, and viral infections.

Because PPARγ is highly expressed in cells involved in host defense, a modulator of PPARγ expression can be used to enhance the host defense against malignant diseases, including, but not limited to, cancers such as cancer of the breast, prostate, and colon.

Accumulation of fat tissue in bone marrow is a common problem associated with or involved in the pathogenesis of osteoporosis and bone loss. In that regard, PPARγ modulators (esp. a down modulator) can be used to prevent or treat osteoporosis and bone loss.

PPARγ is involved in the differentiation of surfactant producing cells in the lung. By changing PPARγ expression in these cells, PPARγ modulators can be used to treat or prevent pulmonary disorders associated with abnormal surfactant production (e.g., ARDS and RDS).

PPARγ is expressed in certain regions of the skin. In that regard, modulators of PPARγ can also be used to treat or prevent skin diseases involving those skin cells.

I. Pharmaceutical Formulations and Modes of Administration

The particular compound that affects the disorders or conditions of interest can be administered to a patient either by themselves, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

The compounds also can be prepared as pharmaceutically acceptable salts. Examples of pharmaceutically acceptable salts include acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. (See e.g., PCT/US92/03736). Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipients can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols and physiologically compatible solvents. In addition, the molecules tested can be used to determine the structural features that enable them to act on the ob gene control region, and thus to select molecules useful in this invention. Those skilled in the art will know how to design drugs from lead molecules, using techniques such as those disclosed in PCT publication WO 94/18959, incorporated by reference herein.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Some methods of delivery that may be used include:

a. encapsulation in liposomes, b. transduction by retroviral vectors, c. localization to nuclear compartment utilizing nuclear targeting site found on most nuclear proteins, d. transfection of cells ex vivo with subsequent reimplantation or administration of the transfected cells, e. DNA transporter system.

All publications referenced are incorporated by reference herein, including the nucleic acid sequences and amino acid sequences listed in each publication. All the compounds disclosed and referred to in the publications mentioned above are incorporated by reference herein, including those compounds disclosed and referred to in articles cited by the publications mentioned above.

REFERENCES

1. Auwerx, J., Martin, G., Guerre-Millo, G., and Staels, B. (1996) J. Mol. Med. 74, 347–352
2. Flier, J. S. (1995) Cell 80, 15–18
3. Spiegelman, B. M., and Flier, J. S. (1996) Cell 87, 377–389
4. Moller, D. E., and Flier, J. S. (1991) N. Engl. J. Med. 325, 938–948
5. Auwerx, J., Schoonjans, K., Fruchart, J. C., and Staels, B. (1996) Atherosclerosis 124, (suppl.) S29–S37
6. Tontonoz, P., Hu, E., Graves, R. A., Budavari, A. I., and Spiegelman, B. M. (1994) Genes & Dev. 8, 1224–1234
7. Tontonoz, P., Hu, E., and Spiegelman, B. M. (1994) Cell 79, 1147–1156
8. Freytag, S. O., and Geddes, T. J. (1992) Science 256, 379–382
9. Freytag, S. O., Paielli, D. L., and Gilbert, J. D. (1994) Genes & Dev. 8, 1654–1663
10. Christy, R. J., et al. (1989) Genes & Dev. 3, 1323–1335
11. Wu, Z., Xie, Y., Bucher, N. L. R., and Farmer, S. R. (1995) Genes & Dev. 9, 2350–2363
12. Wu, Z., Bucher, N. L. R., and Farmer, S. R. (1996) Mol. Cell. Biol. 16, 4128–4136
13. Yeh, W. C., Cao, Z., Classon, M., and McKnight, S. (1995) Genes & Dev. 9, 168–181
14. Tontonoz, P., Kim, J. B., Graves, R. A., and Spiegelman, B. M. (1993) Mol. Cell. Biol. 13, 4753–4759
15. Kim, J. B., and Spiegelman, B. M. (1996) Genes & Dev. 10, 1096–1107
16. Schoonjans, K., Staels, B., and Auwerx, J. (1996) Biochim. Biophys. Acta 1302, 93–109
17. Schoonjans, K., Staels, B., and Auwerx, J. (1996) J. Lipid Res. 37, 907–925
18. Cornelius, P., MacDougald, O. A., and Lane, M. D. (1994) Annu. Rev. Nutr. 14, 99–129
19. Hu, E., Tontonoz, P., and Spiegelman, B. M. (1995) Proc. Natl. Acad. Sci. U.S.A. 92, 9856–9860
20. Tontonoz, P., Hu, E., Devine, J., Beale, E. G., and Spiegelman, B. M. (1995) Mol. Cell. Biol. 15, 351–357
21. Schoonjans, K., Staels, B., Grimaldi, P., and Auwerx, J. (1993) Eur. J. Biochem. 216, 615–622
22. Schoonjans, K., Watanabe, M., Suzuki, H., Mahfoudi, A., Krey, G., Wahli, W., Grimaldi, P., Staels, B., Yamamoto, T., and Auwerx, J. (1995) J. Biol. Chem. 270, 19269–19276 [Abstract/Full Text]
23. Schoonjans, K., Peinado-Onsurbe, J., Heyman, R., Briggs, M., Cayet, D., Deeb, S., Staels, B., and Auwerx, J. (1996) EMBO J. 15, 5336–5348
24. Brandes, R., Hertz, R., Arad, R., Naishtat, S., Weil, S., and Bar-Tana, J. (1987) Life Sci. 40, 935–941
25. Gharbi-Chibi, J., Teboul, M., Bismuth, J., Bonne, J., and Torresani, J. (1993) Biochem. Biophys. Acta 1177, 8–14
26. Amri, E.-Z., Bertrand, B., Ailhaud, G., and Grimaldi, P. (1991) J. Lipid Res. 32, 1449–1456
27. Chawla, A., and Lazar, M. A. (1994) Proc. Natl. Acad. Sci. U.S.A. 91, 1786–1790
28. Kliewer, S. A., Lenhard, J. M., Willson, T. M., Patel, I., Morris, D. C., and Lehman, J. M. (1995) Cell 83, 813–819
29. Forman, B. M., Tontonoz, P., Chen, J., Brun, R. P., Spiegelman, B. M., and Evans, R. M. (1995) Cell 83, 803–812
30. Gaillard, D., Negrel, R., Lagarde, M., and Ailhaud, G. (1989) Biochem. J. 257, 389–397
31. Negrel, R., Gaillard, D., and Ailhaud, G. (1989) Biochem. J. 257, 399–405
32. Aubert, J., Ailhaud, G., and Negrel, R. (1996) FEBS Lett. 397, 117–121
33. Brun, R. P., Tontonoz, P., Forman, B. M., Ellis, R., Chen, J., Evans, R. M., and Spiegelman, B. M. (1996) Genes & Dev. 10, 974–984
34. Elbrecht, A., Chen, Y., Cullinan, C. A., Hayes, N., Leibowitz, M. D., Moller, D. E., and Berger, J. (1996) Biochem. Biophys. Res. Commun. 224, 431–437
35. Lambe, K. G., and Tugwood, J. D. (1996) Eur. J. Biochem. 239, 1–7
36. Sambrook, J., Fritsch, E. F., and Maniatis, T. (1989) Molecular Cloning: A Laboratory Manual, Cold Spring Harbor Laboratory Press, Cold Spring Harbor, N.Y.
37. Saladin, R., De Vos, P., Guerre-Millo, M., Leturque, A., Girard, J., Staels, B., and Auwerx, J. (1995) Nature 377, 527–529
38. Vidal, H., Auboeuf, D., De Vos, P., Staels, B., Riou, J. P., Auwerx, J., and Laville, M. (1996) J. Clin. Invest. 98, 251–255 [Abstract/Full Text]
39. Aperlo, C., Pognonec, P., Saladin, R., Auwerx, J., and Boulukos, K. (1995) Gene (Amst.) 162, 297–302
40. Leid, M., Kastner, P., Lyons, R., Nakshatri, H., Saunders, M., Zacharewski, T., Chen, J. Y., Staub, A., Garnier, J. M., Mader, S., and Chambon, P. (1992) Cell 68, 377–395
41. Vu-Dac, N., Schoonjans, K., Kosykh, V., Dallongeville, J., Fruchart, J.-C., Staels, B., and Auwerx, J. (1995) J. Clin. Invest. 96, 741–750
b 42. Tugwood, J. D., Isseman, I., Anderson, R. G., Bundell, K. R., McPheat, W. L., and Green, S. (1992) EMBO J. 11, 433–439
43. Fried, M. G., and Crothers, D. M. (1983) Nucleic Acids Res. 11, 141–158
44. Kliewer, S. A., Forman, B. M., Blumberg, B., Ong, E. S., Borgmeyer, U., Mangelsdorf, D. J., Umesono, K., and Evans, R. M. (1994) Proc. Natl. Acad. Sci. U.S.A. 91, 7355–7359
b 45. Zhu, Y., Qi, C., Korenberg, J. R., Chen, X.-N., Noya, D., Rao, M. S., and Reddy, J. K. (1995) Proc. Natl. Acad. Sci. U.S.A. 92, 7921–7925
46. Lehmann, J. M., Moore, L. B., Smith-Oliver, T. A., Wilkison, W. O., Willson, T. M., and Kliewer, S. A. (1995) J. Biol. Chem. 270, 12953–12956 [Abstract/Full Text]
47. Berger, J., Bailey, P., Biswas, C., Cullinan, C. A., Doebber, T. W., Hayes, N. S., Saperstein, R., Smith, R. G., and Leibowitz, M. D. (1996) Endocrinology 137, 4189–4195
48. Willson, T. M., Cobb, J. E., Cowan, D. J., Wiethe, R. W., Correa, I. D., Prakash, S. R., Beck, K. D., Moore, L. B., Kliewer, S. A., and Lehmann, J. M. (1996) J. Med. Chem. 39, 665–668

49. Hulin, B., McCarthy, P. A., and Gibbs, E. M. (1996) Curr. Pharm. Des. 2, 85–102

50. Saltiel, A. R., and Olefsky, J. M. (1996) Diabetes 45, 1661–1669

51. Dreyer, C., Krey, G., Keller, H., Givel, F., Helftenbein, G., and Wahli, W. (1992) Cell 68, 879–887

52. Greene, M. E., Blumberg, B., McBride, O. W., Yi, H. F., Kronquist, K., Kwan, K., Hsieh, L., Greene, G., and Nimer, S. D. (1995) Gene Expr. 4, 281–299

53. Xue, J. C., Schwarz, E. J., Chawla, A., and Lazar, M. A. (1996) Mol. Cell. Biol. 16, 1567–1575

54. Mansen, A., Guardiola-Diaz, H., Rafter, J., Branting, C., and Gustafsson, J. A. (1996) Biochem. Biophys. Res. Commun. 222, 844–851

55. Giovanucci, E., and Willet, W. C. (1994) Ann. Med. 26, 443–452

56. Stenson, W. F., Cort, D., Rodgers, J., Burakoff, R., DeSchryver-Kecskemeti, K., Gramlich, T. L., and Beeken, W. (1992) Ann. Intern. Med. 116, 609–614

57. Belluzi, et al. (1996) N. Engl. J. Med. 334, 1557–15

All publications cited in the specification are incorporated by reference herein, including drawings and sequences listed in each publication. All the compounds disclosed and referred to in the publications mentioned above are incorporated by reference herein, including those compounds disclosed and referred to in articles cited by the publications mentioned above.

Other embodiments of this invention are disclosed in the following claims.

---

We claim:

1. An isolated or purified recombinant nucleic acid molecule, comprising a control region of a human peroxisome proliferators activated receptor gamma (PPARγ) gene, wherein the control region comprises nucleotides 1–125 of SEQ ID NO:1.

2. An isolated or purified recombinant nucleic acid molecule, comprising a control region of a human peroxisome proliferators activated receptor gamma (PPARγ) gene, wherein the control region comprises nucleotides 818–1320 of SEQ ID NO:3.

3. An isolated or purified recombinant nucleic acid molecule, comprising a control region of a human peroxisome proliferators activated receptor gamma (PPARγ) gene, wherein the control region comprises nucleotides 368–1144 of SEQ ID NO:34.

4. A isolated cell, comprising:

the nucleic acid molecule of claim 1; and a reporter sequence;

wherein the control region is operably linked to the reporter sequence so as to effectively initiate, terminate or regulate the transcription of the reporter sequence.

5. The cell of claim 4, wherein the reporter sequence encodes an enzyme that produces a detectable colorimetric or a fluorometric change in the cell.

6. The cell of claim 5, wherein the enzyme is selected from the group consisting of luciferase, a green fluorescent protein, chloramphenicol acetyl transferase, β-galactosidase, β-lactamase, secreted placental alkaline phosphatase, human growth hormone, an esterase, a phosphatase, tissue plasminogen activator and urokinase.

7. A isolated cell, comprising:

the nucleic acid molecule of claim 2; and a reporter sequence;

wherein the control region is operably linked to the reporter sequence so as to effectively initiate, terminate or regulate the transcription of the reporter sequence.

8. The cell of claim 7, wherein the reporter sequence encodes an enzyme that produces a detectable colorimetric or a fluorometric change in the cell.

9. The cell of claim 8, wherein the enzyme is selected from the group consisting of luciferase, a green fluorescent protein, chloramphenicol acetyl transferase, β-galactosidase, β-lactamase, secreted placental alkaline phosphatase, human growth hormone, an esterase, a phosphatase, tissue plasminogen activator and urokinase.

10. A isolated cell, comprising:

the nucleic acid molecule of claim 3; and a reporter sequence;

wherein the control region is operably linked to the reporter sequence so as to effectively initiate, terminate or regulate the transcription of the reporter sequence.

11. The cell of claim 10, wherein the reporter sequence encodes an enzyme that produces a detectable colorimetric or a fluorometric change in the cell.

12. The cell of claim 11, wherein the enzyme is selected from the group consisting of luciferase, a green fluorescent protein, chloramphenicol acetyl transferase, β-galactosidase, β-lactamase, secreted placental alkaline phosphatase, human growth hormone, an esterase, a phosphatase, tissue plasminogen activator and urokinase.

* * * * *

UNITED STATES PATENT AND TRADEMARK OFFICE

CERTIFICATE OF CORRECTION

PATENT NO. : 7,098,025 B1
APPLICATION NO. : 09/463542
DATED : August 29, 2006
INVENTOR(S) : Auwerx et al.

It is certified that error appears in the above-identified patent and that said Letters Patent is hereby corrected as shown below:

IN THE TITLE PAGES:

Item [56] References Cited, in OTHER PUBLICATIONS:
in the second Auwerx et al., please insert --apo--between “LP1 and” and “C-III”
in Belluzzi et al., please replace “Belluzi” with --Belluzzi--,
please replace “preparationon” with --preparation--, and
please replace “crohn’s” with --Crohn’s--
in Christy et al., please replace “preaddipocytes” with --preadipocytes--
in Desvergene, B. and W. Wahli, please replace “*Expressio*” with --*Expression*--
in Hertz et al., please replace “ malic’ ” with --‘malic’--
in Ricote et al., please replace “lipoprotien” with --lipoprotein--, and
please replace “(1988)” with --(1998)--
in the fourth Schoonjans et al., please replace “byfibric-acid” with --by fibric-acid--
in the fourth Tontonoz et al., please replace “mPPAr$\gamma$2” with --mPPAR$\gamma$2--
in the second Kliewer et al., please replace “J,” with --$J_2$--

Signed and Sealed this

Sixteenth Day of January, 2007

JON W. DUDAS
*Director of the United States Patent and Trademark Office*

SEQUENCE LISTING

```
<160> NUMBER OF SEQ ID NOS: 60

<210> SEQ ID NO 1
<211> LENGTH: 503
<212> TYPE: DNA
<213> ORGANISM: Human PPARγ1 proximal promoter, exon A1, and intron A1

<400> SEQUENCE: 1

cccctgcccc tgcccctgcc cccaccccca cccccacccc cacccccagc cggcgcccgc     60

gcccgccccc gcgccgggcc cggctcggcc cgacccggtt ccgccgcggg caggcggggc    120

ccagcgcact cggagcccga gcccgagccg cagccgccgc ctggggcgct tgggtcggcc    180

tcgaggacac cggagagggg cgccacgccg ccgtggccgc aggtcagagt acgggtgccc    240

gcggcgctcg ggaaccggct gctgcctggg cggggagtgc tcagggaggg ggcgcggagg    300

gctggggccg agggtctggg gggtagggcc gaggaaacgg caactgacgg ggtcccagac    360

ggatgagagc tggggagaag ggggtctcgg ctgaggggtc cggggctgag gcacggtcat    420

ggtccggcag gacccggact gacgggtctc gggcgggcgg ctcacgggtg accgggtgaa    480

tgggtctcgg gctgacggca ccc                                            503


<210> SEQ ID NO 2
<211> LENGTH: 2688
<212> TYPE: DNA
<213> ORGANISM: Human PPARγl promoter

<400> SEQUENCE: 2

ggagctccac gcggtggcgg ccgctctaga actagtggat cccccgggct gcaggaattc     60

gaggctgcag tgaactatga ttgcaccact gcactccagc ctgggtgaga gagcaatacc    120

ttgtctcaaa acaaacaaac aaacaaaacc ccatgagata tcacttcata ccctttaggt    180

tggctaaaat aaaaaagact ataacaagtg ttgacaagga tgtggaaaaa ctggaaccct    240

gacacattgc tggtgggatt gtaaaatggt gtgcccactt tggaaaacag actggcagtt    300

cctcaaaaac accgagttac gttatgatcc tgcagttctg tccctaggta tatactcaag    360

agaaataaaa atatatgtcc acaagtaacc ttgtacatga atgctcacag cagcattatt    420

cataatagcc cataaaagta gaaacaacct aaatattcat caattcatgg gatgaataaa    480

caaaatgtgg tatatgtgta taatggaata ttgaccataa aaaggaatga aatattaata    540

taagctataa catggatgag cctccacaaa tactatgcta agtgaaagaa gaaagtcaca    600

aaggacttca tattctatga ttctatttat atgaattgtc cagaataggt aaatctatag    660
```

-continued

```
agaaagaata tctctatcta gagttggtgg aatgactgtt aatggagagg gggttccttt    720

ttggagtgat gaaaatgttc taagggtaga tttggtgatg atggcacaac tctgtcaata    780

aactaaaact cattgaactg tacattttat ttatttattt ttgagatgga gtcttgctct    840

ggggctgaag tgcagtggcg caatctcggc ttgtaacctc tgcctcccag ggtcaagcga    900

ttctactgcc tcagcccccc gagtagctga gattacaggc acgtgccacc acgcccagct    960

aatttttgta tttcttagta gagatggagt ttcaccatgt tggccaggct ggtcttgaac   1020

tcccggcctc aagtgatcca cctgcctcgg cctcccaaag tgctgggatt acaggcgtga   1080

gctgccatac ccggcctgaa ttgtacattt tacttctatg gtatttacat tttagattat   1140

attaattatt cctcaataaa gctgtgattt taaaaagcag gctaggcgca gtggctggtg   1200

cctataatcc cagcactttg gaaagctgag gcaggaggat cacttgagcc caggagtttc   1260

agactagtct aggcaacatg tcaagacaca gtctctacta aacaattaaa attaaaaaaa   1320

aaaattagcc aggcatggtg gtgtgcacct gtagtcccag ctacttggga gcctggggtg   1380

ggaggattcc ttgagcccgg gaagtcgagg ctgaagtgag ccgtgattgc gccacagcac   1440

tccagcctgg gcgacacagc aacaccctgt ctcatggaag aaagaaagaa aagaaaggaa   1500

gaaagaaaaa aaaaaagcag attggaactc tggaattaac aagaagtagg acgcacggag   1560

cacttccgcc tgagtggaga ctgtggatcc gggtcaacct gactacctaa atcacaggcc   1620

aataaatggt ctttcagtgg tcagtccctg taagatccgt ggctctcagc ttcttatctt   1680

aggggctgtg gaggaaggac atgattatgt tgatttaagc gctgaatatt ttcccttgtg   1740

atacccatcc tcgcaaaact ttgcttcaac cacaaacgag gaccttctgt accagagggg   1800

caataacaca atgaagctag gaagaaatgc agagcacccc agcatacagt ccataagctt   1860

cctgaagtgg ggggcctcag gcatcgctgc ctccccaaag aggatcaggc ccagaacagt   1920

atgctccaga aataagactg gaaaaaggga aagaggggcc tcaagtccag gagaccagcg   1980

gctttctgaa cgcgcacctg ccaacccact ttggacaggt cacgatggac agcgtggcag   2040

gaaaagaaaa ggtcactgtc tacccaacac atgagaaact gtttctcgtg cctcacgtcc   2100

ccactccgtc cccacccatg ttgtctgagt ccctcggtgt cagaaacact gctaagaaat   2160

ttaagaaatt ctgttaatga gtttaagaaa tgtttttaat gattaaaagt cagtgacttg   2220

tgaataacca tgtaacttac aaacgcaagg aactctgaaa gtgtgcagca ccaccgatca   2280

gaagagaaaa ccaagggacc cgaaatatgc tttaattaaa ttttctttta aaatgtcact   2340

ggaaagaaca tcttgggaag acggcctggc cgatcgccgt gtgaagggca agccactctg   2400

gccgagaggg agccccacac ctcggtctcc ccagaccggc cctggccggg ggcatccccc   2460

taaacttcgg atccctcctc ggaaatggga ccctctctgg gccgcctccc agcggtggtg   2520

gcgaggagca aacgacacca ggtagctgcc gcggggcaga gagtggacgc gggaaagccg   2580

gtggctcccg ccgtgggccc tactgtgcgc gggcggcggc cgagcccggg ccgctccctc   2640

ccagtcgcgc gccgccgccc gcgccctgtt tgggttcatg gggggtg                 2688
```

<210> SEQ ID NO 3
<211> LENGTH: 2045
<212> TYPE: DNA
<213> ORGANISM: Human PPARγ2 promoter, exon B, and intron B

<400> SEQUENCE: 3

```
gaattcaact gaatatagag aaaactaatt ttacacaact gtaatcactg tagtcatttg     60
```

-continued

```
gacaaattag caaacccaag ttttgcttta acttggattg ccttaataaa gatgttttgg    120

ggcttaatgg cacagttgct caactccccc actttattcc gtgatgttca gacccagcca    180

gcatttcccc atcaggctct tgcaccatga ttgacaggga cacttttact agtccccttg    240

aagaatgaat agttactcaa tggagattaa ccagatatat atttatttta ctcagaatat    300

cacgataagt ataattcaga gaattattgc cttctaatat actgccctgt gtgggggcgt    360

ctttgaaagt ccgcaaagtc actgcaattc taataggcca ctcatgtgac aagacctgct    420

cccacatcgg taatttggca cagctagtat ttctccttgc caaaaagggc aaaggccttg    480

agcaagaagc cagctttttc ctgattacaa aactgaccac aattcctcgc caacctaaca    540

gcgtaagtct atttttttct ggtggtgtgt tattcttctc atagagaact ccattttttc    600

attatgacat agcacttatc gtttaaacat caattgatgt tcaaacatca gctggtgtaa    660

cattgctgca gttgctattg atggataagc tgaagttttt aagaaagcaa acccgatgta    720

taaaattgaa accagatcaa acccttcttc attctcagct atttaatttt acagaattta    780

gatagcagtc agtatcattt tgggcttcac aaatcagtag agtaagtacc ttaggaatat    840

aacatttcag tagcatgctg ataccaacgt ttaaactatg gatacatatt tgaattccaa    900

atttttcttc agataatgtg attagagatt agagattcaa ccagggatag acaccgaaag    960

aaaactttgc ccaaataagc tttctggtat ttcataagca agagatttaa gttttccatt   1020

taagaagcca ttgtgaatta tacaacaata aaaaatgcaa gtggatattg aacagtctct   1080

tctctgataa ttctaaatac agtacagttc acgcccctca cgagacactg aacatgtggt   1140

caccggcgag acagtgtggc aatattatcc ctgtaatgta ccaagtcttg ccagagcagt   1200

gaacattatg acacaacttt ttgtcacagc tggctcctaa taggacagtg ccagccaatt   1260

caagcccagt cctttctgtg tttattccca tctctcccaa atatttggaa actgatgtct   1320

tgactcatgg gtgtattcac gattctgtta cttcaagtct ttttctttta acggattgat   1380

cttttgctag atagagacaa aatatcagtg tgaattacag caaacccata ttccatgctg   1440

ttatgggtga aactctggga gattctccta ttgacccaga aagcgattcc ttcactgata   1500

cactgtctgc aaacatatca caaggtaaag ttccttccag atacggctat tggggacgtg   1560

ggggcattta tgtaagggta aaattgctct tgtagtttgt cttccaggtt gtgtttgttt   1620

taatactatc atgtgtacac tccagtattt taatgcttag ctcgttgcta tcgcgttcat   1680

ttaaaaacat gttcagaacc ttaaaaaagg aaacctaacc taatctatct tatctctgtg   1740

catggctccc atttcctgaa ttttaagcat taaaggtata gttatatcca aaaacaatcc   1800

tgttcatctt tatttcctga gtttgcatag atttcccaag aatacataat ggctttttag   1860

acttgaaggg tcacttttcc tctttcatct catatgttag agatctctca taactgtgtt   1920

atccctcttg cagcactttt attcctcttg aatacctcag ctcttttctg ttctattttg   1980

aaatctaagt atgtgtgtgc acttcagctc tcccaaagaa tgtatatccc acaatgtagg   2040

acaag                                                                2045
```

<210> SEQ ID NO 4
<211> LENGTH: 27
<212> TYPE: DNA
<213> ORGANISM: LF-2

<400> SEQUENCE: 4

```
tctccggtgt cctcgaggcc gacccaa                                          27
```

-continued

<210> SEQ ID NO 5
<211> LENGTH: 27
<212> TYPE: DNA
<213> ORGANISM: LF-14

<400> SEQUENCE: 5
agtgaaggaa tcgctttctg ggtcaat 27

<210> SEQ ID NO 6
<211> LENGTH: 27
<212> TYPE: DNA
<213> ORGANISM: LF-18

<400> SEQUENCE: 6
agctgatccc aaagttggtg ggccaga 27

<210> SEQ ID NO 7
<211> LENGTH: 30
<212> TYPE: DNA
<213> ORGANISM: LF-20

<400> SEQUENCE: 7
cattccattc acaagaacag atccagtggt 30

<210> SEQ ID NO 8
<211> LENGTH: 30
<212> TYPE: DNA
<213> ORGANISM: LF-21

<400> SEQUENCE: 8
ggctcttcat gaggcttatt gtagagctga 30

<210> SEQ ID NO 9
<211> LENGTH: 29
<212> TYPE: DNA
<213> ORGANISM: LF-22

<400> SEQUENCE: 9
gcaattgaat gtcgtgtctg tggagataa 29

<210> SEQ ID NO 10
<211> LENGTH: 29
<212> TYPE: DNA
<213> ORGANISM: LF-23

<400> SEQUENCE: 10
gtggatccga cagttaagat cacatctgt 29

<210> SEQ ID NO 11
<211> LENGTH: 30
<212> TYPE: DNA
<213> ORGANISM: LF-24

<400> SEQUENCE: 11
gtagaaataa atgtcagtac tgtcggtttc 30

<210> SEQ ID NO 12
<211> LENGTH: 29
<212> TYPE: DNA
<213> ORGANISM: LF-25

<400> SEQUENCE: 12
tcgatatcac tggagatctc cgccaacag 29

-continued

<210> SEQ ID NO 13
<211> LENGTH: 30
<212> TYPE: DNA
<213> ORGANISM: LF-26

<400> SEQUENCE: 13
acataaagtc cttcccgctg accaaagcaa 30

<210> SEQ ID NO 14
<211> LENGTH: 29
<212> TYPE: DNA
<213> ORGANISM: LF-27

<400> SEQUENCE: 14
ctctgctcct gcagggggt gatgtgttt 29

<210> SEQ ID NO 15
<211> LENGTH: 29
<212> TYPE: DNA
<213> ORGANISM: LF-28

<400> SEQUENCE: 15
gaagttcaat gcactggaat tagatgaca 29

<210> SEQ ID NO 16
<211> LENGTH: 29
<212> TYPE: DNA
<213> ORGANISM: LF-29

<400> SEQUENCE: 16
gagctccagg ggttgtagca ggttgtctt 29

<210> SEQ ID NO 17
<211> LENGTH: 28
<212> TYPE: DNA
<213> ORGANISM: LF-33

<400> SEQUENCE: 17
gacgggctga ggagaagtca cactctga 28

<210> SEQ ID NO 18
<211> LENGTH: 28
<212> TYPE: DNA
<213> ORGANISM: LF-35

<400> SEQUENCE: 18
agcatggaat aggggtttgc tgtaattc 28

<210> SEQ ID NO 19
<211> LENGTH: 24
<212> TYPE: DNA
<213> ORGANISM: LF-36

<400> SEQUENCE: 19
tagtacaagt ccttgtagat ctcc 24

<210> SEQ ID NO 20
<211> LENGTH: 24
<212> TYPE: DNA
<213> ORGANISM: LF-44

<400> SEQUENCE: 20
gtcggcctcg aggacaccgg agag 24

<210> SEQ ID NO 21
<211> LENGTH: 24
<212> TYPE: DNA
<213> ORGANISM: LF-58

<400> SEQUENCE: 21
cactcatgtg acaagacctg ctcc 24

<210> SEQ ID NO 22
<211> LENGTH: 24
<212> TYPE: DNA
<213> ORGANISM: LF-59

<400> SEQUENCE: 22
gccgacacta aaccaccaat atac 24

<210> SEQ ID NO 23
<211> LENGTH: 24
<212> TYPE: DNA
<213> ORGANISM: LF-60

<400> SEQUENCE: 23
cgttaaaggc tgactctcgt ttga 24

<210> SEQ ID NO 24
<211> LENGTH: 26
<212> TYPE: DNA
<213> ORGANISM: AII J PPRE

<400> SEQUENCE: 24
gatccttcaa cctttaccct ggtaga 26

<210> SEQ ID NO 25
<211> LENGTH: 30
<212> TYPE: DNA
<213> ORGANISM: ACO PPRE

<400> SEQUENCE: 25
gatcccgaac gtgacctttg tcctggtccc 30

<210> SEQ ID NO 26
<211> LENGTH: 27
<212> TYPE: DNA
<213> ORGANISM: LPL PPRE

<400> SEQUENCE: 26
gatccgtctg ccctttcccc ctcttca 27

<210> SEQ ID NO 27
<211> LENGTH: 19
<212> TYPE: DNA
<213> ORGANISM: γ AS

<400> SEQUENCE: 27
gcattatgag catccccac 19

<210> SEQ ID NO 28
<211> LENGTH: 20
<212> TYPE: DNA
<213> ORGANISM: γS

<400> SEQUENCE: 28
tctctccgta atggaagacc 20

<210> SEQ ID NO 29
<211> LENGTH: 19
<212> TYPE: DNA
<213> ORGANISM: γ2S

<400> SEQUENCE: 29
gcgattcctt cactgatac 19

<210> SEQ ID NO 30
<211> LENGTH: 52
<212> TYPE: DNA
<213> ORGANISM: Oligonucleotide
<220> FEATURE:
<223> OTHER INFORMATION: "n" stands for a, g, c or t.
"v" stands for a, g or c.

<400> SEQUENCE: 30
ttctagaatt cagcggccgc tttttttttt tttttttttt tttttttttt vn 52

<210> SEQ ID NO 31
<211> LENGTH: 201
<212> TYPE: DNA
<213> ORGANISM: PPARγ1 proximal promoter

<400> SEQUENCE: 31
acccccaccc ccacccccag ccggcgcccg cgcccgcccc cgcgccgggc ccggctcggc 60
ccgacccgga tccgccgccg cgggcaggcg gggcccagcg cactcggagc ccgagcccga 120
gccgcagccg ccgcctgggg cgcttgggtc ggcctcgagg acaccggaga ggggcgccac 180
gccgccgtgg ccgcagaaat g 201

<210> SEQ ID NO 32
<211> LENGTH: 177
<212> TYPE: DNA
<213> ORGANISM: PPARγ2 proximal promoter

<400> SEQUENCE: 32
gtcctttctg tgtttattcc catctctccc aaatatttgg aaactgatgt cttgactcat 60
gggtgtattc acgattctgt tacttcaagt ctttttcttt taacggattg atcttttgct 120
agatagagac aaaatatcag tgtgaattac agcaaaccca tattccatgc tgttatg 177

<210> SEQ ID NO 33
<211> LENGTH: 468
<212> TYPE: DNA
<213> ORGANISM: PPARγ3 proximal promoter

<400> SEQUENCE: 33
taatcctttt aaggtctagt ttttcttaag tctgtgcagt aatagaggta tcgtcattca 60
tgtgacataa aagatggaaa ggggcttcat tcatgttagt gatggaaata ggaaagtagg 120
tgaagtgatt ttaatagatg tttcttttat gaaataattt ttaaagattg tccagccctg 180
catgatttat gatgaatcat tttgtggtct gttagttact tttagagaat agaaagcatt 240
gtaggctcag ggaaagcaaa cattcagaat gaaatccaat agagaaggta aatttatttg 300
ggcatgtaca ttttggcagc ctaggctgtg tacatgtgta cacattctga acatgtgtgt 360
atattgaaaa tcttgtctct tttttattgt taagatttga aagaagccga cactaaacca 420
ccaatataca acaaggccat tttgtcaaac gagagtcagc ctttaacg 468

<210> SEQ ID NO 34
<211> LENGTH: 1463
<212> TYPE: DNA
<213> ORGANISM: PPARγ3 promoter, exon A2, and intron A2

<400> SEQUENCE: 34

```
gagaatacag gcacatgcca ccatgcccag ctaatttttc tgttttttgt agagacagga     60
tttcgctgtg gtgctcaggc tggtctccaa ctcctgggct caagcaatcc gcctgcctca    120
gccttccaaa gtgaaaaggt tttctctcat ttttcaaata gaagtactaa acaatgccag    180
agaaataaat aaacaggcaa aatacgttgg ctatagttta tattatttcc tgctacagtt    240
aacaaaatgg gaagacattt tatcttcatg gtctactaca tttatgccat gtgttaagta    300
ataaaatagc ttttgtaaat tataaattaa aaggtacaga tttaaaagag aaaatactgt    360
agagttttca tgtaggtaag actgtgtaga atgtcgggtc tcgatgttgg cgctattcaa    420
gccctgatga taaggctttt ggcattagat gctgttttgt cttcatggaa aatacagcta    480
ttctaggatc cttgagcctt tcataagaga taaggttgtg aatcctaaga ccctaggacc    540
atttacttag atgatctgct ctctggttcg tcctctgaaa agtctgcttc gtgaggggtg    600
tgctgcattt gccttgccta agtggtgtgg cacacaactg tactgtcacc ttaggcttaa    660
taaccatgtg tcatctagaa tgaagttata ttttaaaaag gatcgttttt gccatgtata    720
aattttcaaa cattaacttt cagggttatt aatcctttta aggtctagtt tttcttaagt    780
ctgtgcagta atagaggtat cgtcattcat gtgacataaa agatggaaag gggcttcatt    840
catgttagtg atggaaatag gaaagtaggt gaagtgattt taatagatgt ttcttttatg    900
aaataatttt taaaagattg tccagccctg catgatttat gatgaatcat tttgtggtct    960
gttagttact tttagagaat agaaagcatt gtaggctcag ggaaagcaaa cattcagaat   1020
gaaatccaat agagaaggta aatttatttg ggcatgtaca ttttggcagc ctaggctgtg   1080
tacatgtgta cacattctga acatgtgtgt atattgaaaa tcttgtctct tttttattgt   1140
taagatttga aagaagccga cactaaacca ccaatataca acaaggccat tttctcaaac   1200
gagagtcagc ctttaacggt aagtaaaatc agaatttata ctgcatttgt attgaaaagt   1260
atccctttta aagaatatgt aaattataca ttgttatttt attgtaaaat ttcctagaga   1320
gtgatttttg actattataa tactttctgc tatataattt tccagtcagt tggactatgc   1380
agtgtaacat atttgtctaa cacaaaacaa aggtaagata ggaaaatgac ctagaagttg   1440
agaaataact caaatcctta aaa                                           1463
```

<210> SEQ ID NO 35
<211> LENGTH: 695
<212> TYPE: DNA
<213> ORGANISM: Intron B, exon 1, and intron 1

<400> SEQUENCE: 35

```
ctgggataac aggtgtgagc cactgtgcct ggcctgtata ctataagttt aaaatttttg     60
tctattatac tcaataaagc tggacaaaat tttaaataaa taacagcagt cattaacaga    120
ctcaattgat gacctaatgt agaagttaat gagagcaggc ctgttggcaa aaaggcattt    180
atatggatac actgtatgta tctgcactgt ttcaggatcc tctattatga tacctgggta    240
aagggtgact tcctttctat cataaaacag cctagacagc actaagaagg tggttatgtt    300
cttttctgtt gttgtgagcg cccagatgag attactttgc caaagactct tttcatttct    360
ctttctgaaa ctctgtgaga ttgctgtgtt ctctaggact taacttcaca gctagtctat    420
```

-continued

```
ttttcctttc agaaatgacc atggttgaca cagagatgcc attctggccc accaactttg    480

ggatcagctc cgtggatctc tccgtaatgg aagaccactc ccactccttt gatatcaagc    540

ccttcactac tgttgacttc tccagcattt ctactccaca ttacgaagac attccattca    600

caagaacaga tccagtggtt gcagattaca agtatgacct gaaacttcaa gagtaccaaa    660

gtatgatgtt tgttttcact tttcagacta ctagg                               695
```

<210> SEQ ID NO 36
<211> LENGTH: 313
<212> TYPE: DNA
<213> ORGANISM: Intron 1, exon 2, and intron 2

<400> SEQUENCE: 36

```
ctgttttcat gggataatta tcctctcaca tgtctccata cacaggtgca atcaaagtgg     60

agcctgcatc tccaccttat tattctgaga agactcagct ctacaataag cctcatgaag    120

agccttccaa ctccctcatg gcaattgaat gtcgtgtctg tggagataaa gcttctggat    180

ttcactatgg agttcatgct tgtgaaggat gcaaggtaat taaaaaaaaa gtcttcaaag    240

aaattgttga aactttatta tttcatttca gcagaacccc ttttttaggt gatacaatat    300

atgaattttt ttt                                                       313
```

<210> SEQ ID NO 37
<211> LENGTH: 473
<212> TYPE: DNA
<213> ORGANISM: Intron 2, exon 3, and intron 3

<400> SEQUENCE: 37

```
gatacctttc gctgtaggtt cgtgcttcca tgtgtcataa agacttaaaa tttgcttctt     60

ttttatccct ttgcagggtt tcttccggag aacaatcaga ttgaagctta tctatgacag    120

atgtgatctt aactgtcgga tccacaaaaa aagtagaaat aaatgtcagt actgtcggtt    180

tcagaaatgc cttgcagtgg ggatgtctca taatggtaag taaacagtca tcaccatata    240

ctttattatt ctcattatag ctgccagacc agtggacact aaagccattg ccaaaaaatgt   300

gtacagtttt tccaccaaat gccagaattt agaatattgc atggcgataa aacatttctc    360

ttttaggtca gtgtttttaa agttttatta tagaaccttt ctctctgtgg ttgggcatct    420

gccatgagga gaaaagagac ttgaaaaatc tgggggatta tgggaaaaac ctt           473
```

<210> SEQ ID NO 38
<211> LENGTH: 706
<212> TYPE: DNA
<213> ORGANISM: Intron 3, exon 4, and intron 4

<400> SEQUENCE: 38

```
acaactttga attctgcaca gtttcgtatt ttaattcgtg aaacgtgttg atccttctaa     60

gtgcctgacc ttaggtcaag tgctggggat acaaagaagg tgacctttga attgggtctt    120

gagggatgag taggagttgg ttctcaatta tttcacgttt aagtcgacat acttccctcc    180

ctttgctaaa ctcgaattct ttcactttct cagcaggagt atgcattaac ttttaaaaat    240

gaaagttaac ggtttaattt ttactgatgg tctgtgctac ttttgtgaaa taaaaacatg    300

agcaaagtgg tagacagaaa ccaggactca agagcagtgg aggaggaggg cttctactgt    360

gtgggaacga gggctgggag agcacagtgt gtgttcagag cagtagtaat ccaatgattc    420

atcctgtcat tcctcttcct ctatagccat caggtttggg cggatgccac aggccgagaa    480
```

-continued ggagaagctg ttggcggaga tctccagtga tatcgaccag ctgaatccag agtccgctga 540
cctccgtgcc ctggcaaaac atttgtatga ctcatacata aagtccttcc cgctgaccaa 600
agcaaaggcg agggcgatct tgacaggaaa gacaacagac aaatcagtta gttctcttct 660
gctgtcttca ttgggggagg cgggaagttg ttttgggatt tttgtt 706

<210> SEQ ID NO 39
<211> LENGTH: 732
<212> TYPE: DNA
<213> ORGANISM: Intron 4, exon 5, and intron 5

<400> SEQUENCE: 39
gggaaagaag accaaaattg gtgaaatatg tttggtccca gaagataatt aagatgaata 60
aaagaacttg agagtatttt ctcattatta agcatcttca gctttaaaga ttttagttag 120
caaagcaagt ttacataaac agttttctga acctgggatg gcattcactg tgagttagaa 180
atctccaagt catcccacgt tttccctgtt ttatttgcag ccattcgtta tctatgacat 240
gaattcctta atgatgggag aagataaaat caagttcaaa cacatcaccc ccctgcagga 300
gcagagcaaa gaggtggcca tccgcatctt tcagggctgc cagtttcgct ccgtggaggc 360
tgtgcaggag atcacagagt atgccaaaag cattcctggt tttgtaaatc ttgacttgaa 420
cgaccaagta actctcctca aatatggagt ccacgagatc atttacacaa tgctggcctc 480
cttgatgaat aaagatgggg ttctcatatc cgagggccaa ggcttcatga caagggagtt 540
tctaaagagc ctgcgaaagc cttttggtga ctttatggag cccaagtttg agtttgctgt 600
gaagttcaat gcactggaat tagatgacag cgacttggca atatttattg ctgtcattat 660
tctcagtgga ggtaagattt gtcttttgat cttctatgaa agagggtggg atgatggtgg 720
ggtggccaaa ag 732

<210> SEQ ID NO 40
<211> LENGTH: 592
<212> TYPE: DNA
<213> ORGANISM: Intron 5, exon 6, and 3' UTR
<220> FEATURE:
<223> OTHER INFORMATION: “n” stands for a, g, c or t.

<400> SEQUENCE: 40
tccccaccta tttaagatac aaagcaaaac aaaccaaaaa tacagatgag ttgcttggta 60
gagntgcnta ggcctccaag gcggggccca gaggattttt tgactgaacc ccctgttgtg 120
ttttccatat gtgcttcccc agaccgccca ggtttgctga atgtgaagcc cattgaagac 180
attcaagaca acctgctaca agccctggag ctccagctga agctgaacca ccctgagtcc 240
tcacagctgt ttgccaagct gctccagaaa atgacagacc tcagacagat tgtcacggaa 300
cacgtgcagc tactgcaggt gatcaagaag acggagacag acatgagtct tcacccgctc 360
ctgcaggaga tctacaagga cttgtactag cagagagtcc tgagccactg ccaacatttc 420
ccttcttcca gttgcactat tctgagggaa aatctgacca taagaaattt actgtgaaaa 480
agcgttttaa aaagaaaagg gtttagaata tgatctattt tatgcatatt gtttataaag 540
acacatttac aatttacttt taatattaaa aattaccata ttatgaaatt gc 592

<210> SEQ ID NO 41
<211> LENGTH: 13
<212> TYPE: DNA
<213> ORGANISM: PPARγ3-E-box

<400> SEQUENCE: 41

```
attcatgtga cat                                                    13


<210> SEQ ID NO 42
<211> LENGTH: 13
<212> TYPE: DNA
<213> ORGANISM: PPARγ3-E-box

<400> SEQUENCE: 42

attcatgcat cat                                                    13


<210> SEQ ID NO 43
<211> LENGTH: 13
<212> TYPE: DNA
<213> ORGANISM: A1 (97) Donor

<400> SEQUENCE: 43

cgcaggtcag agt                                                    13


<210> SEQ ID NO 44
<211> LENGTH: 13
<212> TYPE: DNA
<213> ORGANISM: A1 (97) Acceptor

<400> SEQUENCE: 44

ttgttaagat ttg                                                    13


<210> SEQ ID NO 45
<211> LENGTH: 13
<212> TYPE: DNA
<213> ORGANISM: A2 (74) Donor

<400> SEQUENCE: 45

taacggtaag taa                                                    13


<210> SEQ ID NO 46
<211> LENGTH: 13
<212> TYPE: DNA
<213> ORGANISM: A2 (74) Acceptor

<400> SEQUENCE: 46

cctttcagaa atg                                                    13


<210> SEQ ID NO 47
<211> LENGTH: 12
<212> TYPE: DNA
<213> ORGANISM: B (211) Donor

<400> SEQUENCE: 47

caaggtaaag tt                                                     12


<210> SEQ ID NO 48
<211> LENGTH: 13
<212> TYPE: DNA
<213> ORGANISM: B (211) Acceptor

<400> SEQUENCE: 48

cctttcagaa atg                                                    13


<210> SEQ ID NO 49
<211> LENGTH: 12
<212> TYPE: DNA
<213> ORGANISM: 1 (213) Donor
```

<400> SEQUENCE: 49
caaagtatga tg 12

<210> SEQ ID NO 50
<211> LENGTH: 13
<212> TYPE: DNA
<213> ORGANISM: 1 (231) Acceptor

<400> SEQUENCE: 50
atacacaggt gca 13

<210> SEQ ID NO 51
<211> LENGTH: 12
<212> TYPE: DNA
<213> ORGANISM: 2 (170) Donor

<400> SEQUENCE: 51
caaggtaatt aa 12

<210> SEQ ID NO 52
<211> LENGTH: 12
<212> TYPE: DNA
<213> ORGANISM: 2 (170) Acceptor

<400> SEQUENCE: 52
ctttgcaggg tt 12

<210> SEQ ID NO 53
<211> LENGTH: 12
<212> TYPE: DNA
<213> ORGANISM: 3 (139) Donor

<400> SEQUENCE: 53
aatggtaagt aa 12

<210> SEQ ID NO 54
<211> LENGTH: 13
<212> TYPE: DNA
<213> ORGANISM: 3 (139) Acceptor

<400> SEQUENCE: 54
ctctatagcc atc 13

<210> SEQ ID NO 55
<211> LENGTH: 12
<212> TYPE: DNA
<213> ORGANISM: 4 (203) Donor

<400> SEQUENCE: 55
atcagttagt tc 12

<210> SEQ ID NO 56
<211> LENGTH: 12
<212> TYPE: DNA
<213> ORGANISM: 4 (203) Acceptor

<400> SEQUENCE: 56
atttgcagcc at 12

<210> SEQ ID NO 57
<211> LENGTH: 12
<212> TYPE: DNA
<213> ORGANISM: 5 (451) Donor -continued

```
<400> SEQUENCE: 57

ggaggtaaga tt                                                        12


<210> SEQ ID NO 58
<211> LENGTH: 13
<212> TYPE: DNA
<213> ORGANISM: 5 (451) Acceptor

<400> SEQUENCE: 58

ttccccagac cgc                                                       13


<210> SEQ ID NO 59
<211> LENGTH: 12
<212> TYPE: DNA
<213> ORGANISM: 6 (248) Donor

<400> SEQUENCE: 59

tactagcaga ga                                                        12


<210> SEQ ID NO 60
<211> LENGTH: 44
<212> TYPE: DNA
<213> ORGANISM: Oligonucleotide

<400> SEQUENCE: 60

ctaatacgac tcactatagg gctcgagcgg ccgcccgggc aggt                     44
```